US012590335B2

(12) United States Patent
Symmans et al.

(10) Patent No.: US 12,590,335 B2
(45) Date of Patent: **\*Mar. 31, 2026**

(54) TARGETED MEASURE OF TRANSCRIPTIONAL ACTIVITY RELATED TO HORMONE RECEPTORS

(71) Applicants: Board of Regents, The University of Texas System, Austin, TX (US); Yale University, New Haven, CT (US)

(72) Inventors: William Fraser Symmans, Houston, TX (US); Bruno Sinn, Berlin (DE); Christos Hatzis, Guilford, CT (US); Chunxiao Fu, Pearland, TX (US); Rosanna Lau, Houston, TX (US)

(73) Assignees: Board of Regents, The University of Texas System, Austin, TX (US); Yale University, New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/338,974

(22) Filed: Jun. 21, 2023

(65) Prior Publication Data

US 2024/0218450 A1 Jul. 4, 2024

Related U.S. Application Data

(63) Continuation of application No. 17/822,332, filed on Aug. 25, 2022, which is a continuation of application (Continued)

(51) Int. Cl.
*C12Q 1/6886* (2018.01)
*A61K 31/138* (2006.01)
(Continued)

(52) U.S. Cl.
CPC .......... *C12Q 1/6886* (2013.01); *A61K 31/138* (2013.01); *A61K 31/4196* (2013.01);
(Continued)

(58) Field of Classification Search
CPC ............ C12Q 1/6886; C12Q 2600/106; C12Q 2600/112; C12Q 2600/118; C12Q 2600/158
See application file for complete search history.

(56) References Cited

U.S. PATENT DOCUMENTS 11,459,617 B2 * 10/2022 Symmans ............ A61K 31/566
2007/0134688 A1 6/2007 Symmans et al.
(Continued)

FOREIGN PATENT DOCUMENTS

JP 2006-514967 5/2006
JP 2006-306872 11/2006
(Continued)

OTHER PUBLICATIONS

Ahern, H. The Scientist 9(15):20 (6 pages). (Year: 1995).*
(Continued)

*Primary Examiner* — Diana B Johannsen
(74) *Attorney, Agent, or Firm* — pH IP Law

(57) ABSTRACT

Provided herein are methods of determining tumoral sensitivity to hormonal (endocrine) therapy based upon an index of estrogen receptor (ER)- and progesterone receptor (PR)-related genes, referred to as the sensitivity to endocrine therapy index ($SET_{ER/PR}$ index), and may have additional consideration for the proportion of ER gene (ESR1) RNA transcripts that contain a mutation relative to the value of the $SET_{ER/PR}$ index. Further provided are methods of treating breast cancer patients determined to be sensitive to an endocrine therapy by the $SET_{ER/PR}$ index.

16 Claims, 38 Drawing Sheets

Related U.S. Application Data

No. 16/097,102, filed as application No. PCT/US2017/030077 on Apr. 28, 2017, now Pat. No. 11,459,617.

(60) Provisional application No. 62/329,774, filed on Apr. 29, 2016.

(51) Int. Cl.

| | |
|---|---|
| *A61K 31/4196* | (2006.01) |
| *A61K 31/566* | (2006.01) |
| *A61K 45/06* | (2006.01) |
| *A61P 35/04* | (2006.01) |
| *G16B 10/00* | (2019.01) |
| *G16B 25/10* | (2019.01) |
| *G16B 25/20* | (2019.01) |

(52) U.S. Cl.
CPC ............ *A61K 31/566* (2013.01); *A61K 45/06* (2013.01); *A61P 35/04* (2018.01); *G16B 10/00* (2019.02); *G16B 25/10* (2019.02); *G16B 25/20* (2019.02); *C12Q 2600/106* (2013.01); *C12Q 2600/112* (2013.01); *C12Q 2600/118* (2013.01); *C12Q 2600/158* (2013.01)

(56) References Cited

U.S. PATENT DOCUMENTS

| | | | |
|---|---|---|---|
| 2011/0217297 A1* | 9/2011 | Kao | A61P 35/00 514/249 |
| 2013/0065786 A1 | 3/2013 | Dartmann et al. | |
| 2015/0024952 A1 | 1/2015 | Alarcon et al. | |
| 2015/0258099 A1 | 9/2015 | Hager et al. | |
| 2015/0368721 A1 | 12/2015 | Symmans et al. | |
| 2022/0403474 A1* | 12/2022 | Symmans | G01N 33/57484 |

FOREIGN PATENT DOCUMENTS

| | | | | |
|---|---|---|---|---|
| JP | 2009-507496 | 2/2009 | | |
| JP | 2009-511609 | 3/2009 | | |
| JP | 2010-527620 | 8/2010 | | |
| JP | 2011-524162 | 9/2011 | | |
| JP | 2012-512259 | 5/2012 | | |
| JP | 2012-530074 | 11/2012 | | |
| WO | WO-9947706 A1 * | 9/1999 | ........... | C12Q 1/6874 |
| WO | WO 2004/087123 | 10/2004 | | |
| WO | WO 2006/119593 | 5/2006 | | |
| WO | WO 2006/114702 | 11/2006 | | |
| WO | WO 2007/030611 | 3/2007 | | |
| WO | WO 2007/045027 | 4/2007 | | |
| WO | WO 2008/145125 | 12/2008 | | |
| WO | WO 2009/158143 | 12/2009 | | |
| WO | WO 2010/078042 | 7/2010 | | |
| WO | WO 2010/145010 | 12/2010 | | |
| WO | WO 2011/130495 | 10/2011 | | |
| WO | WO 2012-031008 | 3/2012 | | |
| WO | WO 2013/106913 | 7/2013 | | |
| WO | WO 2014/191726 | 12/2014 | | |
| WO | WO 2015/164501 | 10/2015 | | |
| WO | WO 2016/042164 | 3/2016 | | |
| WO | WO 2016/061142 | 4/2016 | | |

OTHER PUBLICATIONS

Sosnowski, R.G. et al. Proc. Natl. Acad. Sci. USA 94:1119-1123 (Feb. 1997). (Year: 1997).*

Bessa et al., "JDP1 (DNAJC12/Hsp40) expression in breast cancer and its association with estrogen receptor status", *Int. J. Mol. Med.*, 17(2):363-367, 2006.

Extended European Search Report issued in corresponding European Application No. 17790517, mailed on Dec. 6, 2019.

Filipits et al., "A new molecular predictor of distant recurrence in ER-positive, HER2-negative breast cancer adds independent information to conventional clinical risk factors", *Clin. Cancer Res.*, 17:6012-6020, 2011.

Hatzis et al., "Effects of Tissue Handling on RNA Integrity and Microarray Measurements From Resected Breast Cancers", *J. Nat. Cancer Inst.*, 103(24):1871-1883, 2011.

Hoefnagel et al., "Receptor conversion in distant breast cancer metastases", *Breast Cancer Res.*, 12:R75, 2010.

International Preliminary Report on Patentability issued in corresponding PCT Application No. PCT/US2017/030077, mailed on Oct. 30, 2018.

International Search Report and Written Opinion issued in corresponding PCT Application No. PCT/US2017/030077, mailed on Apr. 28, 2017.

Jansen et al., "Decreased expression of ABAT and STC2 hallmarks ER-positive inflammatory breast cancer and endocrine therapy resistance in advanced disease", *Mol. Oncol.*, 9(6):1218-1233, 2015.

Liu et al., "NPY1R is a novel peripheral blood marker predictive of metastasis and prognosis in breast cancer patients", *Oncol. Lett.*, 9:891-896, 2015.

Lower et al., "Impact of metastatic estrogen receptor and progesterone receptor status on survival", *Breast Cancer Res. Treat.*, 90:65-70, 2005.

Office action issued in Japanese Application No. 2018-556452, mailed May 7, 2021.

Office Action issued in Japanese Application No. 2018-556452, mailed Mar. 30, 2022.

Office Action issued in U.S. Appl. No. 16/097,102, mailed Apr. 4, 2022.

Office Action issued in U.S. Appl. No. 16/097,102, mailed Dec. 10, 2021.

Office Action issued in U.S. Appl. No. 16/097,102, mailed Jul. 29, 2021.

Paik et al., "A multigene assay to predict recurrence of tamoxifen-treated, node-negative breast cancer", *N. Engl. J. Med.*, 351:2817-2826, 2004.

QuantiGene RNA Multiplex Set Catalog: Panel Search, 2014.

Rastelli and Crispino, "Factors predictive of response to hormone therapy in breast cancer", *Tumori*, 94:370-383, 2008.

Robinson et al., "Activating ESR 1 mutations in hormone-resistant metastatic breast cancer", *Nat. Genet.*, 45:1446-1451, 2013.

Sussman et al., "SGN-LIVIA: A novel antibody-drug conjugate targeting LIV-1 for the treatment of metastatic breast cancer", *Mol. Cancer Ther.*, 13(12):2991-3000, 2014.

Symmans et al., "Genomic index of sensitivity to endocrine therapy for breast cancer", *J. Clin. Oncol.*, 28:4111-4119, 2010.

Toy et al., "ESR1 ligand-binding domain mutations in hormone-resistant breast cancer", *Nat. Genet.*, 45:1439-1445, 2013.

Van't Veer et al., "Gene expression profiling predicts clinical outcome of breast cancer", *Nature*, 415:530-536, 2002.

Office Action issued in U.S. Appl. No. 17/822,332, mailed May 19, 2025.

Richter et al., "Comparison of fluorescent tag DNA labeling methods used for expression analysis by DNA microarrays," *Biotechniques*, 33(3):620-630, 2002.

Nilsson et al., "Detection of mutations in PCR products from clinical samples by surface plasmon resonance," *Journal of Molecular Recognition*, 10:7-17, 1997.

Office Action issued in U.S. Appl. No. 17/822,332, mailed Dec. 9, 2025.

* cited by examiner $SET_{ER/PR}$ - *Liver Contamination*

*Percent of Liver Contamination*

$SET_{ER/PR}$ - *Normal Breast Contamination*

*Percent of Normal Breast Contamination*

*SET$_{ER/PR}$ - Inter-Laboratory*

*SET$_{ER/PR}$ Intra-Assay (Validation)*

$SET_{ER/PR}$ - Inter-Technology Validation

$SET_{ER/PR}$ - Intra-Assay Validation

*Calibration: Agilent 44K V2 Using FF*

$r^2 = 0.9880$ $p = 0.9940$

U133A

Agilent V2

*Validation: Agilent 44K V2 Using FF*

$r^2 = 0.9599$ $p = 0.9798$

U133A

Agilent V2 Calibrated

*Calibration: Agilent 44K V2 Using FFPE*

*Agilent V2 FFPE*

*Validation: Agilent 44K V2 Using FFPE*

*Agilent V2 FFPE calibrated*

*Calibration: RD Using FFPE*

$r^2 = 0.8203$ $p = 0.9057$

*Validation: RD Using FFPE*

$r^2 = 0.7853$ $p = 0.8862$

MAF PFS: HT, n=58

MAF OS: HT, n=58

RCB / SET$_{ER/PR}$     Number at Risk

| RCB / SET$_{ER/PR}$ | | | | | | | |
|---|---|---|---|---|---|---|---|
| II / High | 30 | 30 | 29 | 26 | 21 | 10 | 4 |
| II / Low | 61 | 54 | 43 | 39 | 27 | 6 | 2 |
| III / High | 21 | 21 | 19 | 17 | 14 | 7 | |
| III / Low | 24 | 15 | 12 | 9 | 2 | 2 | 1 |

*Tumor of patient XY*

*Study I*    *Study II*        *Study III*

AJCC Stage

Relapse Event Biopsied

*Reference Transcripts*

TARGETED MEASURE OF TRANSCRIPTIONAL ACTIVITY RELATED TO HORMONE RECEPTORS

The present application is a continuation of U.S. application Ser. No. 17/822,332, filed Aug. 25, 2022, which is a continuation of U.S. application Ser. No. 16/097,102, filed Oct. 26, 2018, now U.S. Pat. No. 11,459,617, which is a national phase application under 35 U.S.C. § 371 of International Application No. PCT/US2017/030077, filed Apr. 28, 2017, which claims the priority benefit of U.S. Provisional Application Ser. No. 62/329,774, filed Apr. 29, 2016, the entire contents of each of which are hereby incorporated by reference.

The invention was made with government support under Grant No. HHSN261200800001E awarded by the National Institutes of Health. The government has certain rights in the invention.

BACKGROUND OF THE INVENTION

1. Field of the Invention

The present invention relates generally to the fields of molecular biology and medicine. More particularly, it concerns methods of treating cancer based on transcriptional profiling.

2. Description of Related Art

Endocrine therapy (also known as hormonal therapy) is the foundation for palliative treatment of metastatic hormone receptor-positive and HER2-negative (HR+/HER2⁻) breast cancer (Giordano et al., 2014; Cardoso et al., 2014). However, the efficacy of palliative therapy is variable according to the patient and treatment type. Furthermore, there is consistent evidence for molecular progression events which decouple cancer cells from their reliance on estrogen in advanced disease through a change in hormone receptor expression (e.g., a loss of progesterone receptor (PR, gene name PGR) in about 20% of metastatic breast cancers or a loss of estrogen receptor (ER, gene name ESR1) in about 10% of metastatic breast cancers (Lower et al., 2005; Hoefnagel et al., 2010; Amir et al., 2012; Thompson et al., 2010), the acquisition of functionally active gene mutations in ESR1 (Toy et al., 2013; Robinson et al., 2013), and changes in transcriptional profiles towards a decreased dependence on estrogen.

While guidelines currently recommend endocrine therapy as the first-line treatment for patients with relapsed HR⁺/HER2⁻ breast cancer, the selection of later lines of treatment can become increasingly challenging if there is concern that secondary endocrine resistance may have developed (Giordano et al., 2014; Cardoso et al., 2014). Clinical variables can be used to estimate the sensitivity to further endocrine-based therapy, such as the patient's history of prior endocrine sensitivity in the adjuvant setting, the number of previous relapse events, the development of visceral metastases, and the number of previous endocrine (hormonal) treatments administered. While a number of genomic multigene-assays have proven their value in individualizing treatment decisions in early hormone receptor-positive (HR+) breast cancer beyond the use of immunohistochemical evaluation of standard markers (van't Veer et al., 2002; Paik et al., 2004; Filipits et al., 2011), there is need for a customized assay with a strong analytical validity for predicting treatment response for use in the setting of advanced breast cancer, including Stage II, III, or IV as defined by current criteria from the American Joint Commission for Cancer Staging (AJCC Stage).

SUMMARY OF THE INVENTION

Embodiments of the present disclosure provide methods for the detection and treatment of breast tumors sensitive to hormonal therapy (also known as endocrine therapy) alone or in combination with other anti-cancer therapies. In a first embodiment, there is provided a method of treating breast cancer in a patient comprising: (a) determining the expression level of a set of genes in a patient sample that are related to both estrogen receptor (ER) and progesterone receptor (PR) expression; (b) calculating an index of sensitivity to endocrine therapy ($SET_{ER/PR}$ index) based on an index of ER- and PR-related gene expression; and (c) administering an effective amount of a endocrine therapy to the patient based on the predicted sensitivity of the patient's cancer to endocrine therapy ($SET_{ER/PR}$ index).

In another embodiment, the present disclosure provides a method of treating breast cancer in a subject comprising administering an effective amount of an endocrine therapy to said subject, wherein the subject has been determined to be sensitive to endocrine therapy based on a $SET_{ER/PR}$ index. In some aspects, the subject has been determined to be sensitive to endocrine therapy based on a $SET_{ER/PR}$ index by determining the expression level of a set of estrogen receptor (ER)- and progesterone receptor (PR)-related genes in a sample from the subject and calculating the $SET_{ER/PR}$ index based on the ER- and PR-related gene expression.

A further embodiment provides a composition comprising an effective amount of an endocrine therapy for the treatment of breast cancer in a subject identified to be sensitive to endocrine therapy based on a $SET_{ER/PR}$ index. In some aspects, the subject has been determined to be sensitive to endocrine therapy based on a $SET_{ER/PR}$ index by determining the expression level of a set of estrogen receptor (ER)- and progesterone receptor (PR)-related genes in a sample from the subject and calculating the $SET_{ER/PR}$ index based on the ER- and PR-related gene expression.

In some aspects of the above embodiments, calculating the $SET_{ER/PR}$ index comprises normalizing the expression of the set of ER- and PR-related genes to a set of reference genes. In certain aspects, calculating is further defined as the difference between the average expression of the set of ER- and PR-related genes and the average expression of the set of reference genes. In some aspects, the method further comprises the addition of an optimizing constant. In particular aspects, the optimizing constant has a value of 2. In some aspects, a $SET_{ER/PR}$ index greater than 0 identifies a patient as sensitive to endocrine therapy. In certain aspects, a $SET_{ER/PR}$ index greater than 0.5 identifies a patient as sensitive to endocrine therapy. In some aspects, a $SET_{ER/PR}$ index greater than 1 identifies a patient as sensitive to endocrine therapy.

In certain aspects, the set of ER- and PR-related genes comprises at least 10 of the genes selected from the group consisting of SLC39A6, STC2, CA12, ESR1, PDZK1, NPY1R, CD2, MAPT, QDPR, AZGP1, ABAT, ADCY1, CD3D, NAT1, MRPS30, DNAJC12, SCUBE2, and KCNE4. In some aspects, the set of ER- and PR-related genes comprises at least 11, 12, 13, 14, 15, 16 or 17 of the genes selected from the group consisting of SLC39A6, STC2, CA12, ESR1, PDZK1, NPY1R, CD2, MAPT, QDPR, AZGP1, ABAT, ADCY1, CD3D, NAT1, MRPS30, DNAJC12, SCUBE2, and KCNE4. In some aspects, the set of ER- and PR-related genes consists of SLC39A6, STC2, CA12, ESR1, PDZK1, NPY1R, CD2, MAPT, QDPR, AZGP1, ABAT, ADCY1, CD3D, NAT1, MRPS30, DNAJC12, SCUBE2, and KCNE4.

In some aspects, the set of reference genes comprises at least 5 of the genes selected from the group consisting of LDHA, ATP5J2, VDAC2, DARS, UCP2, UBE2Z, AK2, WIPF2, APPBP2, and TRIM2. In certain aspects, the set of reference genes comprises at least 6, 7, 8 or 9 of the genes selected from the group consisting of LDHA, ATP5J2, VDAC2, DARS, UCP2, UBE2Z, AK2, WIPF2, APPBP2, and TRIM2. In some aspects, the set of reference genes consists of LDHA, ATP5J2, VDAC2, DARS, UCP2, UBE2Z, AK2, WIPF2, APPBP2, and TRIM2.

In certain aspects, the breast cancer is Stage II, Stage III or Stage IV breast cancer. In certain aspects, the breast cancer is hormone receptor positive. In some aspects, the hormone receptor is ER and/or PR. In certain aspects, the breast cancer has essentially normal expression of HER2 (i.e., HER2-negative), such as compared to non-cancer level.

In some aspects, the endocrine therapy comprises selective estrogen receptor modulation (SERM), aromatase inhibition (AI), or selective estrogen receptor degradation (SERD) class of treatment. In some aspects, the SERM therapy comprises tamoxifen or toremifene. In certain aspects, the aromatase inhibitor therapy comprises letrozole, anastrozole or exemestane. In some aspects, the SERD therapy comprises fulvestrant. In certain aspects, a second treatment, such as a sequential or concurrently administered treatment, may be administered to increase the effectiveness of the endocrine therapy. In certain aspects, the second treatment comprises an additional endocrine therapy, such as the suppression of ovarian release of estrogen, to increase the effectiveness of the first endocrine therapy. In some aspects, the second treatment comprises a biotherapy to increase the effectiveness of the endocrine therapy.

In certain aspects, the patient sample is blood, saliva, urine, cytology sample, tissue biopsy, or surgically resected tissue. In some aspects, the patient sample is blood. In certain aspects, the tissue biopsy is further defined as formalin-fixed and paraffin-embedded (FFPE). In some aspects, the tissue biopsy is further defined as a tumor biopsy. In certain aspects, the cytology sample or tumor biopsy is preserved by flash freezing or an RNA stabilization agent.

In some aspects, step (a) comprises isolating RNA from the patient sample. In certain aspects, the sample may be digested with a lysis buffer and/or the RNA may be enriched by picodroplet enrichment. In certain aspects, determining the expression level comprises performing reverse transcription-quantitative real-time PCR (RT-qPCR), microarray analysis, or RNA sequencing. In some aspects, determining the expression level comprises direct hybridization to a template, such as Nanostring® nCounter assay or Quantigene assay, picodroplet targeting and reverse transcription, or RNAse protection assay.

In some aspects, the patient has previously been administered an anti-cancer therapy. In certain aspects, the anti-cancer therapy is chemotherapy and/or endocrine therapy. In some aspects, the patient exhibited sensitivity to the chemotherapy and/or endocrine therapy. In certain aspects, the chemotherapy is taxane-anthracycline chemotherapy. In some aspects, the anti-cancer therapy was administered for at least 5 years.

In certain aspects, step (b) further comprises detecting the proportion of transcript which contains a mutation from the ESR1 gene. In some aspects, the proportion is calculated as the expression of mutated ESR1 over the expression of the wild-type ESR1. In certain aspects, the mutation in the ESR1 gene is S463P, V534E, P535H, L536Q, L536R, Y537C, Y537S, Y537N, or D538G. In some aspects, the proportion of mutated ESR1 transcripts in the sample is interpreted relative to the result of the measurement of the $SET_{ER/PR}$ index.

In some aspects, the method further comprises administering at least a second anti-cancer therapy. In certain aspects, the anti-cancer therapy is chemotherapy, immunotherapy, surgery, radiotherapy, or biotherapy. In some aspects, the anti-cancer therapy is a second endocrine therapy. In certain aspects, the endocrine therapy and/or at least a second anti-cancer therapy are administered orally, intravenously, intraperitoneally, intratracheally, intratumorally, intramuscularly, endoscopically, intralesionally, percutaneously, subcutaneously, transcutaneously, regionally, or by direct injection or perfusion. In some aspects, the endocrine therapy and/or at least a second anti-cancer therapy are administered simultaneously. In certain aspects, the endocrine therapy is administered prior to the at least a second anti-cancer therapy. In some aspects, the patient is human.

In a further embodiment, there is provided a method for determining the tumoral sensitivity of a subject with breast cancer comprising: (a) determining the expression level of a set of estrogen receptor (ER)- and progesterone receptor (PR)-related genes in a sample; and (b) calculating an index of sensitivity to endocrine therapy ($SET_{ER/PR}$ index) based on the ER- and PR-related gene expression.

In some aspects, calculating the $SET_{ER/PR}$ index comprises normalizing the expression of the set of ER- and PR-related genes to a set of reference genes. In certain aspects, calculating is further defined as the difference between the average expression of the set of ER- and PR-related genes and the average expression of the set of reference genes. In some aspects, the method further comprises the addition of an optimizing constant. In particular aspects, the optimizing constant has a value of 2. In some aspects, a $SET_{ER/PR}$ index greater than 0 identifies a patient as sensitive to endocrine therapy. In certain aspects, a $SET_{ER/PR}$ index greater than 0.5 identifies a patient as sensitive to endocrine therapy. In some aspects, a $SET_{ER/PR}$ index greater than 1 identifies a patient as sensitive to endocrine therapy.

In certain aspects, the set of ER- and PR-related genes comprises at least 10 of the genes selected from the group consisting of SLC39A6, STC2, CA12, ESR1, PDZK1, NPY1R, CD2, MAPT, QDPR, AZGP1, ABAT, ADCY1, CD3D, NAT1, MRPS30, DNAJC12, SCUBE2, and KCNE4. In some aspects, the set of ER- and PR-related genes comprises at least 11, 12, 13, 14, 15, 16 or 17 of the genes selected from the group consisting of SLC39A6, STC2, CA12, ESR1, PDZK1, NPY1R, CD2, MAPT, QDPR, AZGP1, ABAT, ADCY1, CD3D, NAT1, MRPS30, DNAJC12, SCUBE2, and KCNE4. In some aspects, the set of ER- and PR-related genes consists of SLC39A6, STC2, CA12, ESR1, PDZK1, NPY1R, CD2, MAPT, QDPR, AZGP1, ABAT, ADCY1, CD3D, NAT1, MRPS30, DNAJC12, SCUBE2, and KCNE4.

In some aspects, the set of reference genes comprises at least 5 of the genes selected from the group consisting of LDHA, ATP5J2, VDAC2, DARS, UCP2, UBE2Z, AK2, WIPF2, APPBP2, and TRIM2. In certain aspects, the set of reference genes comprises at least 6, 7, 8 or 9 of the genes selected from the group consisting of LDHA, ATP5J2, VDAC2, DARS, UCP2, UBE2Z, AK2, WIPF2, APPBP2, and TRIM2. In some aspects, the set of reference genes consists of LDHA, ATP5J2, VDAC2, DARS, UCP2, UBE2Z, AK2, WIPF2, APPBP2, and TRIM2.

In certain aspects, the breast cancer is metastatic breast cancer. In some aspects, the breast cancer is Stage II, Stage III or Stage IV breast cancer. In certain aspects, the breast cancer is hormone receptor positive. In some aspects, the hormone receptor is ER and/or PR. In certain aspects, the breast cancer has essentially normal expression of HER2.

In some aspects, the endocrine therapy comprises selective estrogen receptor modulation (SERM), aromatase inhibition (AI), or selective estrogen receptor degradation (SERD) class of treatment. In some aspects, the SERM therapy comprises tamoxifen or toremifene. In certain aspects, the aromatase inhibitor therapy comprises letrozole, anastrozole or exemestane. In some aspects, the SERD therapy comprises fulvestrant.

In certain aspects, the sample is blood, saliva, urine, cytology sample, tissue biopsy, or surgically resected tissue. In some aspects, the sample is blood. In certain aspects, the tissue biopsy is further defined as formalin-fixed and paraffin-embedded (FFPE). In some aspects, the tissue biopsy is further defined as a tumor biopsy. In certain aspects, the cytology sample or tumor biopsy is preserved by flash freezing or an RNA stabilization agent. In some aspects, the cytology sample is preserved in an alcohol-based fixative, either as cells preserved on a glass slide or in solution.

In some aspects, step (a) comprises isolating RNA from the sample. In certain aspects, determining the expression level comprises performing reverse transcription-quantitative real-time PCR (RT-qPCR), microarray analysis, or RNA sequencing. In some aspects, determining the expression level comprises direct hybridization to a template, such as Nanostring® assay or Quantigene assay, or RNAse protection assay.

In some aspects, the subject has previously been administered an anti-cancer therapy. In certain aspects, the anti-cancer therapy is chemotherapy and/or endocrine therapy.

In some aspects, the subject exhibited sensitivity to the chemotherapy and/or endocrine therapy. In certain aspects, the chemotherapy is taxane and/or anthracycline chemotherapy. In some aspects, the anti-cancer therapy was administered for at least 5 years.

In certain aspects, step (b) further comprises detecting the proportion of transcript that contains a mutation in the ESR1 gene. In some aspects, the proportion is calculated as the expression of mutated ESR1 over the expression of the wild-type ESR1. In certain aspects, the mutation in the ESR1 gene is S463P, V534E, P535H, L536Q, L536R, Y537C, Y537S, Y537N, or D538G.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

Agilent 44K V2 microarray platform. (A,C) Calibration cohort of primary breast cancers to calibrate $SET_{ER/PR}$ index from U133A in FF sample to Agilent 44K V2 arrays using FF sample (A) or FFPE sample (C) using linear regression. (B,D) Validation cohort of primary breast cancers to test the calibrated $SET_{ER/PR}$ index using the Agilent 44K V2 arrays with FF sample (B) or FFPE sample (D).

FIGS. 7A-D: Tests for reproducibility of the $SET_{ER/PR}$ index in primary breast cancers when comparing across assay type and sample type (Translation to RainDance picodroplet targeted RNA Sequencing Assay): Translation of $SET_{ER/PR}$ from fresh-frozen (FF) RNA profiled on Affymetrix U133A microarray to the custom targeted RNA sequencing method using RainDance picodroplet-based Illumina MiSeq RNA-Seq assay (RD). (A,C) Calibration cohort of primary breast cancers to calibrate $SET_{ER/PR}$ index from U133A in FF sample to RD assay using FF sample (A) or FFPE sample (C) using linear regression. (B,D) Validation cohort of primary breast cancers to test the calibrated $SET_{ER/PR}$ index using the RD assay with FF sample (B) or FFPE sample (D).

Figure 8:
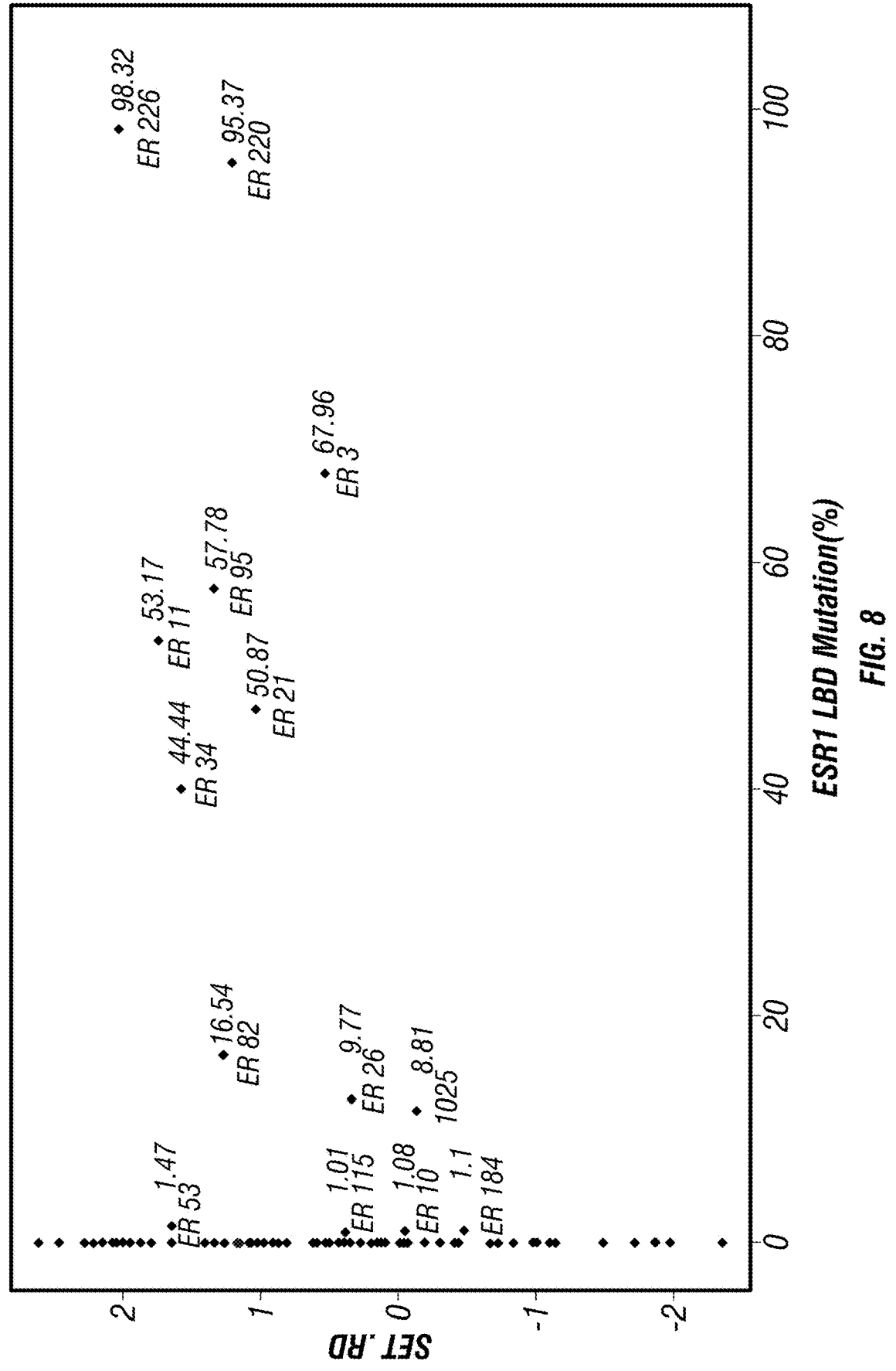
Figure 9A:
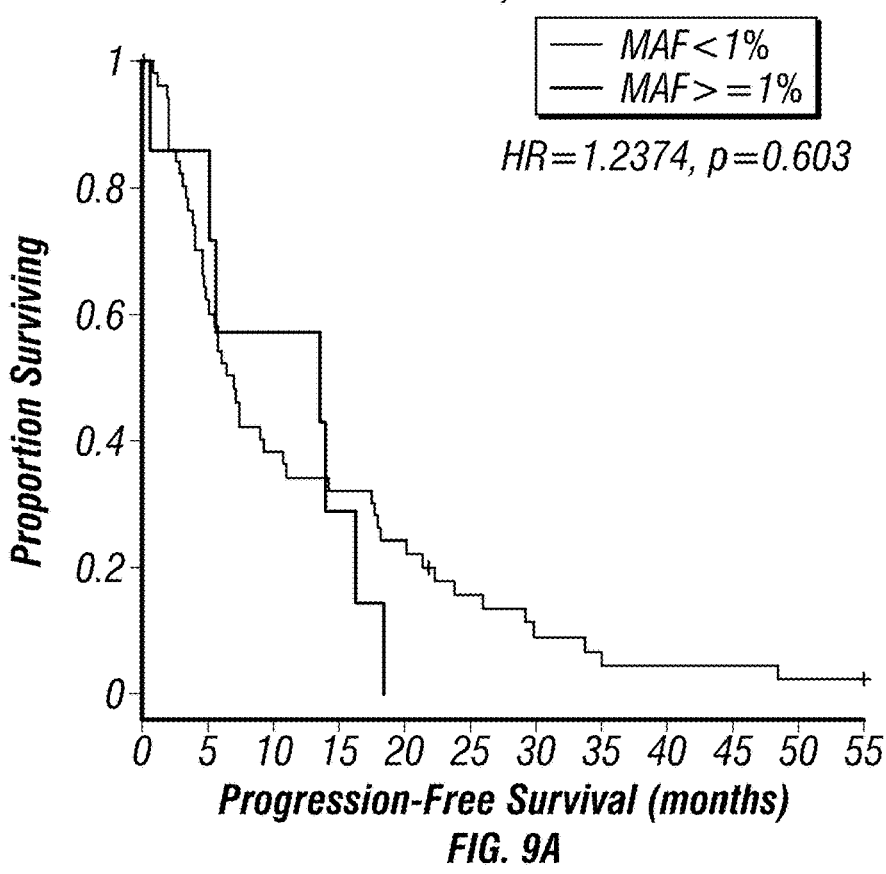
Figure 9B:
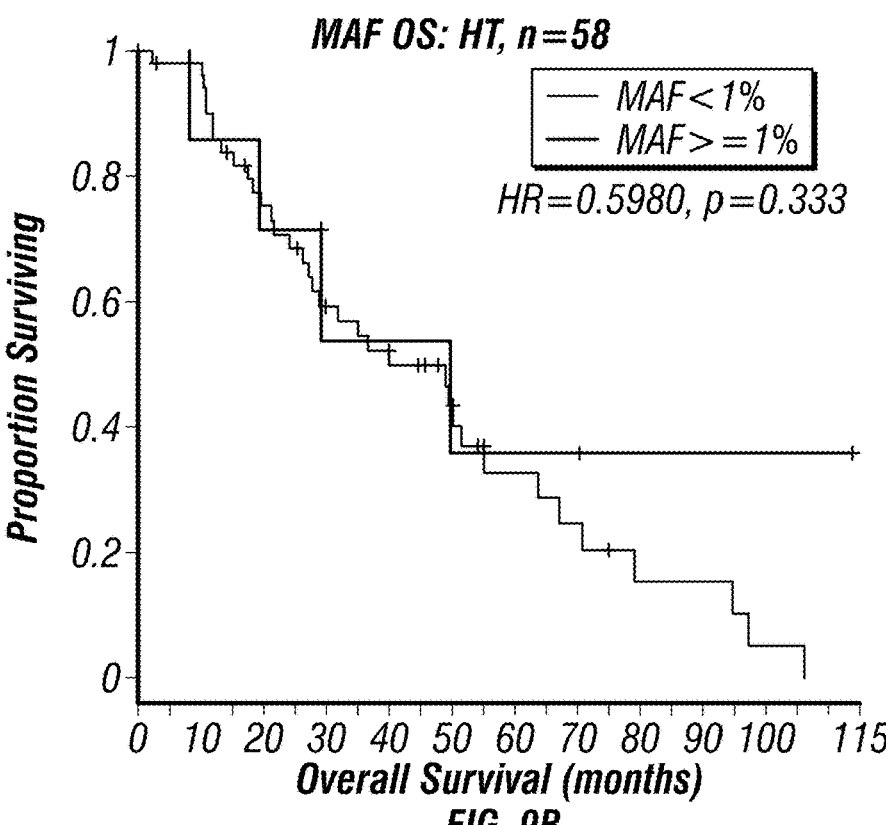
Figure 9C:
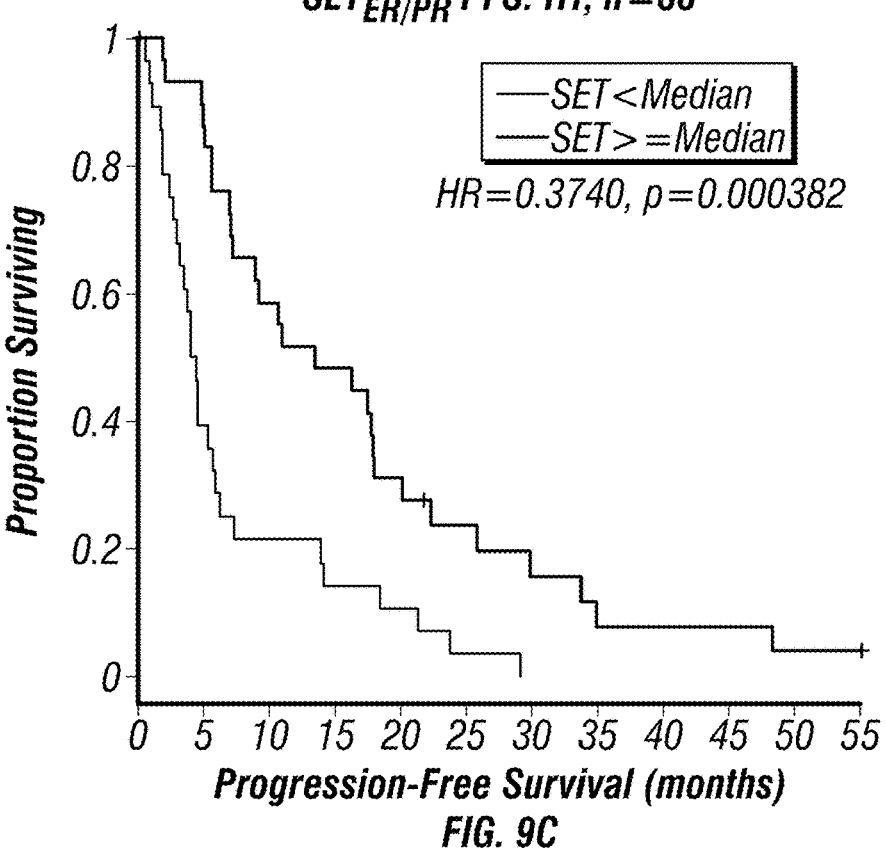
Figure 9D:
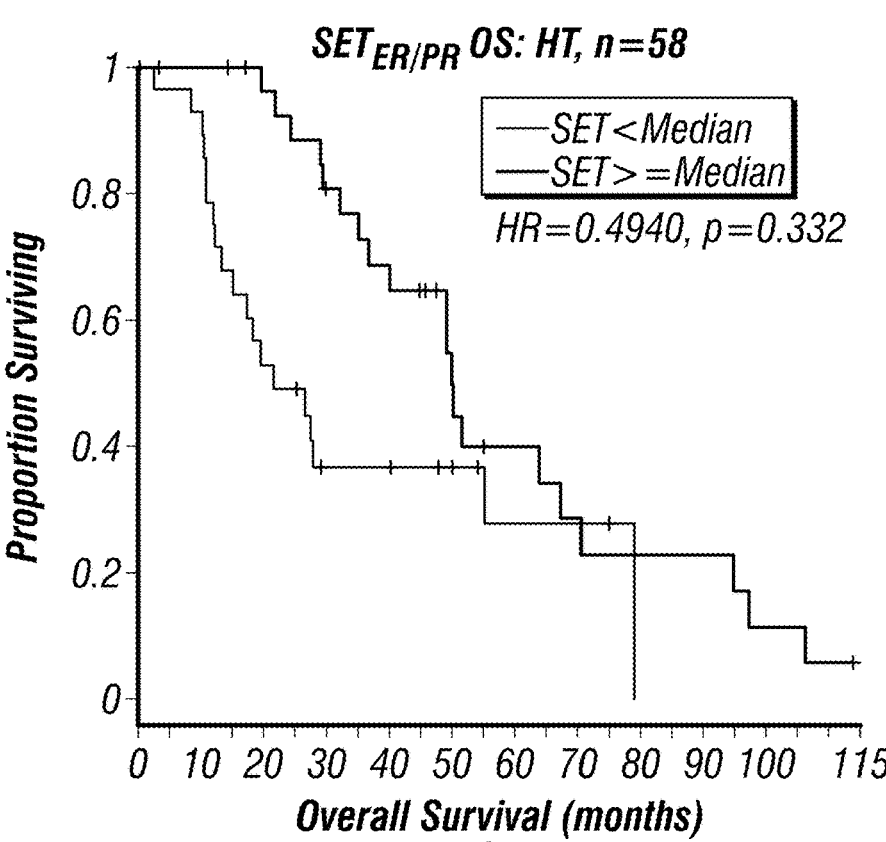
Figure 9E:
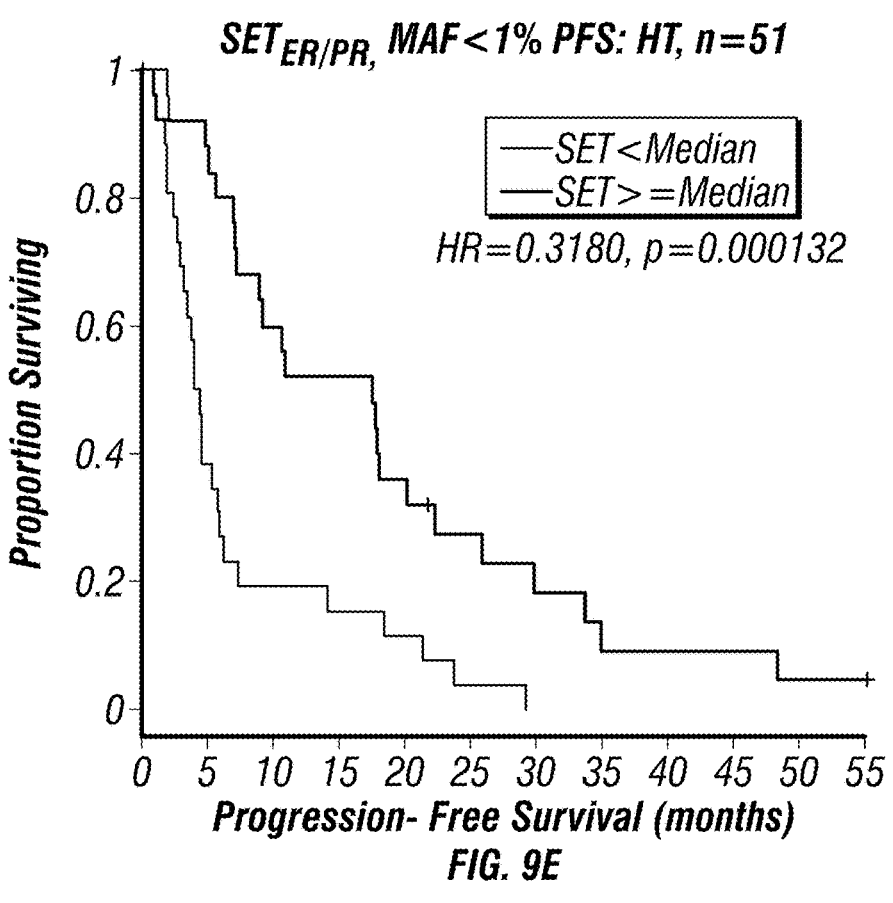
Figure 9F:
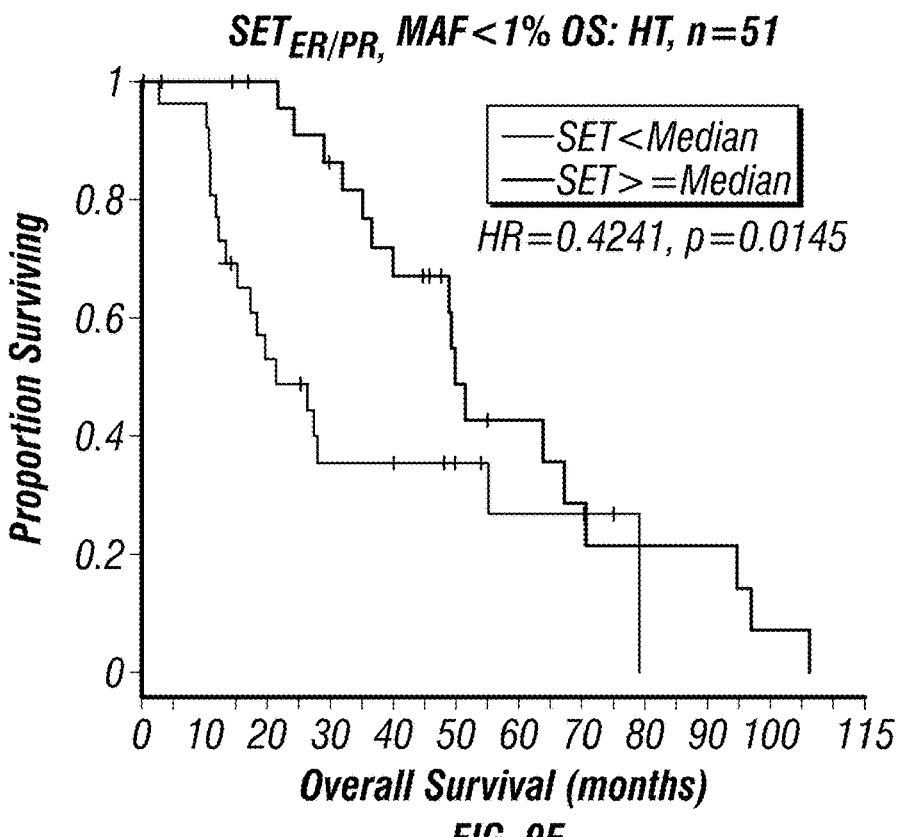

FIG. 8: $SET_{ER/PR}$ index versus Frequency of ESR1 Mutations in Stage IV (Metastatic) Breast Cancer: Targeted needle biopsies from a metastatic site were prospectively obtained from 82 patients with HR$^+$/HER2– breast cancer at the time of any progression event. Purified RNA was subjected to targeted RNA sequencing for the $SET_{ER/PR}$ index genes using the RainDance (RD) platform. ESR1 LBD mutations were identified in 17% (14/82) of metastases (range of mutated transcripts 1%-98%). High frequency mutations (>10% of transcripts) were only observed in metastases with higher $SET_{ER/PR}$ values (above the median).

FIG. 9A-F: Kaplan-Meier plots of survival according to the $SET_{ER/PR}$ index (RD targeted RNA sequencing assay) according to mutation status of ESR1 gene in relapsed metastatic (Stage IV) breast cancer after treatment with hormonal therapy: In patients who next received endocrine therapy (n=58), ESR1 mutation frequency alone did not predict a difference in progression-free survival (A) or overall survival (B). Higher $SET_{ER/PR}$ alone, using the RainDance (RD) assay, predicted longer progression-free (C) and overall survival (D). The predictions were more pronounced in patients without LBD mutation (E and F).

Figure 10:
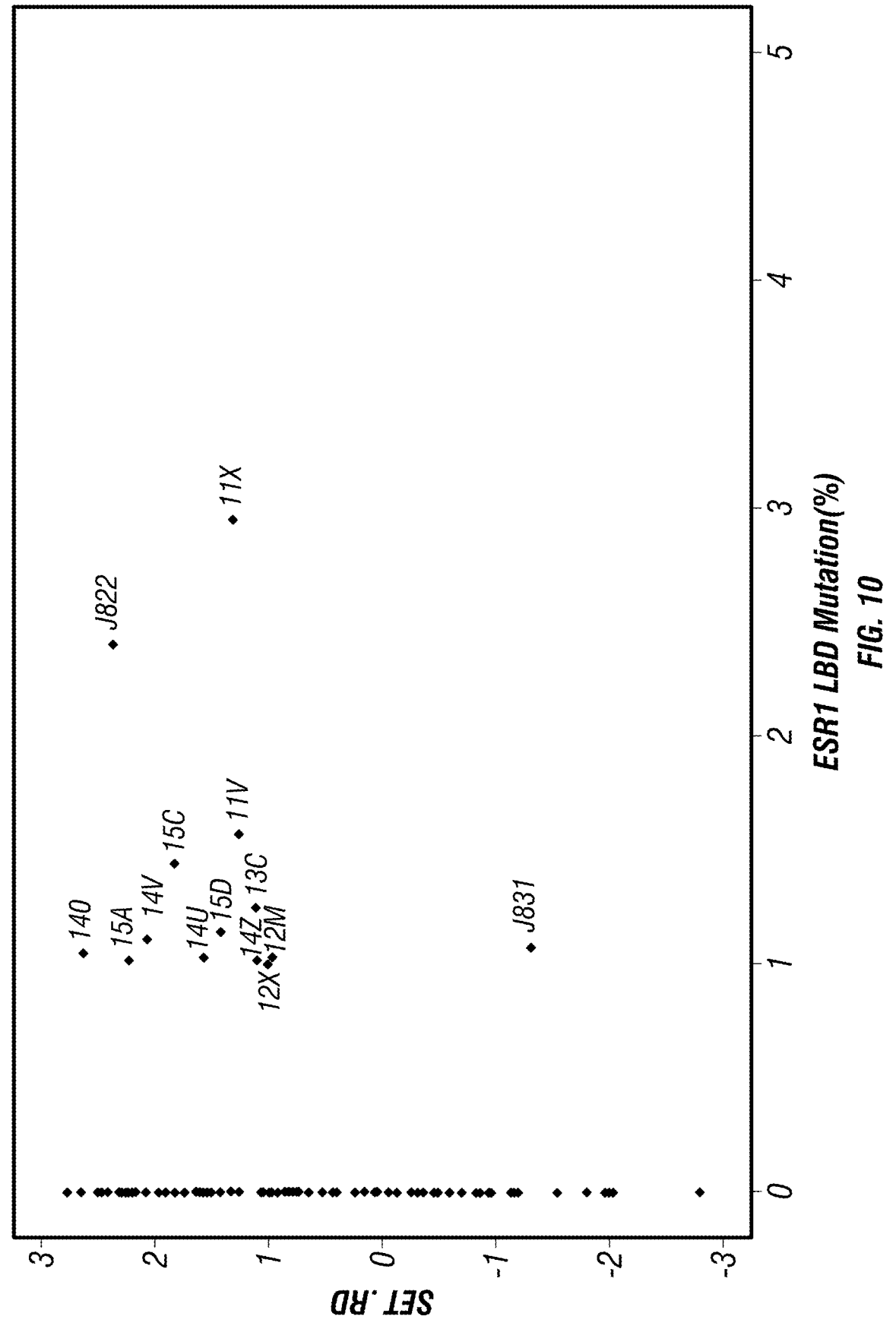

FIG. 10: $SET_{ER/PR}$ index versus Frequency of ESR1 Mutations in Stage II-III (Primary) Breast Cancer: Targeted biopsies from the primary HR$^+$/HER2– breast cancer were prospectively obtained from 95 patients at the time of initial diagnosis. Purified RNA was subjected to targeted RNA sequencing for the $SET_{ER/PR}$ index genes using the Rain-Dance (RD) platform. Rare mutations of the LBD of ESR1 were observed in cancers with higher $SET_{ER/PR}$ index values: in 15% (14/95) of primary cancer samples (range of mutated transcripts 1%-3%).

Figure 11A:
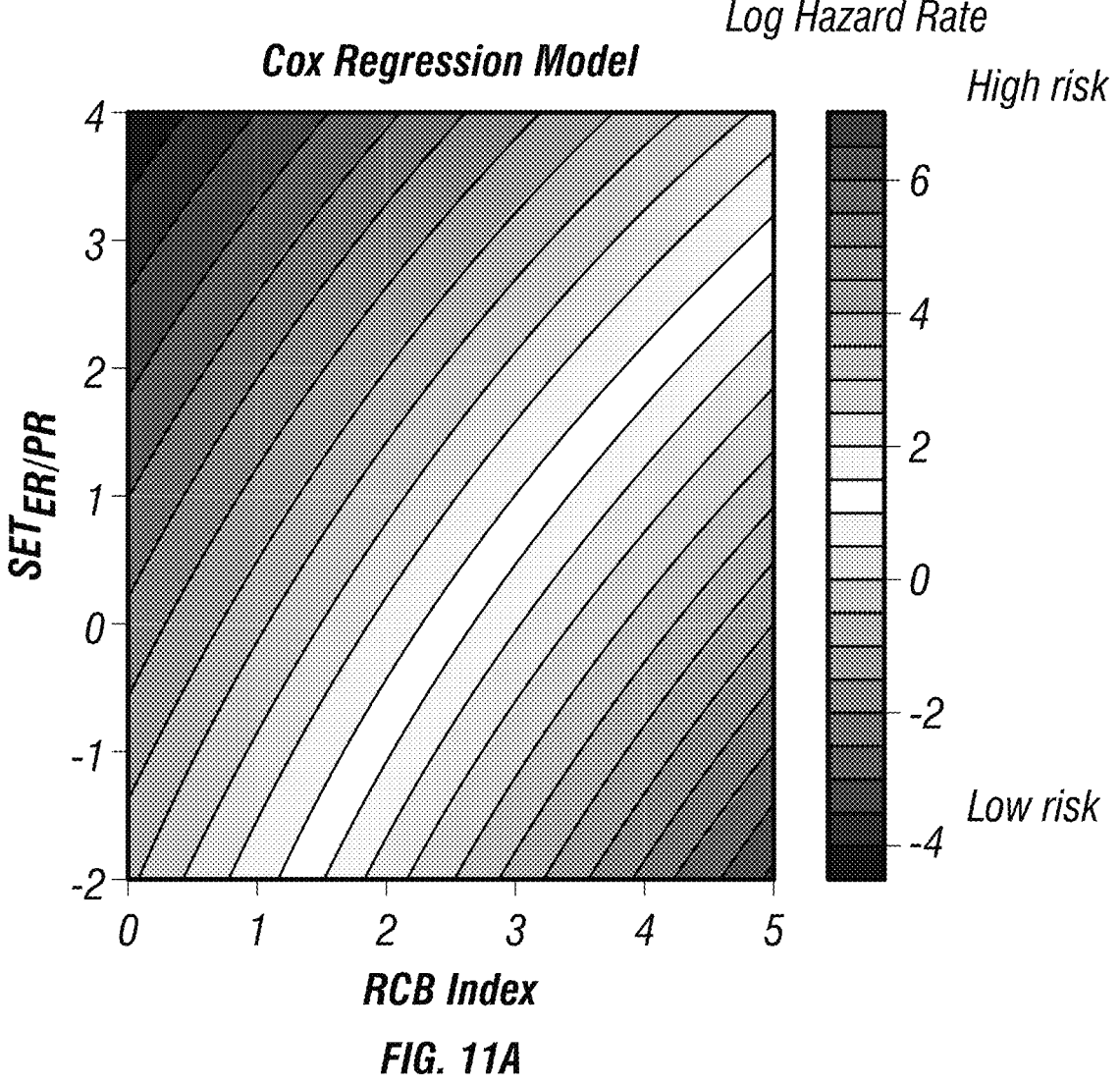
Figure 11B:
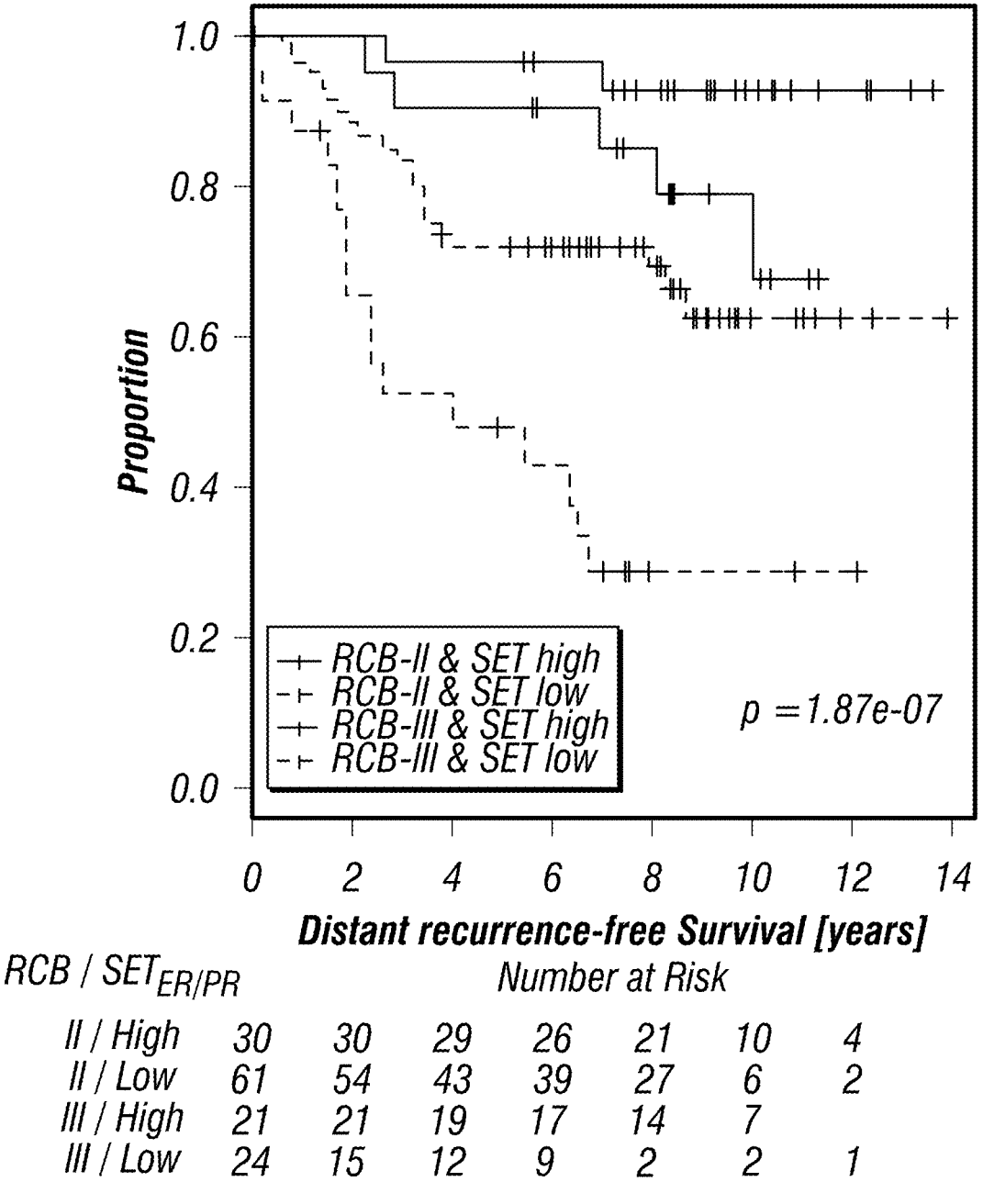

FIGS. 11A-B: Survival according to the $SET_{ER/PR}$ index in Stage II and III breast cancer after treatment with surgery and neoadjuvant chemotherapy (NAC), and prior to treatment with hormonal therapy: The relationship between the $SET_{ER/PR}$ index and the residual cancer burden (RCB) after completion of NAC in patients with clinical Stage II-III HR$^+$/HER2– breast cancer at time of initial diagnosis. (A) The prognostic model for the continuous $SET_{ER/PR}$ index (y-axis) compared to the continuous RCB using coefficients from the multivariable model shown in Table 3. (B) Classes of $SET_{ER/PR}$ index using pre-defined cutpoint of 1.85 to distinguish high $SET_{ER/PR}$ index (solid lines) versus low $SET_{ER/PR}$ index (dashed lines) are shown for patients according to the RCB classes of moderate residual disease or extensive residual disease. $SET_{ER/PR}$ index classes were prognostic for patients with RCB-II and for patients with RCB-III. Excellent prognosis was observed for RCB-II with high $SET_{ER/PR}$ index (solid line).

Figure 12:
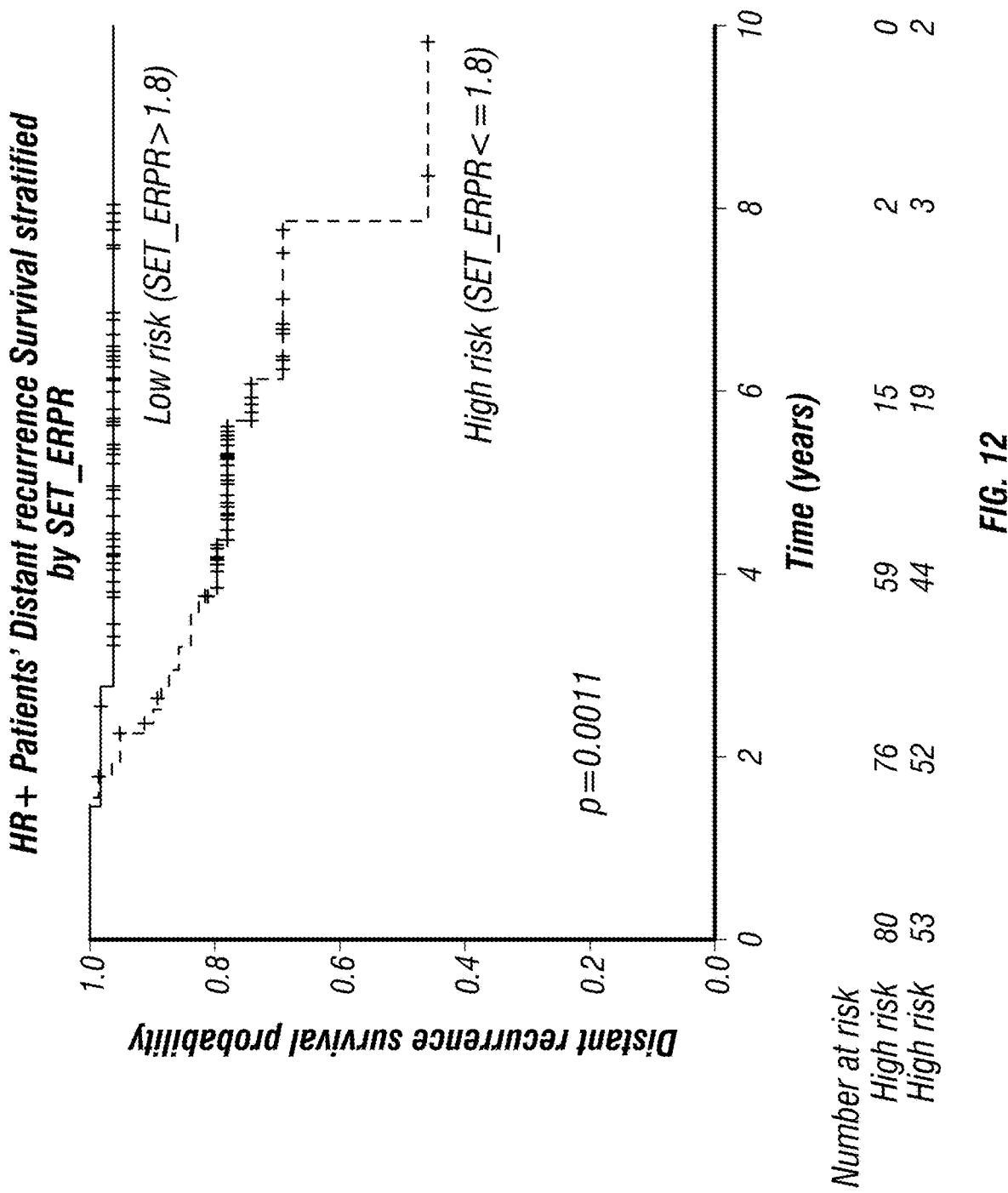
Figure 13A:
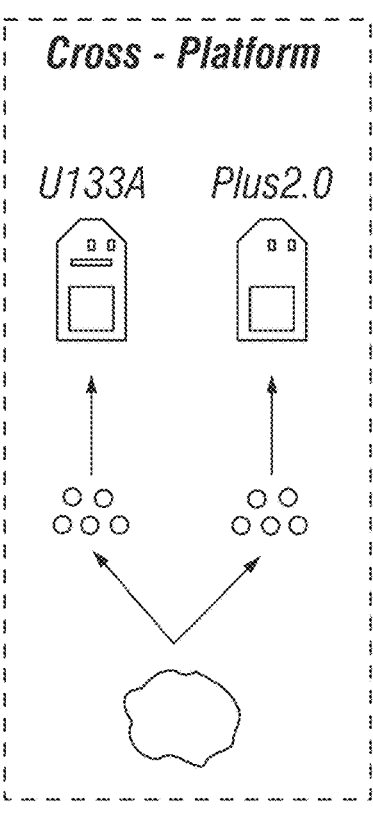
Figure 13B:
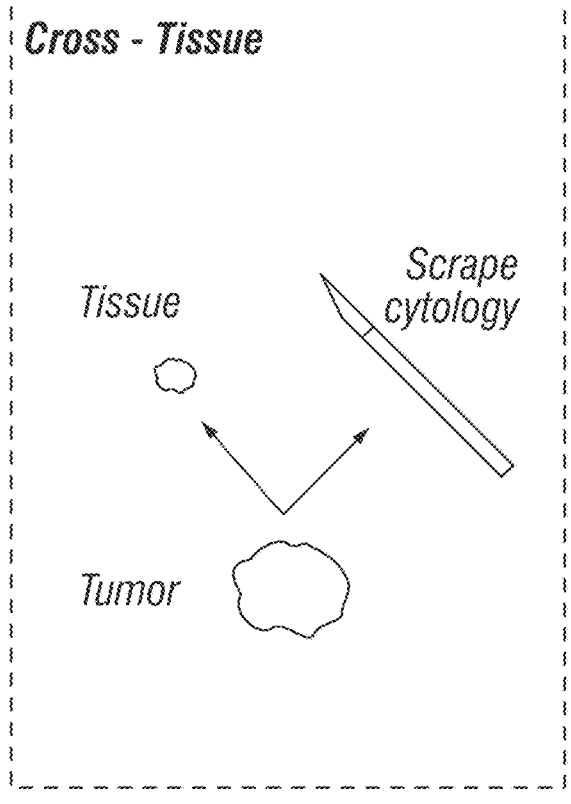
Figure 13C:
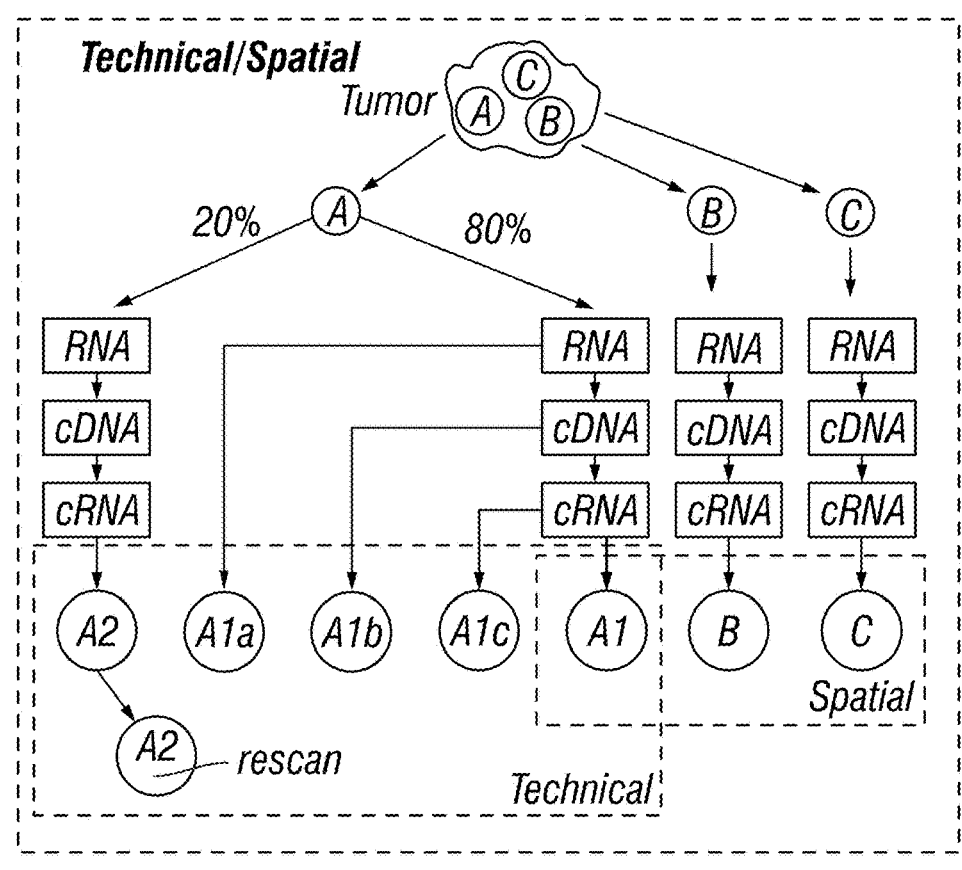
Figure 13D:
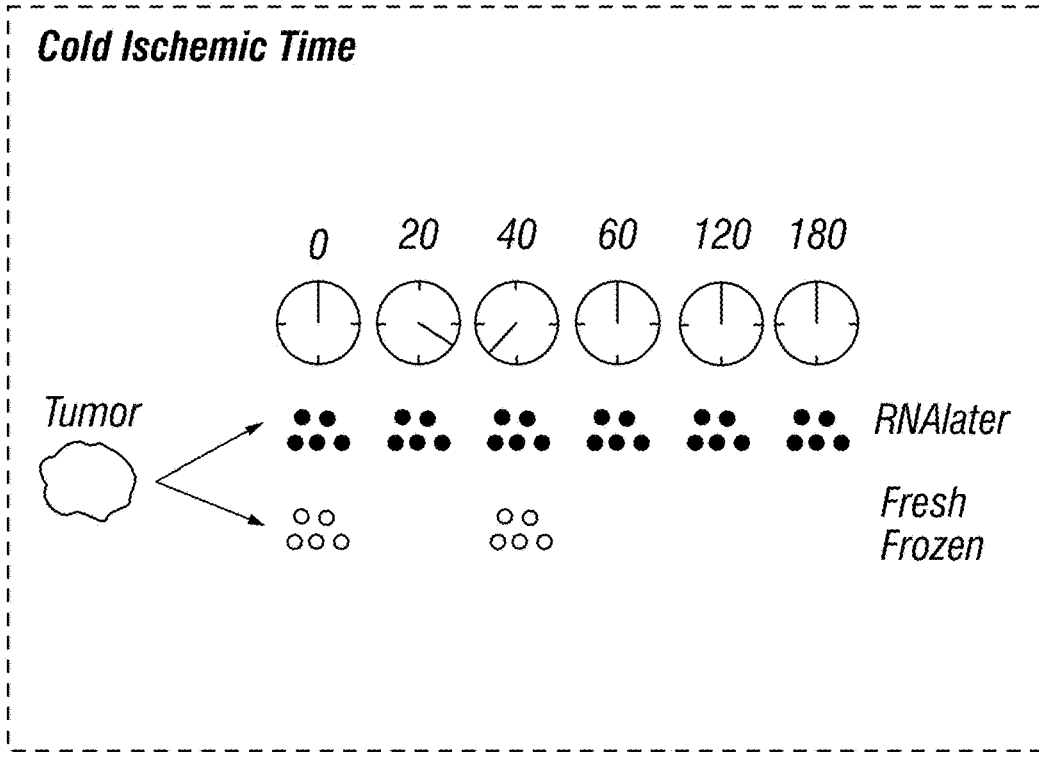
Figure 13E:
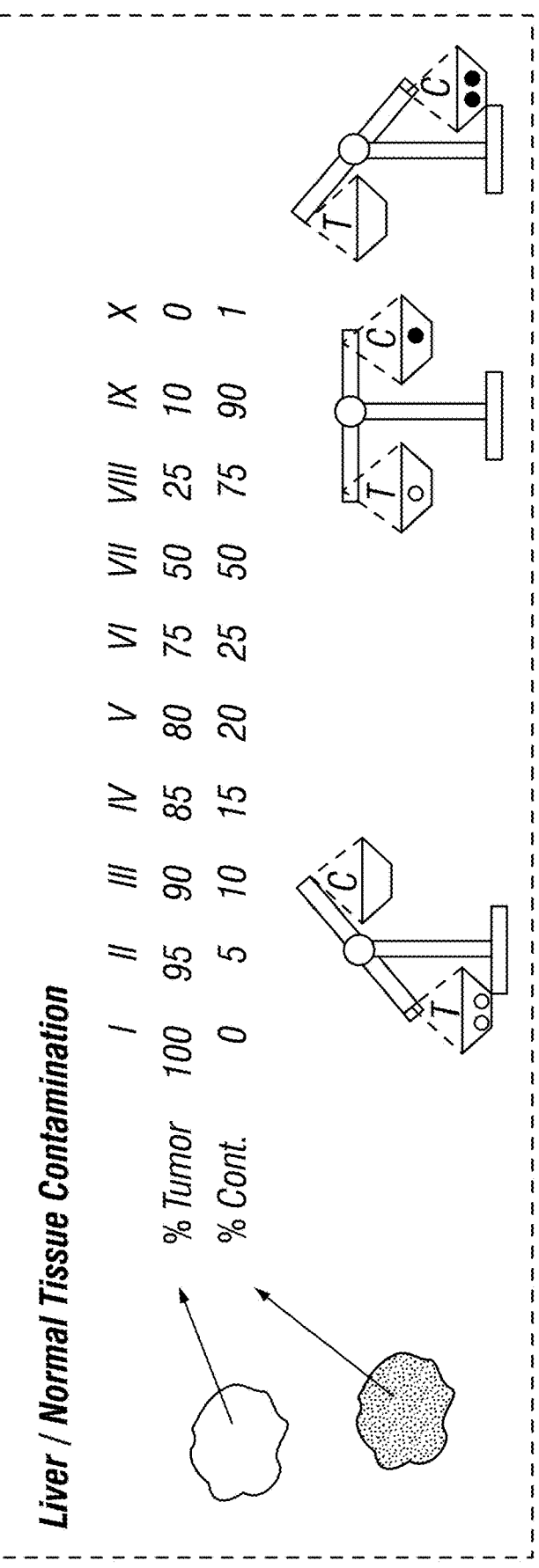

FIG. 12: Survival according to the $SET_{ER/PR}$ index in Stage II and III breast cancer after treatment with surgery, and prior to treatment with chemotherapy and hormonal therapy: Kaplan-Meier plot of the distant relapse-free survival for patients with lymph node-positive HR$^+$/HER2 breast cancer (i.e. Stage II or III) shown for high $SET_{ER/PR}$ index (low-risk), compared to low $SET_{ER/PR}$ index (high-risk). This result was from a blinded and independent external validation study.

FIGS. 13A-E: Pre-analytical and analytical datasets. (A) Inter-assay reproducibility comparing Affymetrix U133A and Plus2.0 microarrays. (B) Inter-sample type reproducibility comparing cytology (scrape) and tissue samples. (C) Intra-assay replicates and intra-tumoral heterogeneity: tissue samples were taken from three different macroscopic tumor areas A, B and C of the same resection specimen to evaluate intra-tumoral heterogeneity. In a subset of cases, the laboratory procedure was repeated at 5 different levels. (D) Influence of cold ischemic delay and sample type: tissue samples of surgical specimens of the same tumors were stored in fixative of were snap frozen with increasing time delay after surgical removal. (E) Contamination with liver and normal tissue: tumor samples were mixed at different ratios with normal breast tissue or liver tissue to evaluate the effect of contamination.

Figure 14A:
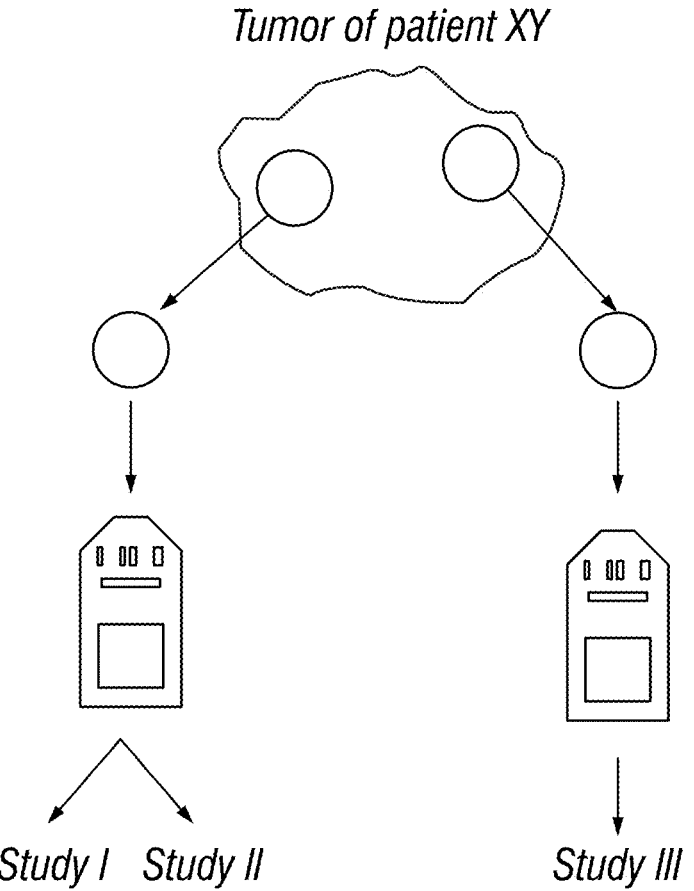
Figure 14B:
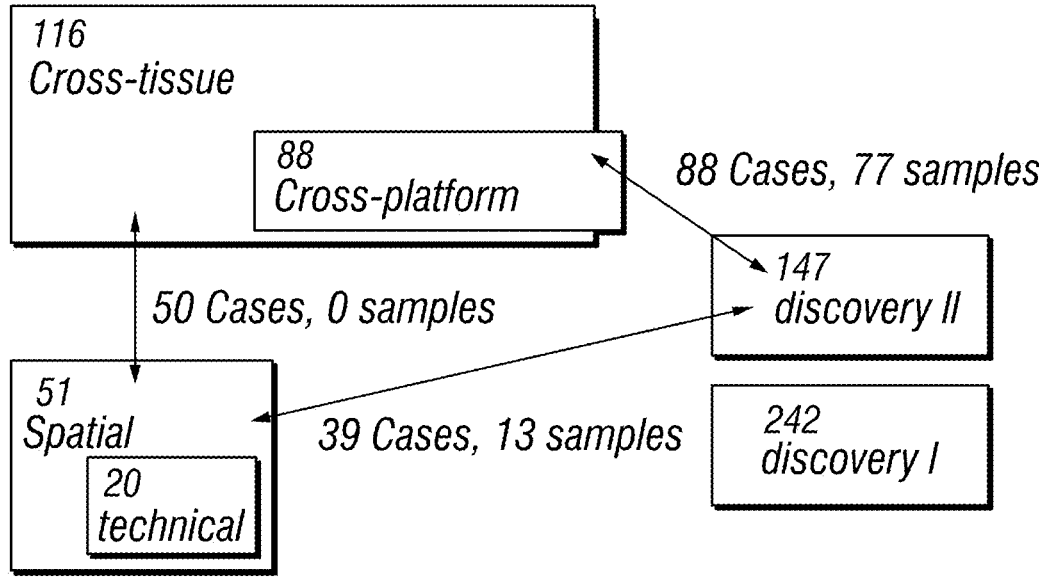

FIGS. 14A-B: (A) Schematic to illustrate the different levels of overlap between the datasets. Study A and B share the same case, tissue sample and array data. Study III shares the same case with study I and II, but an individual sample was taken and processed and profiled individually. (B) Overlap of the different analytical and pre-analytic dataset with samples and/or cases of the discovery dataset.

Figure 15:
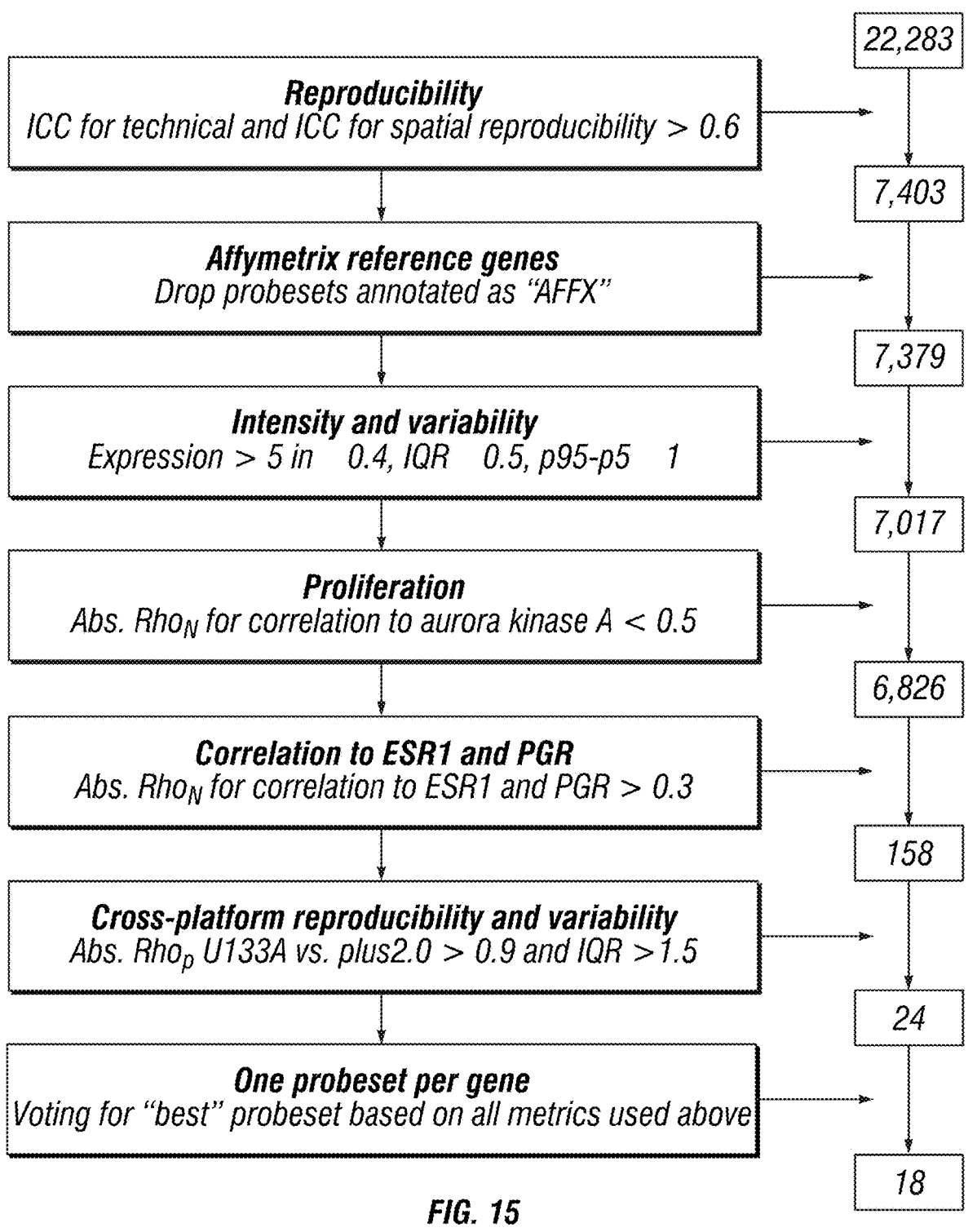

FIG. 15: Selection of the genes with expression levels correlated most strongly and reliably to the expression levels of ESR1 and PGR genes, through a series of technical and biological filtering steps.

Figure 16A:
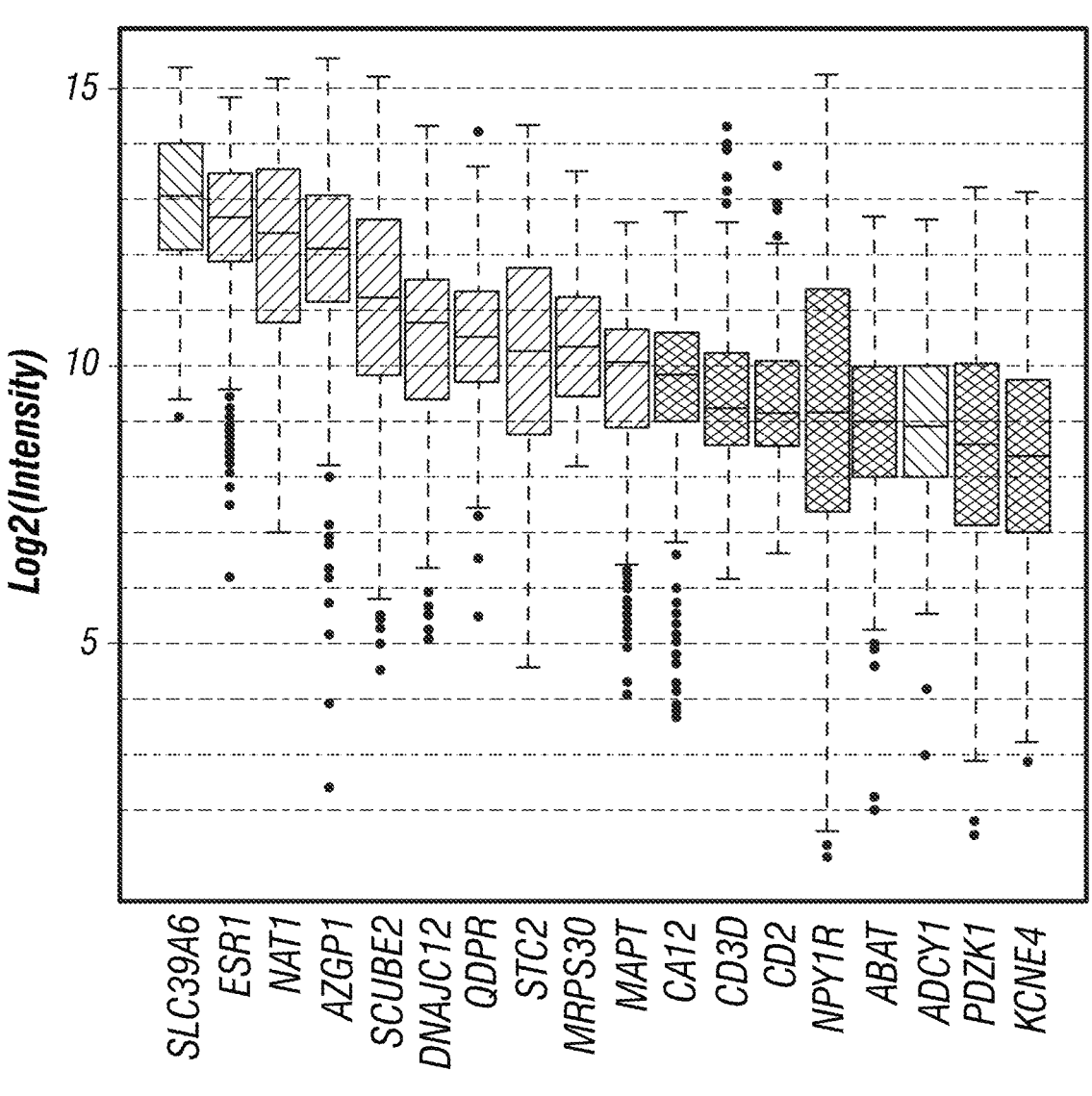
Figure 16B:
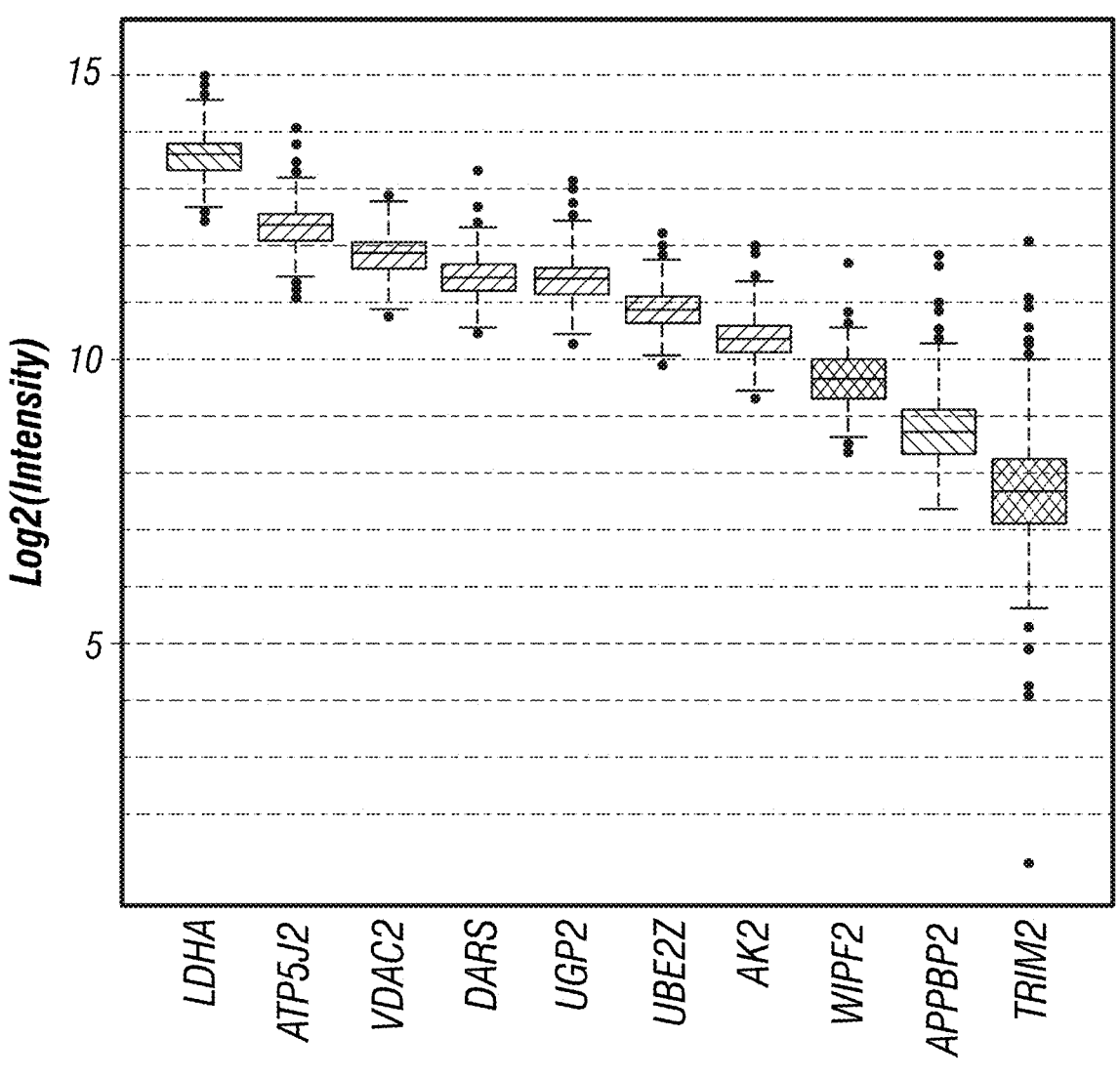

FIGS. 16A-B: Distribution of the ESR1- and PGR-associated genes in the hormone-receptor-positive discovery cohort (A) and the reference genes in the hormone-receptor-positive, HER2-negative subset of the discovery cohort (B).

Figure 17A:
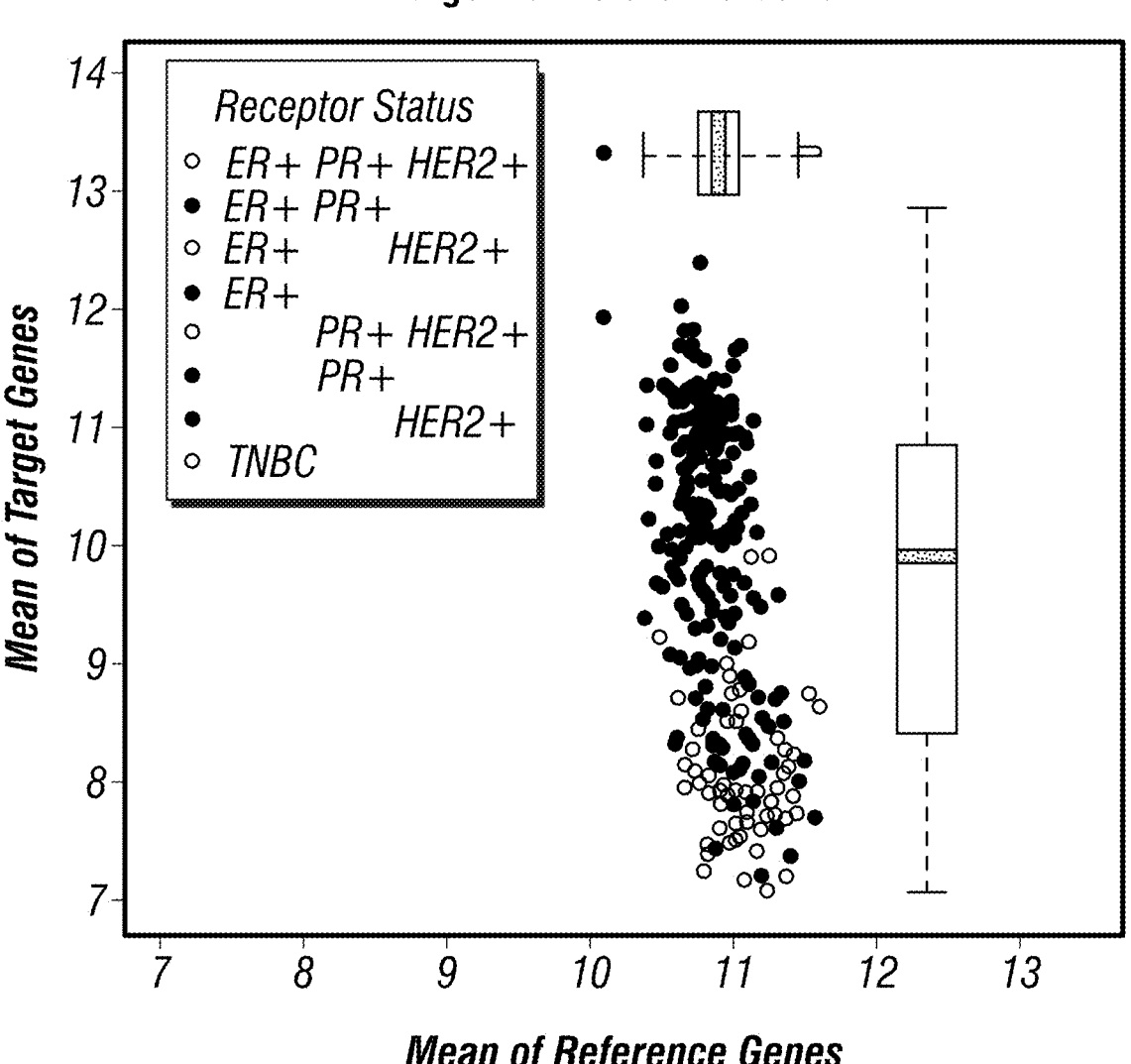
Figure 17B:
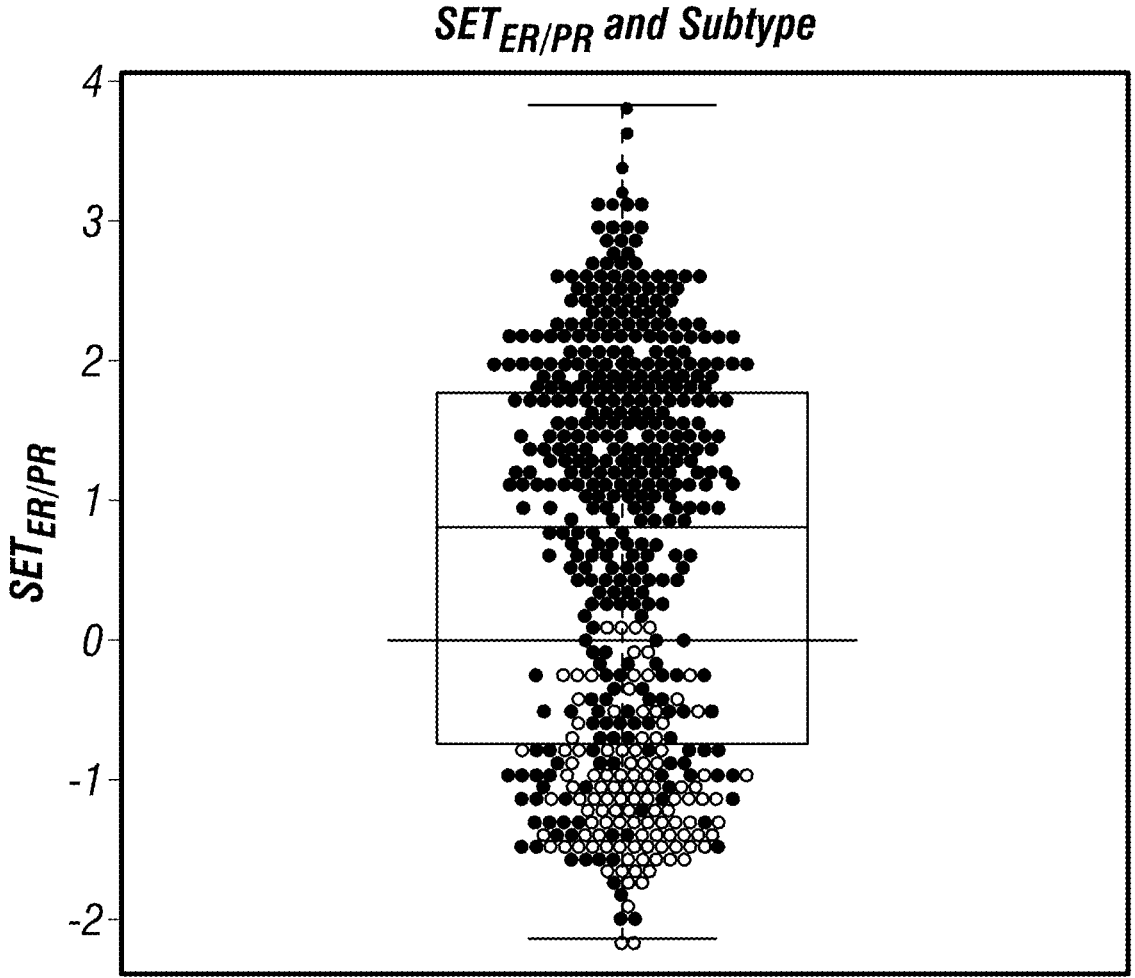

FIGS. 17A-B: (A) Distribution of the target- and reference genes in the discovery dataset. The sum of the target genes is plotted against the sum of the reference genes to illustrate the difference in variation. (B) Using 175 additional hormone receptor-negative cases, the score was scaled linearly to assign negative values to hormone receptor-negative tumors.

Figure 18:
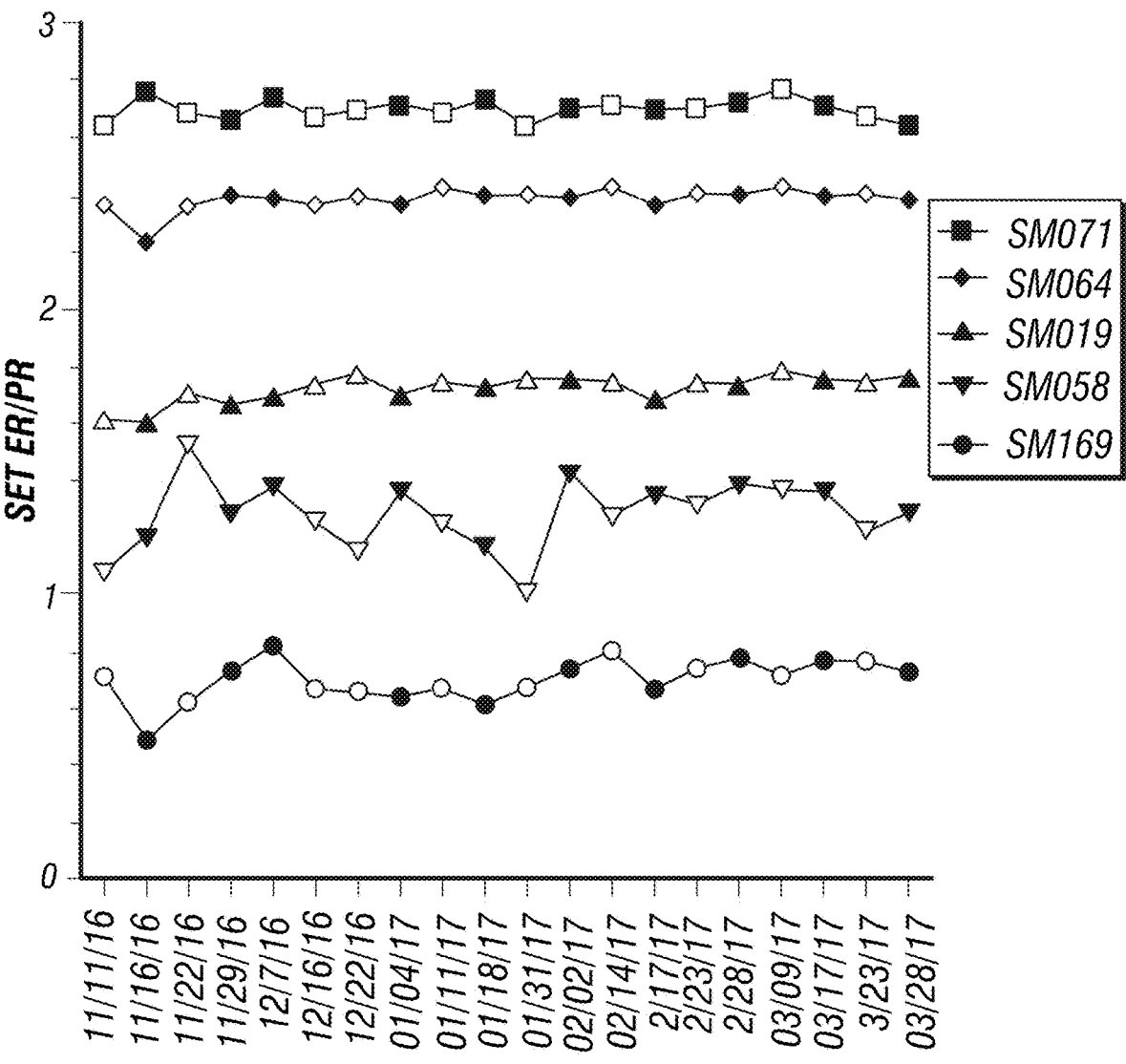

FIG. 18: Reproducibility of $SET_{ER/PR}$ index measurements with FFPE and Quantigene platform over time and different operators, using different lots of reagents. FFPE sections from five different samples were assayed once per week for 20 weeks. Two different operators (as indicated by blue and green data points) performed the assay FIG. 19: Determination of a quality control threshold for $SET_{ER/PR}$ index measurements with FFPE and Quantigene platform. Limiting dilutions of RNA derived from FFPE tissue (125 ng-1.95 ng) were assayed from five primary breast cancers. The measurements were compared with the $SET_{ER/PR}$ index value measured using fresh/frozen RNA profiled on U133A microarray. The absolute deviation of the $SET_{ER/PR}$ index measurement from the U133A measurement is shown against the median reference gene value and a cut off of >4.0 for the median reference gene value was determined to be optimal for quality assessment as pass or fail.

Figure 20A:
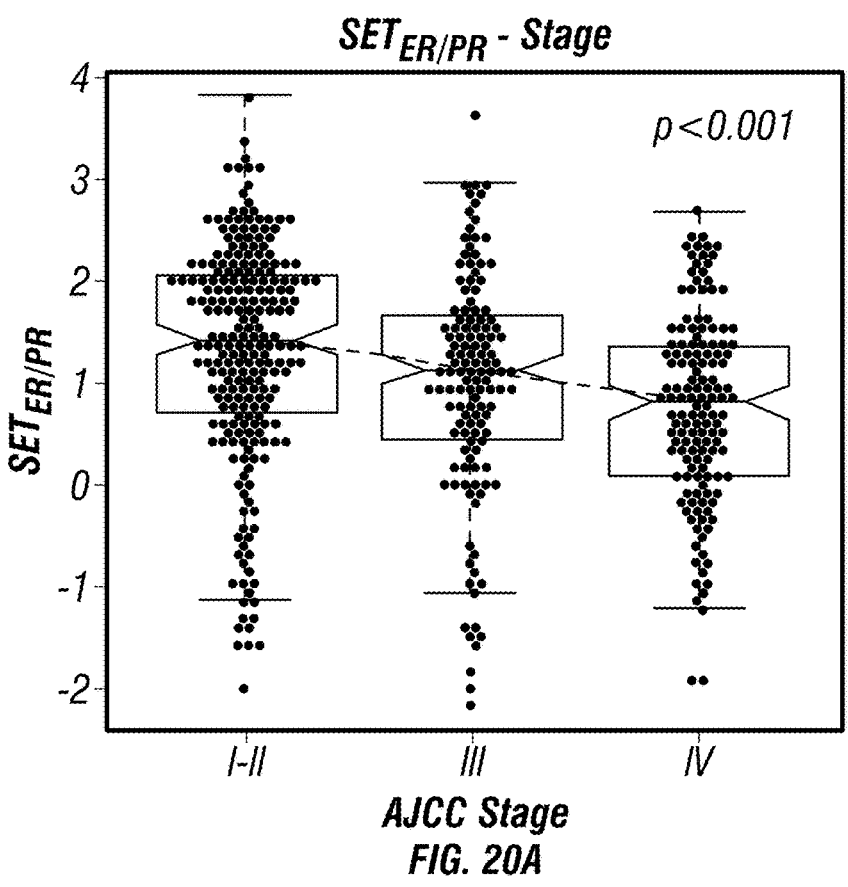
Figure 20B:
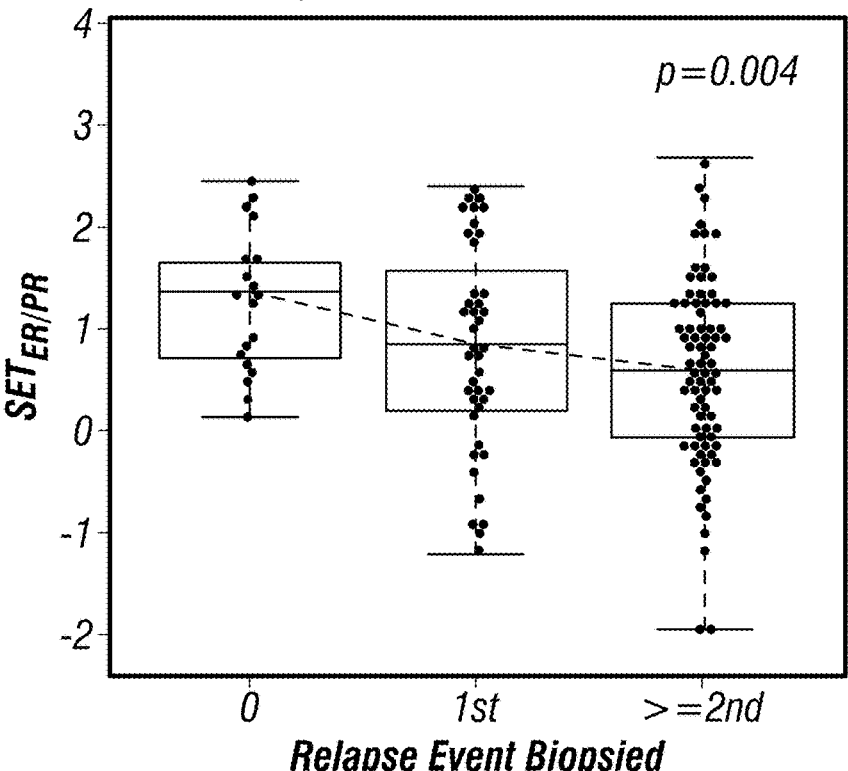

FIGS. 20A-B: (A) $SET_{ER/PR}$ according to stage at diagnosis and (B) according to the number of the biopsied relapse event in patients with metastatic breast cancer.

Figure 21A:
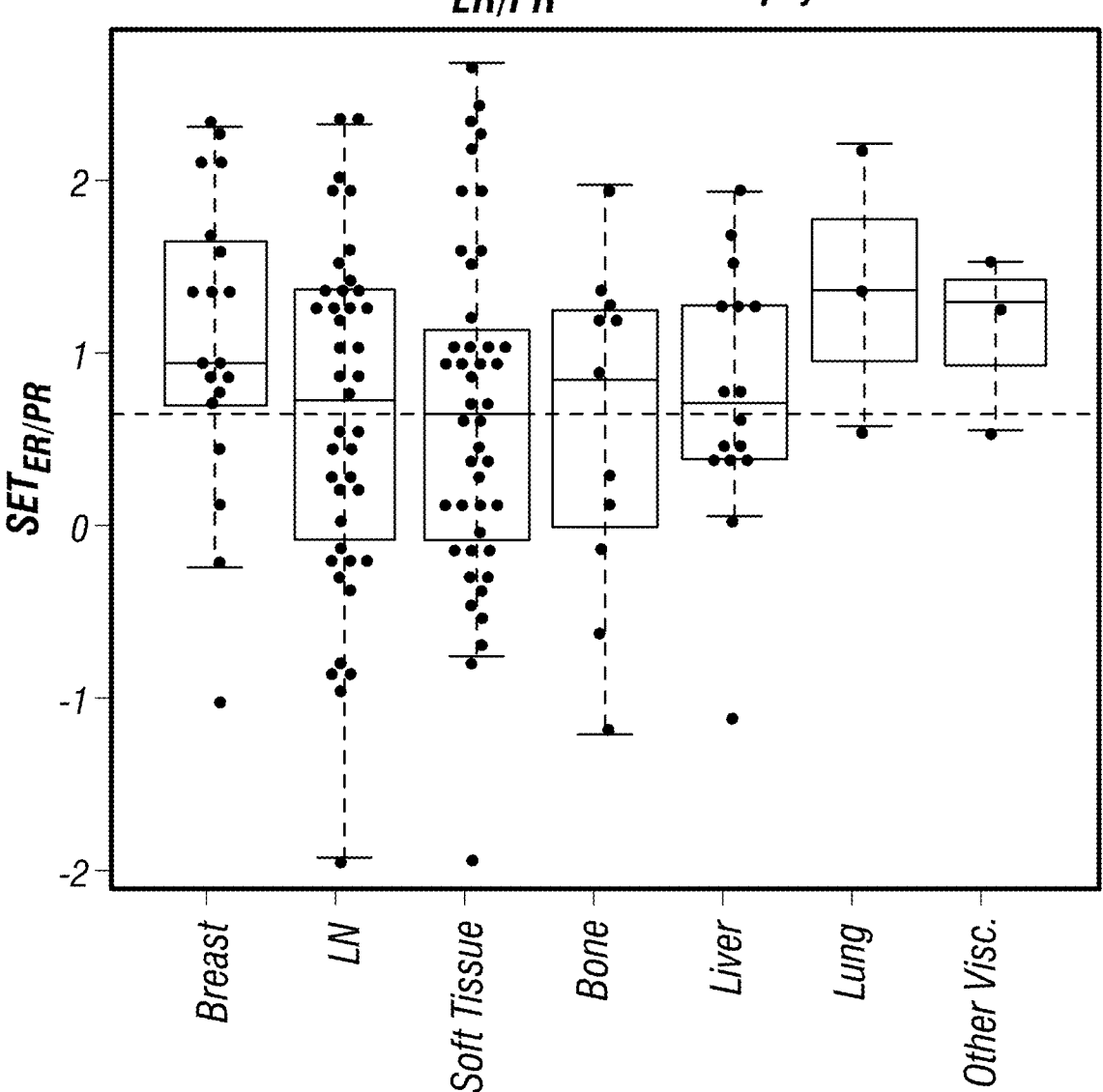
Figure 21B:
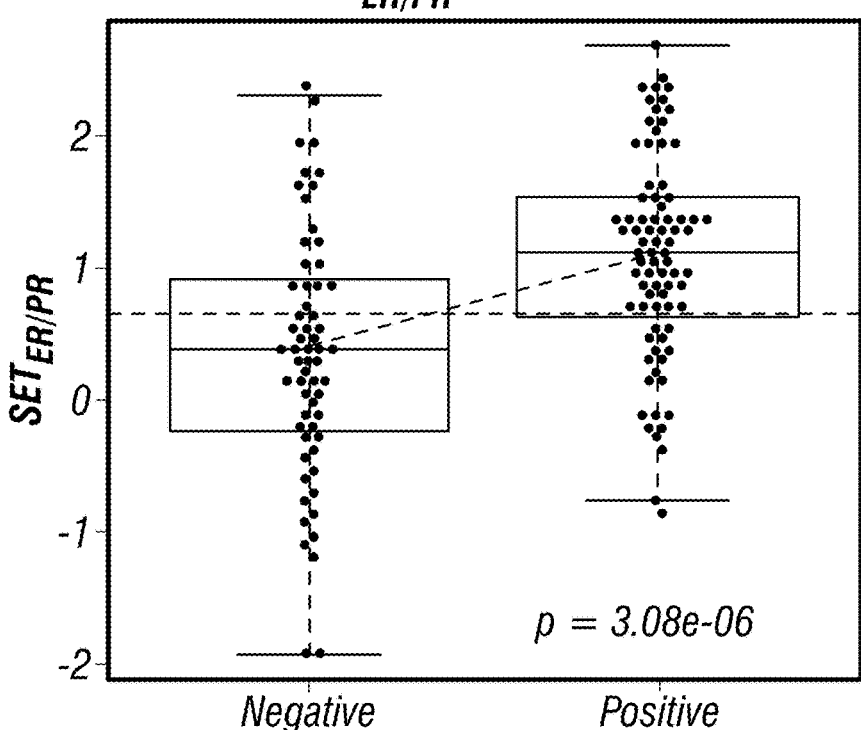
Figure 21C:
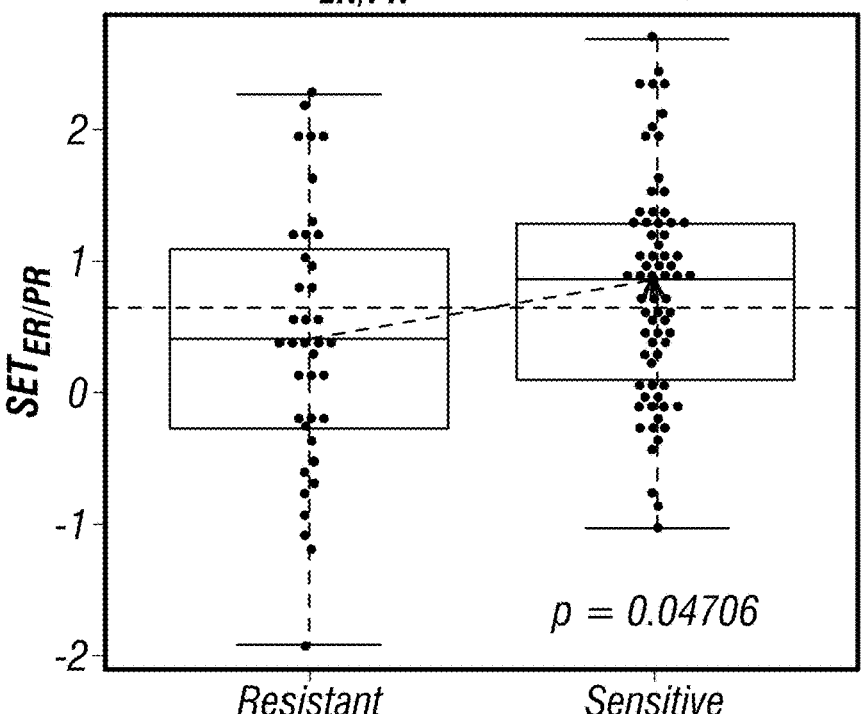

FIGS. 21A-C: $SET_{ER/PR}$ and clinical and pathological tumor characteristics. (A) Site of metastatic breast cancer for protocol biopsy, (B) PGR status by immunohistochemistry and (C) prior sensitivity to endocrine treatment.

Figure 22:
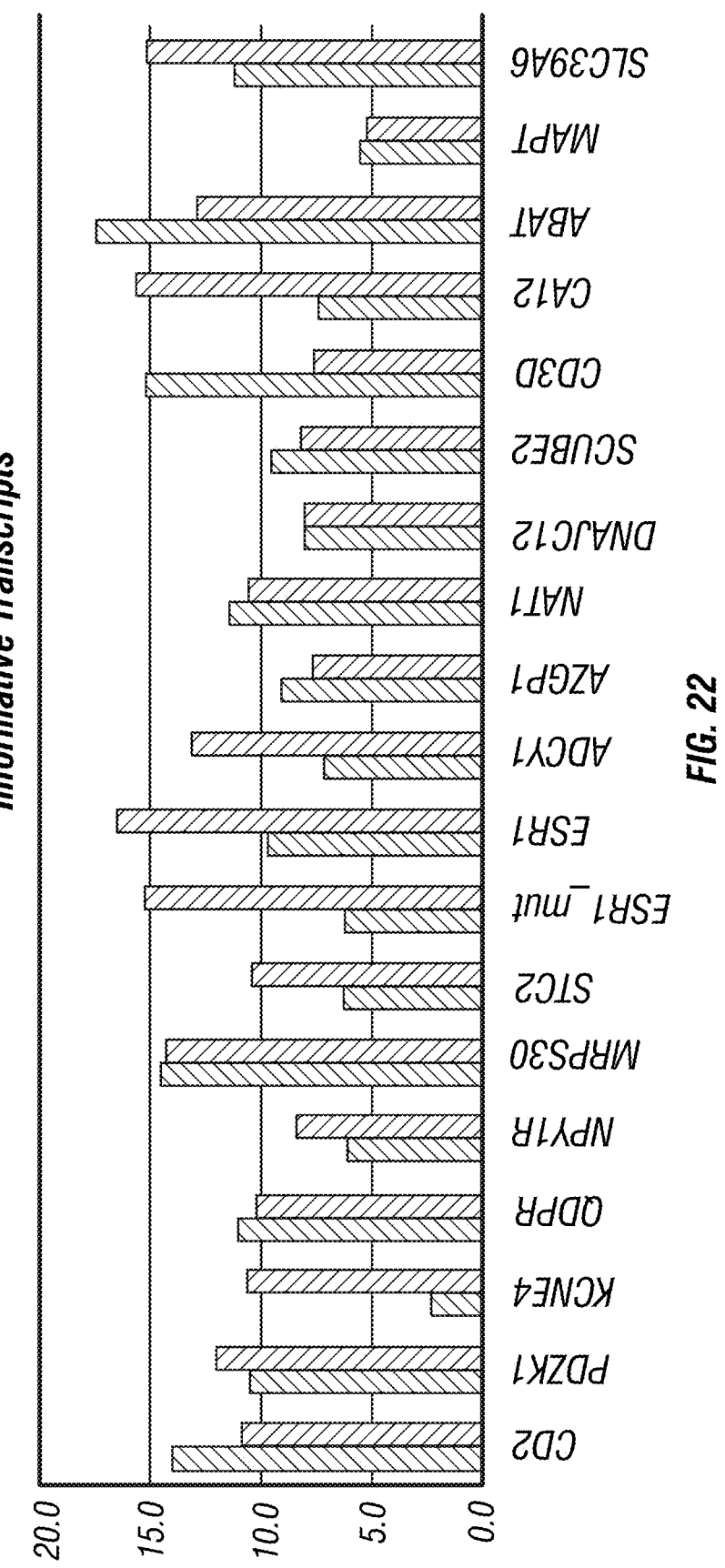
Figure 22:
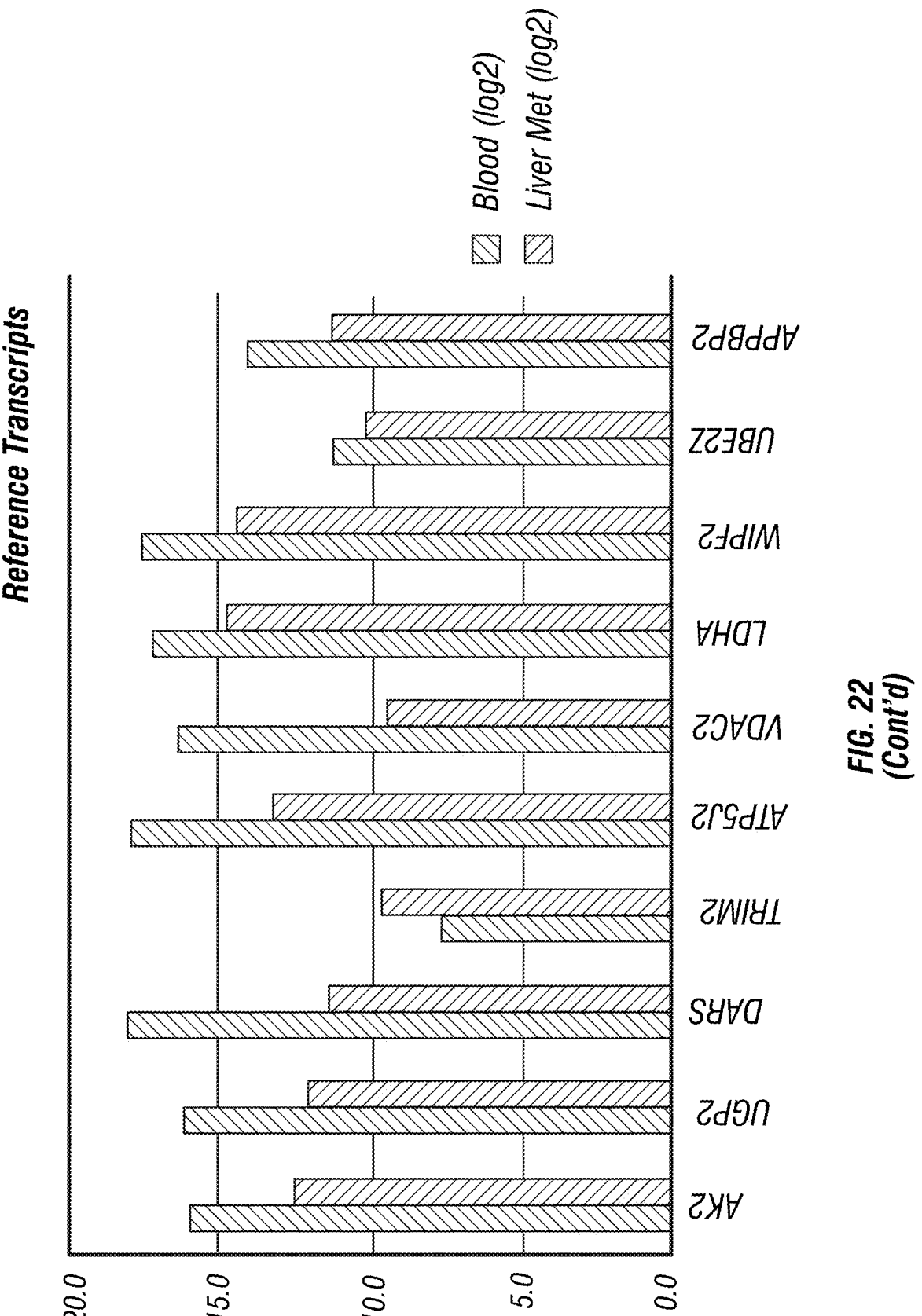

FIG. 22: Expression levels of transcripts used in the $SET_{ER/PR}$ index as measured using our RD method of targeted RNA sequencing of RNA derived from plasma exosomes from peripheral blood sample and from FFPE tumor biopsy of a liver metastasis from the same patient.

DESCRIPTION OF ILLUSTRATIVE EMBODIMENTS

The course of breast cancer therapy usually relies on following a sequence of available endocrine treatments (Barrios et al., 2012; Dodwell et al., 2006), unless a symptomatic disease burden or more rapidly progressive disease favors a switch to chemotherapy (Giordano et al., 2014; Cardoso et al., 2014; Beslija et al., 2007). However, the treatment strategy increasingly requires nuanced clinical judgment as the selection of treatment options continues to expand to include additional endocrine treatments, chemotherapy treatments, and other molecular targeted approaches. Accordingly, the present disclosure overcomes challenges associated with current technologies by providing an index of tumoral sensitivity to endocrine therapy, referred to herein as the $SET_{ER/PR}$ index.

The $SET_{ER/PR}$ index is calculated using the expression level of a combination of genes related to both the estrogen receptor (ER) gene (ESR1) and the progesterone receptor (PR) gene (PGR), such as disclosed in Table 5. In some embodiments, the $SET_{ER/PR}$ index is used to predict the sensitivity of breast cancer, particularly metastatic breast cancer, to endocrine therapy alone or in combination with other therapies. Thus, further embodiments include methods of treating breast cancers identified to be sensitive to endocrine therapy using the $SET_{ER/PR}$ index by administering a endocrine therapy to the patient.

The $SET_{ER/PR}$ index was validated using a prospective cohort of needle biopsy samples from metastases of hormone receptor-positive breast cancer (stored in RNA preservative then profiled using Affymetrix U133A gene expression arrays) that were annotated with clinical, treatment, and survival information. Further experiments were performed to estimate the reproducibility of the gene expression measurements under the effects of intratumoral heterogeneity, technical repetition, different microarray platforms, and different types of tumor biopsies, in order to develop the technically robust customized assay provided herein.

I. DEFINITIONS

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a hormonal therapy.

"Subject" and "patient" refer to either a human or non-human, such as primates, mammals, and vertebrates. In particular embodiments, the subject is a human.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

"Prognosis" refers to as a prediction of how a patient will progress, and whether there is a chance of recovery. "Cancer prognosis" generally refers to a forecast or prediction of the probable course or outcome of the cancer. As used herein, cancer prognosis includes the forecast or prediction of any one or more of the following: duration of survival of a patient susceptible to or diagnosed with a cancer, duration of recurrence-free survival, duration of progression-free survival of a patient susceptible to or diagnosed with a cancer, response rate in a group of patients susceptible to or diagnosed with a cancer, duration of response in a patient or a group of patients susceptible to or diagnosed with a cancer, and/or likelihood of metastasis and/or cancer progression in a patient susceptible to or diagnosed with a cancer. Prognosis also includes prediction of favorable survival following cancer treatments, such as a conventional cancer therapy.

An "anti-cancer" agent is capable of negatively affecting a cancer cell/tumor in a subject, for example, by promoting killing of cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

The term "antibody" herein is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

The term "unit dose" or "dosage" refers to physically discrete units suitable for use in a subject, each unit containing a predetermined quantity of the therapeutic composition calculated to produce the desired responses discussed above in association with its administration, i.e., the appropriate route and treatment regimen. The quantity to be administered, both according to number of treatments and unit dose, depends on the effect desired. The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. For example, a dose may also comprise from about 1 µg/kg/body weight to about 1000 mg/kg/body weight (this such range includes intervening doses) or more per administration, and any range derivable therein. In non-limiting examples of a derivable range from the numbers listed herein, a range of about 5 µg/kg/body weight to about 100 mg/kg/body weight, about 5 µg/kg/body weight to about 500 mg/kg/body weight, etc., can be administered. The practitioner responsible for administration will, in any event, determine the concentration of active ingredient(s) in a composition and appropriate dose(s) for the individual subject.

The term "immune checkpoint" refers to a molecule such as a protein in the immune system which provides inhibitory signals to its components in order to balance immune reactions. Known immune checkpoint proteins comprise CTLA-4, PD1 and its ligands PD-L1 and PD-L2 and in addition LAG-3, BTLA, B7H3, B7H4, TIM3, KIR. The pathways involving LAG3, BTLA, B7H3, B7H4, TIM3, and KIR are recognized in the art to constitute immune checkpoint pathways similar to the CTLA-4 and PD-1 dependent pathways (see e.g. Pardoll, 2012; Mellman et al., 2011).

An "immune checkpoint inhibitor" refers to any compound inhibiting the function of an immune checkpoint protein. Inhibition includes reduction of function and full blockade. In particular the immune checkpoint protein is a human immune checkpoint protein. Thus the immune checkpoint protein inhibitor in particular is an inhibitor of a human immune checkpoint protein.

The terms "hormonal" and "endocrine" therapy or treatment are used interchangeably herein to refer to an agent which blocks the body's ability to produce a specific hormone (e.g., estrogen) or interferes with hormone action.

The term "determining an expression level" as used herein means the application of a gene specific reagent such as a probe, primer or antibody and/or a method to a sample, for example a sample of the subject and/or a control sample, for ascertaining or measuring quantitatively, semi-quantitatively or qualitatively the amount of a gene or genes, for example the amount of mRNA. For example, a level of a gene can be determined by a number of methods including for example immunoassays including for example immunohistochemistry, ELISA, Western blot, immunoprecipitation and the like, where a biomarker detection agent such as an antibody for example, a labeled antibody, specifically binds the biomarker and permits for example relative or absolute ascertaining of the amount of polypeptide biomarker, hybridization and PCR protocols where a probe or primer or primer set are used to ascertain the amount of nucleic acid biomarker, including for example probe based and amplification based methods including for example microarray analysis, RT-PCR such as quantitative RT-PCR, serial analysis of gene expression (SAGE), Northern Blot, digital molecular barcoding technology, for example Nanostring: nCounter™ Analysis, and TaqMan quantitative PCR assays. Other methods of mRNA detection and quantification can be applied, such as mRNA in situ hybridization in formalin-fixed, paraffin-embedded (FFPE) tissue samples or cells. This technology is currently offered by the QuantiGene®ViewRNA (Affymetrix), which uses probe sets for each mRNA that bind specifically to an amplification system to amplify the hybridization signals; these amplified signals can be visualized using a standard fluorescence microscope or imaging system. This system for example can detect and measure transcript levels in heterogeneous samples; for example, if a sample has normal and tumor cells present in the same tissue section. As mentioned, TaqMan probe-based gene expression analysis (PCR-based) can also be used for measuring gene expression levels in tissue samples, and for example for measuring mRNA levels in FFPE samples. In brief, TaqMan probe-based assays utilize a probe that hybridizes specifically to the mRNA target. This probe contains a quencher dye and a reporter dye (fluorescent molecule) attached to each end, and fluorescence is emitted only when specific hybridization to the mRNA target occurs. During the amplification step, the exonuclease activity of the polymerase enzyme causes the quencher and the reporter dyes to be detached from the probe, and fluorescence emission can occur. This fluorescence emission is recorded and signals are measured by a detection system; these signal intensities are used to calculate the abundance of a given transcript (gene expression) in a sample.

The term "sample" as used herein includes any biological specimen obtained from a patient. Samples include, without limitation, whole blood, plasma, serum, red blood cells, white blood cells (e.g., peripheral blood mononuclear cells), ductal lavage fluid, nipple aspirate, lymph (e.g., disseminated tumor cells of the lymph node), bone marrow aspirate, saliva, urine, stool (i.e., feces), sputum, bronchial lavage fluid, tears, fine needle aspirate (e.g., harvested by fine needle aspiration that is directed to a target, such as a tumor, or is random sampling of normal cells, such as periareolar), any other bodily fluid, a tissue sample (e.g., tumor tissue) such as a biopsy of a tumor (e.g., needle biopsy) or a lymph node (e.g., sentinel lymph node biopsy), and cellular extracts thereof. In some embodiments, the sample is whole blood or a fractional component thereof such as plasma, serum, or a cell pellet. In some embodiments, the sample is a formalin fixed paraffin embedded (FFPE) tumor tissue sample, e.g., from a solid tumor of the breast.

A "biopsy" refers to the process of removing a tissue sample for diagnostic or prognostic evaluation, and to the tissue specimen itself. Any biopsy technique known in the art can be applied to the methods and compositions of the present invention. The biopsy technique applied will generally depend on the tissue type to be evaluated and the size and type of the tumor (i.e., solid or suspended (i.e., blood or ascites)), among other factors. Representative biopsy techniques include excisional biopsy, incisional biopsy, needle biopsy (e.g., core needle biopsy, fine-needle aspiration biopsy, etc.), surgical biopsy, and bone marrow biopsy. Biopsy techniques are discussed, for example, in Harrison's Principles of Internal Medicine, Kasper, et al., eds., 16th ed., 2005, Chapter 70, and throughout Part V. One skilled in the art will appreciate that biopsy techniques can be performed to identify cancerous and/or precancerous cells in a given tissue sample.

II. SET$_{ER/PR}$ INDEX

Embodiments of the present disclosure provide an index of tumoral sensitivity to endocrine therapy, referred to herein as the SET$_{ER/PR}$ index. The SET$_{ER/PR}$ index is calculated using the expression level of a combination of genes related to both estrogen receptor (ER) and progesterone receptor (PR), such as disclosed in Table 5 including SLC39A6, STC2, CA12, ESR1, PDZK1, NPY1R, CD2, MAPT, QDPR, AZGP1, ABAT, ADCY1, CD3D, NAT1, MRPS30, DNAJC12, SCUBE2, and KCNE4. In some aspects, 5, 6, 7, 8, 9, 10, 11, 12, 13, 14, 15, 16, 17, or 18 of the genes in Table 5 are used to determine the SET$_{ER/PR}$ index. The ER- and PR-related genes can be normalized to reference genes, such as disclosed in Table 5 including LDHA, ATP5J2, VDAC2, DARS, UCP2, UBE2Z, AK2, WIPF2, APPBP2, and TRIM2. In some aspects, 2, 3, 4, 5, 6, 7, 8, 9 or 10 of the reference genes disclosed in Table 5 are used to normalize the expression of the ER- and PR-related genes.

In some aspects, the SET$_{ER/PR}$ index is calculated as:

$$SET_{ER/PR} = \frac{\sum_{i=1}^{18} T_i}{18} - \frac{\sum_{j=1}^{10} R_j}{10} + 2,$$

where T$_i$ is the expression of the ith of the 18 target genes and R, the expression of the jth of the 10 reference genes. A constant is added to optimize the separation into hormone receptor-positive and negative cases by immunohistochemistry at a score value of 0.

A. Isolation of RNA

Aspects of the present disclosure concern the isolation of RNA from a patient sample for use in determining the SET$_{ER/PR}$ index. The patient sample may blood, saliva, urine, or a tissue biopsy. The tissue biopsy may be a tumor biopsy that has been flash-frozen (e.g. in liquid nitrogen), formalin-fixed and paraffin-embedded (FFPE), and/or preserved by a RNA stabilization agent (e.g., RNAlater). In some aspects, isolation is not necessary, and the assay directly utilizes RNA from within a homogenate of the tissue sample. In certain aspects the homogenate of FFPE tumor sample is enzymatically digested.

RNA may be isolated using techniques well known to those of skill in the art. Methods generally involve lysing the cells with a chaotropic (e.g., guanidinium isothiocyanate) and/or detergent (e.g., N-lauroyl sarcosine) prior to implementing processes for isolating particular populations of RNA. Chromatography is a process often used to separate or isolate nucleic acids from protein or from other nucleic acids. Such methods can involve electrophoresis with a gel matrix, filter columns, coated magnetic beads, alcohol precipitation, and/or other chromatography.

B. Expression Assessment

In certain aspects, methods of the present disclosure concern measuring expression of ER- and PR-related genes as well as one or more reference genes in a sample from a subject with breast cancer. The expression information may be obtained by testing cancer samples by a lab, a technician, a device, or a clinician. In a certain embodiment, the differential expression of one or more genes including those of Table 5 may be measured.

Expression levels of the genes can be detected using any suitable means known in the art. For example, detection of gene expression can be accomplished by detecting nucleic acid molecules (such as RNA) using nucleic acid amplification methods (such as RT-PCR, droplet-based RT amplification, exon capture of RNA sequence library, next generation RNA sequencing), array analysis (such as microarray analysis), or hybridization methods (such as ribonuclease protection assay, bead-based assays, or Nanostring®). Detection of gene expression can also be accomplished using assays that detect the proteins encoded by the genes, including immunoassays (such as ELISA, Western blot, RIA assay, or protein arrays).

The pattern or signature of expression in each cancer sample may then be used to generate a cancer prognosis or classification, such as predicting cancer survival or recurrence, using the SET$_{ER/PR}$ index. The expression of one or more of ER- and PR-related genes could be assessed to predict or report prognosis or prescribe treatment options for cancer patients, especially breast cancer patients.

The expression of one or more ER- and PR-related genes may be measured by a variety of techniques that are well known in the art. Quantifying the levels of the messenger RNA (mRNA) of a gene may be used to measure the expression of the gene. Alternatively, quantifying the levels of the protein product of ER- and PR-related genes may be to measure the expression of the genes. Additional information regarding the methods discussed below may be found in Ausubel et al., (2003) Current Protocols in Molecular Biology, John Wiley & Sons, New York, NY, or Sambrook et al. (1989) Molecular Cloning: A Laboratory Manual, Cold Spring Harbor Press, Cold Spring Harbor, NY. One skilled in the art will know which parameters may be manipulated to optimize detection of the mRNA or protein of interest.

A nucleic acid microarray may be used to quantify the differential expression of a plurality of ER- and PR-related genes. Microarray analysis may be performed using commercially available equipment, following manufacturer's protocols, such as by using the Affymetrix GeneChip® technology (Santa Clara, CA) or the Microarray System from Incyte (Fremont, CA). Typically, single-stranded nucleic acids (e.g., cDNAs or oligonucleotides) are plated, or arrayed, on a microchip substrate. The arrayed sequences are then hybridized with specific nucleic acid probes from the cells of interest. Fluorescently labeled cDNA probes may be generated through incorporation of fluorescently labeled deoxynucleotides by reverse transcription of RNA extracted from the cells of interest. Alternatively, the RNA may be amplified by in vitro transcription and labeled with a marker, such as biotin. The labeled probes are then hybridized to the immobilized nucleic acids on the microchip under highly stringent conditions. After stringent washing to remove the non-specifically bound probes, the chip is scanned by confocal laser microscopy or by another detection method, such as a CCD camera. The raw fluorescence intensity data in the hybridization files are generally preprocessed with a robust statistical normalization algorithm to generate expression values.

Quantitative real-time PCR (qRT-PCR) may also be used to measure the differential expression of a plurality of ER- and PR-related genes. In qRT-PCR, the RNA template is generally reverse transcribed into cDNA, which is then amplified via a PCR reaction. The amount of PCR product is followed cycle-by-cycle in real time, which allows for determination of the initial concentrations of mRNA. To measure the amount of PCR product, the reaction may be performed in the presence of a fluorescent dye, such as SYBR Green, which binds to double-stranded DNA. The reaction may also be performed with a fluorescent reporter probe that is specific for the DNA being amplified.

For example, extracted RNA can be reverse-transcribed using a GeneAmp® RNA PCR kit (Perkin Elmer, Calif., USA), following the manufacturer's instructions. In some embodiments, gene expression levels can be determined using a gene expression analysis technology that measure mRNA in solution. Methods of detecting gene expression are described for example in U.S. Patent Application Nos. US20140357660, and US20130259858; incorporated herein by reference. Examples of such gene expression analysis technologies include, but not limited to RNAscope™, RT-PCR, Nanostring®, QuantiGene®, gNPA®, HTG®, microarray, and sequencing. For example, methods of Nanostring use labeled reporter molecules, referred to as labeled "nanoreporters," that are capable of binding individual target molecules. Through the nanoreporters' label codes, the binding of the nanoreporters to target molecules results in the identification of the target molecules. Methods of Nanostring are described in U.S. Pat. No. 7,473,767 (see also, Geiss et al., 2008). Methods may include the Rain-Dance droplet amplification method such as described in U.S. Pat. No. 8,535,889, incorporated herein by reference. Sequencing may include exon capture, such as Illumina targeted sequencing after the generation of a tagged library for next generation sequencing (e.g. described in International Patent Application No. WO2013131962, incorporated herein by reference).

A non-limiting example of a fluorescent reporter probe is a TaqMan® probe (Applied Biosystems, Foster City, CA). The fluorescent reporter probe fluoresces when the quencher is removed during the PCR extension cycle. Multiplex qRT-PCR may be performed by using multiple gene-specific reporter probes, each of which contains a different fluorophore. Fluorescence values are recorded during each cycle and represent the amount of product amplified to that point in the amplification reaction. To minimize errors and reduce any sample-to-sample variation, qRT-PCR is typically performed using a reference standard. The ideal reference standard is expressed at a constant level among different tissues, and is unaffected by the experimental treatment. The system can include a thermocycler, laser, charge-coupled device (CCD) camera, and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

To minimize errors and the effect of sample-to-sample variation, RT-PCR can be performed using an internal standard. The ideal internal standard is expressed at a constant level among different tissues, and is unaffected by an experimental treatment. RNAs commonly used to normalize patterns of gene expression are mRNAs for the housekeeping genes GAPDH, β-actin, and 18S ribosomal RNA.

A variation of RT-PCR is real time quantitative RT-PCR, which measures PCR product accumulation through a dual-labeled fluorogenic probe (e.g., TAQMAN® probe). Real time PCR is compatible both with quantitative competitive PCR, where internal competitor for each target sequence is used for normalization, and with quantitative comparative PCR using a normalization gene contained within the sample, or a housekeeping gene for RT-PCR (see Heid et al., 1996). Quantitative PCR is also described in U.S. Pat. No. 5,538,848. Related probes and quantitative amplification procedures are described in U.S. Pat. Nos. 5,716,784 and 5,723,591. Instruments for carrying out quantitative PCR in microtiter plates are available from PE Applied Biosystems (Foster City, CA).

The steps of a representative protocol for quantitating gene expression level using fixed, paraffin-embedded tissues as the RNA source, including mRNA isolation, purification, primer extension and amplification are given in various published journal articles (see Godfrey et al., 2000; Specht et al., 2001). Briefly, a representative process starts with cutting about 10μη thick sections of paraffin-embedded neoplasm tissue samples or adjacent non-cancerous tissue. The RNA is then extracted, and protein and DNA are removed. Alternatively, RNA is isolated directly from a neoplasm sample or other tissue sample. After analysis of the RNA concentration, RNA repair and/or amplification steps can be included, if necessary, and RNA is reverse transcribed using gene specific primers, followed by preparation of a tagged RNA sequencing library, and paired-end sequencing. In another example, the RNA is not reverse transcribed, but is directly hybridized to a specific template and then labeled with oligonucleotides and/or chemical or fluorescent color to be detected and counted by a laser.

Immunohistochemical staining may also be used to measure the differential expression of a plurality of ER- and PR-related genes. This method enables the localization of a protein in the cells of a tissue section by interaction of the protein with a specific antibody. For this, the tissue may be fixed in formaldehyde or another suitable fixative, embedded in wax or plastic, and cut into thin sections (from about 0.1 mm to several mm thick) using a microtome. Alternatively, the tissue may be frozen and cut into thin sections using a cryostat. The sections of tissue may be arrayed onto and affixed to a solid surface (i.e., a tissue microarray). The sections of tissue are incubated with a primary antibody against the antigen of interest, followed by washes to remove the unbound antibodies. The primary antibody may be coupled to a detection system, or the primary antibody may be detected with a secondary antibody that is coupled to a detection system. The detection system may be a fluorophore or it may be an enzyme, such as horseradish peroxidase or alkaline phosphatase, which can convert a substrate into a colorimetric, fluorescent, or chemiluminescent product. The stained tissue sections are generally scanned under a microscope. Because a sample of tissue from a subject with cancer may be heterogeneous, i.e., some cells may be normal and other cells may be cancerous, the percentage of positively stained cells in the tissue may be determined. This measurement, along with a quantification of the intensity of staining, may be used to generate an expression value for the biomarker.

An enzyme-linked immunosorbent assay, or ELISA, may be used to measure the differential expression of a plurality of ER- and PR-related genes. There are many variations of an ELISA assay. All are based on the immobilization of an antigen or antibody on a solid surface, generally a microtiter plate. The original ELISA method comprises preparing a sample containing the biomarker proteins of interest, coating the wells of a microtiter plate with the sample, incubating each well with a primary antibody that recognizes a specific antigen, washing away the unbound antibody, and then detecting the antibody-antigen complexes. The antibody-antibody complexes may be detected directly. For this, the primary antibodies are conjugated to a detection system, such as an enzyme that produces a detectable product. The antibody-antibody complexes may be detected indirectly. For this, the primary antibody is detected by a secondary antibody that is conjugated to a detection system, as described above. The microtiter plate is then scanned and the raw intensity data may be converted into expression values using means known in the art.

An antibody microarray may also be used to measure the differential expression of a plurality of ER- and PR-related genes. For this, a plurality of antibodies is arrayed and covalently attached to the surface of the microarray or biochip. A protein extract containing the biomarker proteins of interest is generally labeled with a fluorescent dye.

The labeled ER- and PR-related genes proteins may be incubated with the antibody microarray. After washes to remove the unbound proteins, the microarray is scanned. The raw fluorescent intensity data may be converted into expression values using means known in the art.

Luminex multiplexing microspheres may also be used to measure the differential expression of a plurality of biomarkers. These microscopic polystyrene beads are internally color-coded with fluorescent dyes, such that each bead has a unique spectral signature (of which there are up to 100). Beads with the same signature are tagged with a specific oligonucleotide or specific antibody that will bind the target of interest (i.e., biomarker mRNA or protein, respectively). The target, in turn, is also tagged with a fluorescent reporter. Hence, there are two sources of color, one from the bead and the other from the reporter molecule on the target. The beads are then incubated with the sample containing the targets, of which up 100 may be detected in one well. The small size/surface area of the beads and the three dimensional exposure of the beads to the targets allows for nearly solution-phase kinetics during the binding reaction. The captured targets are detected by high-tech fluidics based upon flow cytometry in which lasers excite the internal dyes that identify each bead and also any reporter dye captured during the assay. The data from the acquisition files may be converted into expression values using means known in the art.

In situ hybridization may also be used to measure the differential expression of a plurality of biomarkers. This method permits the localization of mRNAs of interest in the cells of a tissue section. For this method, the tissue may be frozen, or fixed and embedded, and then cut into thin sections, which are arrayed and affixed on a solid surface. The tissue sections are incubated with a labeled antisense probe that will hybridize with an mRNA of interest. The hybridization and washing steps are generally performed under highly stringent conditions. The probe may be labeled with a fluorophore or a small tag (such as biotin or digoxigenin) that may be detected by another protein or antibody, such that the labeled hybrid may be detected and visualized under a microscope. Multiple mRNAs may be detected simultaneously, provided each antisense probe has a distinguishable label. The hybridized tissue array is generally scanned under a microscope. Because a sample of tissue from a subject with cancer may be heterogeneous, i.e., some cells may be normal and other cells may be cancerous, the percentage of positively stained cells in the tissue may be determined. This measurement, along with a quantification of the intensity of staining, may be used to generate an expression value for each biomarker.

C. ESR1 Mutations

Activating mutations in the estrogen receptor gene, ESR1, are a key mechanism in acquired endocrine resistance in breast cancer therapy. Accordingly, some aspects of the present invention further refine the $SET_{ER/PR}$ index by including variables for the expression of mutated ESR1. The presence of transcript expressing a mutated form of ESR1 is detected by specific primers that amplify a specific part of the ligand-binding domain sequence of ESR1 transcript that is known to be a region that is enriched for activating mutations. The proportion of the transcript expressing a mutated form of ESR1 is calculated as the expression of mutated ESR1 over the expression of ESR1 measured using different primers that detect a region of the ESR1 transcript that is reliably expressed in samples and is not prone to mutation. In one example, the mutation status is incorporated logistically with SET index status (yes/no combined with high/low). In another example, the mutation status of the transcript, the proportion of ESR1 transcript that is mutated, and the SET index value are incorporated into a multivariable index score, where the coefficients of the score are based on multivariable Cox regression model of prognosis following endocrine therapy.

Mutations of ESR1 are known in the art. For example, five ESR1 mutations identified encoding p.Leu536Gln, p.Tyr537Ser, p.Tyr537Cys, p.Tyr537Asn and p.Asp538Gly were shown to result in constitutive activity and continued responsiveness to anti-estrogen therapies in vitro (Robinson et al., 2013). Other ESR1 mutations include S463P, V534E, P535H, L536Q, L536R, Y537C, Y537S, Y537N, and D538G.

III. METHODS OF TREATMENT

Provided herein are methods for treating or delaying progression of breast cancer in an individual determined to be sensitive to endocrine therapy using the $SET_{ER/PR}$ index comprising administering to the individual an effective amount of a hormonal therapy. The breast cancer may be Stage II, Stage III, or Stage IV breast cancer and, in particular aspects, the Stage IV breast cancer is metastatic and relapsed after prior treatments. In certain aspects, the breast cancer is hormone receptor-positive (i.e., positive for the receptors for the hormones estrogen (ER-positive cancers) and/or progesterone (PR-positive cancers) and/or HER2-negative.

Exemplary hormonal therapies for breast cancer include the SERM, AI, and SERD classes of drugs that inhibit the activity of the estrogen and estrogen-receptor complex, such as tamoxifen, toremifene, and fulvestrant. Other hormonal therapies include treatments to lower estrogen levels including aromatase inhibitors such as letrozole, anastrozole, and exemestane. Permanent ovarian ablation can be done by surgically removing the ovaries. This operation is called an oophorectomy. More often, ovarian ablation is done with drugs called luteinizing hormone-releasing hormone (LHRH) analogs, such as goserelin (Zoladex®) or leuprolide (Lupron®). These drugs stop the signal that the body sends to ovaries to make estrogens. They can be used alone or with other hormone drugs (tamoxifen, aromatase inhibitors, fulvestrant) as hormone therapy in pre-menopausal women. The effectiveness of hormonal therapy may also be enhanced by the addition of an additional therapy to synergistically inhibit a different biological pathway, such as palbociclib (Cdk4/6 inhibitor), everolimus (mTOR/PI3K inhibitor), immune therapy, or other therapies.

In some embodiments, the individual has cancer that is resistant (has been demonstrated to be resistant) to one or more anti-cancer therapies. In some embodiments, resistance to anti-cancer therapy includes recurrence of cancer or refractory cancer. Recurrence may refer to the reappearance of cancer, in the original site or a new site, after treatment. In some embodiments, resistance to anti-cancer therapy includes progression of the cancer during treatment with the anti-cancer therapy. In some embodiments, the cancer is at early stage or at late stage.

In some aspects, the patient has been previously administered a hormonal therapy and/or additional anti-cancer therapy. For example, the patient may have been administered a hormonal therapy in combination with chemotherapy, such as for five years. In some aspects, the patients has shown previous sensitivity to a hormonal therapy.

In some aspects, the hormonal therapy is administered in combination with at least one additional anti-cancer therapy. The hormonal therapy may be administered before, during, after, or in various combinations relative to the additional anti-cancer agent. The administrations may be in intervals ranging from concurrently to minutes to days to weeks. In embodiments where the hormonal therapy is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the hormonal therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

The hormonal therapy and, optionally the anti-cancer agent, may be administered by the same route of administration or by different routes of administration. In some embodiments, the hormonal therapy and/or anti-cancer agent is administered intravenously, intramuscularly, subcutaneously, topically, orally, transdermally, intraperitoneally, intraorbitally, by implantation, by inhalation, intrathecally, intraventricularly, or intranasally. An effective amount of the hormonal therapy and/or anti-cancer agent may be administered for prevention or treatment of disease. The appropriate dosage of the hormonal therapy and anti-cancer agent be determined based on the type of disease to be treated, severity and course of the disease, the clinical condition of the individual, the individual's clinical history and response to the treatment, and the discretion of the attending physician.

Intratumoral injection, or injection into the tumor vasculature is specifically contemplated for discrete, solid, accessible tumors. Local, regional or systemic administration also may be appropriate. For tumors of >4 cm, the volume to be administered will be about 4-10 ml (in particular 10 ml), while for tumors of <4 cm, a volume of about 1-3 ml will be used (in particular 3 ml). Multiple injections delivered as single dose comprise about 0.1 to about 0.5 ml volumes.

A. Pharmaceutical Compositions

Also provided herein are pharmaceutical compositions and formulations comprising the hormonal therapy, optionally an anti-cancer agent and a pharmaceutically acceptable carrier.

Pharmaceutical compositions and formulations as described herein can be prepared by mixing the active ingredients (such as an antibody or a polypeptide) having the desired degree of purity with one or more optional pharmaceutically acceptable carriers (Remington's Pharmaceutical Sciences 22nd edition, 2012), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn— protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

B. Anti-Cancer Therapy

In certain embodiments, the compositions and methods of the present embodiments involve hormonal therapy in sequence or combination with at least additional anti-cancer agent. The additional therapy may be radiation therapy, surgery (e.g., lumpectomy and a mastectomy), chemotherapy, targeted molecular inhibitor, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant, neoadjuvant, or palliative therapy.

In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting receptor or receptor kinase signaling molecules, cyclin-dependent kinases or the cell cycle control, mTOR/PI3K pathway, HSP90 inhibitor, tubulin inhibitor, apoptosis inhibitor, and/or chemopreventative agent. The additional therapy may be one or more of the chemotherapeutic agents known in the art.

Various combinations may be employed. For the example below a hormonal therapy is "A" and an anti-cancer therapy is "B":

---

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

---

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaII and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein transferase inhibitors, transplatinum, and pharmaceutically acceptable salts, acids, or derivatives of any of the above.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates have emerged as a breakthrough approach to the development of cancer therapeutics. Cancer is one of the leading causes of deaths in the world. Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen (Carter et al., 2008; Teicher 2014; Leal et al., 2014). Targeted delivery of the drug also minimizes its exposure in normal tissues, resulting in decreased toxicity and improved therapeutic index. The approval of two ADC drugs, ADCE-TRIS® (brentuximab vedotin) in 2011 and KADCYLA® (trastuzumab emtansine or T-DM1) in 2013 by FDA validated the approach. There are currently more than 30 ADC drug candidates in various stages of clinical trials for cancer treatment (Leal et al., 2014). As antibody engineering and linker-payload optimization are becoming more and more mature, the discovery and development of new ADCs are increasingly dependent on the identification and validation of new targets that are suitable to this approach (Teicher 2009) and the generation of targeting MAbs. Two criteria for ADC targets are upregulated/high levels of expression in tumor cells and robust internalization.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739,

24

169; Hui and Hashimoto, 1998; Christodoulides et al., 1998); cytokine therapy, e.g., interferons $\alpha$, $\beta$, and $\gamma$, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

In some embodiments, the immunotherapy may be an immune checkpoint inhibitor. Immune checkpoints are molecules in the immune system that either turn up a signal (e.g., co-stimulatory molecules) or turn down a signal. Inhibitory checkpoint molecules that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAG3), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, in particular, are antibodies, such as human antibodies (e.g., International Patent Publication WO2015016718; Pardoll 2012; both incorporated herein by reference). Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present invention. For example it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide. Exemplary antibodies are described in U.S. Pat. Nos. 8,735,553, 8,354,509, and 8,008,449, all incorporated herein by reference. Other PD-1 axis antagonists for use in the methods provided herein are known in the art such as described in U.S. Patent Application No. 20140294898, 2014022021, and 20110008369, all incorporated herein by reference.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PDL2-Fc fusion soluble receptor described in WO2010/027827 and WO2011/066342.

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129, WO 01/14424, WO 98/42752; WO 00/37504 (CP675,206, also known as tremelimumab; formerly ticilimumab), U.S. Pat. No. 6,207,156; Hurwitz et al., 1998; Camacho et al., 2004; Mokyr et al., 1998 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001014424, WO2000037504, and U.S. Pat. No. 8,017,114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WOO 1/14424). In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2 and CDR3 domains of the VL region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilimumab).

Other molecules for modulating CTLA-4 include CTLA-4 ligands and receptors such as described in U.S. Pat. Nos. 5,844,905, 5,885,796 and International Patent Application Nos. WO1995001994 and WO1998042752; all incorporated herein by reference, and immunoadhesions such as described in U.S. Pat. No. 8,329,867, incorporated herein by reference.

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present embodiments to improve the therapeutic efficacy of treatment. Recently validated and approved clinical examples include the concurrent administration of hormonal therapy with a biotherapy that inhibits the cell cycle (e.g., palbociclib) or the mTOR/PI3K pathway (e.g., everolimus). Further examples can therefore be contemplated. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

IV. ARTICLES OF MANUFACTURE OR KITS

Further embodiments of the invention include kits for the measurement, analysis, and reporting of ER- and PR-related gene expression and transcriptional output. A kit may include, but is not limited to microarray, quantitative RT- PCR, or other genomic platform reagents and materials, as well as hardware and/or software for performing at least a portion of the methods described. For example, custom microarrays or analysis methods for existing microarrays are contemplated. Accordingly, an article of manufacture or a kit is provided comprising a customized assay for determining the $SET_{ER/PR}$ index also provided herein. The article of manufacture or kit can further comprise a package insert comprising instructions for using the customized assay to determine the $SET_{ER/PR}$ index and to then treat or delay progression of breast cancer in an individual. Probes for any of the ER- and PR-related genes described herein may be included in the article of manufacture or kits. Suitable containers include, for example, bottles, vials, bags and syringes. The container may be formed from a variety of materials such as glass, plastic (such as polyvinyl chloride or polyolefin), or metal alloy (such as stainless steel or hastelloy). In some embodiments, the container holds the formulation and the label on, or associated with, the container may indicate directions for use. The article of manufacture or kit may further include other materials desirable from a commercial and user standpoint, including other buffers, diluents, filters, needles, syringes, and package inserts with instructions for use. Suitable containers for the one or more agent include, for example, bottles, vials, bags and syringes.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Evaluation of $SET_{ER/PR}$ Index in Advanced Breast Cancer

Performance in studies of pre-analytical and analytical conditions: FIG. 1 shows the performance of the $SET_{ER/PR}$ in the different technical datasets used for development of the index. $SET_{ER/PR}$ had an excellent reproducibility in technical replicates (ICC=0.990), intra-tumoral replicates (ICC=0.953) and across different tissue samples (cytology vs. tissue, pp=0.952). Score values obtained from Plus2.0 arrays had a slight bias towards higher values when compared to U133A microarrays.

Performance in independent studies of pre-analytical and analytical conditions: FIG. 2 shows the performance of $SET_{ER/PR}$ in pre-analytical and analytical validation studies that were not previously used in the feature selection process. The cross-platform reproducibility was validated in an independent dataset of 32 cases profiled on both U133A and Plus2.0 microarrays with pp=0.994 for the corrected score and pp=0.995 for inter-laboratory reproducibility. There was no significant bias of the adjusted score values in an interaction model. The technical reproducibility of the assay on U133A microarrays was validated in an independent dataset of 36 data pairs (pp=0.993). $SET_{ER/PR}$ was considerably stable over relevant ranges of contamination with liver or normal breast tissue with negative score values regressing more rapidly to the baseline of ESR/PGR associated transcription levels in liver or normal breast tissue. Over a range of 0% to 90% contamination, risk categories were highly consistent (K=0.865 and 0.842, respectively). There was no statistically significant effect of time delay and sample preservation method or extended cold ischemic delay on $SET_{ER/PR}$ measurements.

Prognostic prediction of endocrine sensitivity in meta-static breast cancer: The characteristics of 140 patients with hormone-receptor positive, HER2-negative metastatic breast cancers are summarized in Table 1. $SET_{ER/PR}$ was positively associated with PR immunohistochemical status (p<0.0001) and prior clinical history of endocrine sensitivity (p=0.0471), and negatively associated with the number of prior progression events (p=0.009). The observed range of $SET_{ER/PR}$ was comparable in samples from different sites of metastasis.

TABLE 1

| Characteristics of 140 patients with metastatic breast cancer. Patient Characteristics | | |
| --- | --- | --- |
| Stage at Initial Diagnosis | N | % |
| Stage IV | 45 | 32 |
| Stage I-III | 95 | 68 |
| Visceral Metastases | N | % |
| Yes | 80 | 57 |
| No | 60 | 43 |
| PR Status (IHC) | N | % |
| Positive | 80 | 57 |
| Negative | 60 | 43 |
| Prior Sensitivity | N | % |
| Sensitive | 70 | 50 |
| Resistant | 39 | 28 |
| No Prior Endocrine Rx | 31 | 22 |
| Number of Event (biopsied) | N | % |
| Initial Diagnosis | 20 | 14 |
| $1^{st}$ | 42 | 30 |
| $2^{nd}$ | 26 | 19 |
| $3^{rd}$ | 14 | 10 |
| $4^{th}$ or more | 38 | 27 |
| Protocol Treatment | N | % |
| Endocrine-based | 97 | 69 |
| Chemotherapy-based | 33 | 24 |
| Other | 8 | 6 |
| Radiotherapy alone | 2 | 1 |
| Progression Events | N | % |
| Progression | 130 | 93 |
| Censored | 10 | 7 |
| Death Events | N | % |
| Death | 97 | 70 |
| Censored | 43 | 30 |
| Age | Median | Range |
| Age | 55 | 37-82 |
| Progression-Free Survival (months) | 5.53 | 0.16-74 |
| Overall Survival (months) | 24 | 0.16-126 |

The continuous $SET_{ER/PR}$ index was predictive for progression-free survival in patients receiving endocrine-based therapy (hazard rate 0.609 (0.475-0.782), p=0.0001, Table 2), but not in patients receiving chemotherapy (hazard rate 0.651 (0.403-1.051), p=0.0792). Further analysis was performed on the survival of patients whose biopsy was obtained at a time of recurrence (after prior systemic therapy) and whose next treatment included endocrine therapy (Table 2). The continuous $SET_{ER/PR}$ index was independently prognostic for PFS on hormonal therapy in a multivariate model including PR status of the metastasis, the number of prior relapse events, and the presence or absence of any visceral metastasis (Table 2), if patients had previously demonstrated prior clinical evidence of sensitivity to endocrine therapy.

Transfer to a customized assay based on formalin-fixed paraffin-embedded tissue: The transferability of the score to a customized assay based on formalin-fixed, paraffin-embedded (FFPE) tissue was evaluated using the Affymetrix QuantiGene Plex platform (FIG. 4). 36 breast cancer samples were profiled in duplicate on U133A microarrays and using the targeted assay. The measurements on the QuantiGene platform were repeated in duplicate using two different single sections of the same paraffin block and two different lots of reagents. Two different individuals per-

TABLE 2

Evaluation of $SET_{ER/PR}$ index.

| | Metastatic Cancer: $SET_{ER/PR}$ Index | | | | Metastatic Cancer: $SET_{ER/PR} > 0.65$ | | | | |
|---|---|---|---|---|---|---|---|---|---|
| Chemotherapy | Univariate Cox Regression | | | | Univariate Cox Regression | | | | |
| | HR | lower | upper | p | | HR | lower | upper | p |
| | $SET_{ER/PR}$ 0.65 | 0.40 | 1.05 | 0.08 | $SET_{ER/PR}$ | 1.03 | 0.49 | 2.20 | 0.93 |
| Endocrine | Univariate Cox Regression | | | | Univariate Cox Regression | | | | |
| Therapy | HR | lower | upper | p | | HR | lower | upper | p |
| | $SET_{ER/PR}$ 0.61 | 0.48 | 0.78 | <0.01 | $SET_{ER/PR}$ | 0.40 | 0.26 | 0.62 | <0.01 |
| Endocrine Therapy for Relapsed | Univariate Cox Regression | | | | Univariate Cox Regression | | | | |
| Stage IV Cancer | HR | lower | upper | p | | HR | lower | upper | p |
| | $SET_{ER/PR}$ 0.66 | 0.50 | 0.87 | <0.01 | $SET_{ER/PR}$ | 0.37 | 0.23 | 0.59 | <0.01 |
| | Multivariate Cox Regression | | | | Multivariate Cox Regression | | | | |
| | HR | lower | upper | p | | HR | lower | upper | p |
| | $SET_{ER/PR}$ 0.82 | 0.59 | 1.14 | 0.24 | $SET_{ER/PR}$ | 0.49 | 0.27 | 0.89 | 0.02 |
| | PR status 0.56 | 0.31 | 1.03 | 0.06 | PR status | 0.66 | 0.36 | 1.22 | 0.18 |
| | Visceral 1.79 | 1.04 | 3.09 | 0.04 | Visceral | 1.59 | 0.91 | 2.77 | 0.11 |
| | Event > 2 2.59 | 1.30 | 5.16 | <0.01 | Event > 2 | 2.66 | 1.34 | 5.29 | <0.01 |
| | Prior Sens. 0.44 | 0.23 | 0.84 | 0.01 | Prior Sens. | 0.47 | 0.25 | 0.89 | 0.02 |
| Endocrine Therapy for Relapsed Stage IV Cancer & Prior Clinical Sensitivity to | Univariate Cox Regression | | | | Univariate Cox Regression | | | | |
| Endocrine Therapy | HR | lower | upper | p | | HR | lower | upper | p |
| | $SET_{ER/PR}$ 0.46 | 0.29 | 0.75 | <0.01 | $SET_{ER/PR}$ | 0.24 | 0.12 | 0.48 | <0.01 |
| | Multivariate Cox Regression | | | | Multivariate Cox Regression | | | | |
| | HR | lower | upper | p | | HR | lower | upper | p |
| | $SET_{ER/PR}$ 0.58 | 0.35 | 0.96 | 0.03 | $SET_{ER/PR}$ | 0.32 | 0.15 | 0.69 | <0.01 |
| | PR status 0.49 | 0.24 | 0.97 | 0.04 | PR status | 0.52 | 0.26 | 1.06 | 0.07 |
| | Visceral 1.45 | 0.73 | 2.88 | 0.29 | Visceral | 1.17 | 0.57 | 2.41 | 0.68 |
| | Event > 2 2.82 | 1.32 | 6.03 | <0.01 | Event > 2 | 3.23 | 1.48 | 7.07 | <0.01 |

Figure 1A:
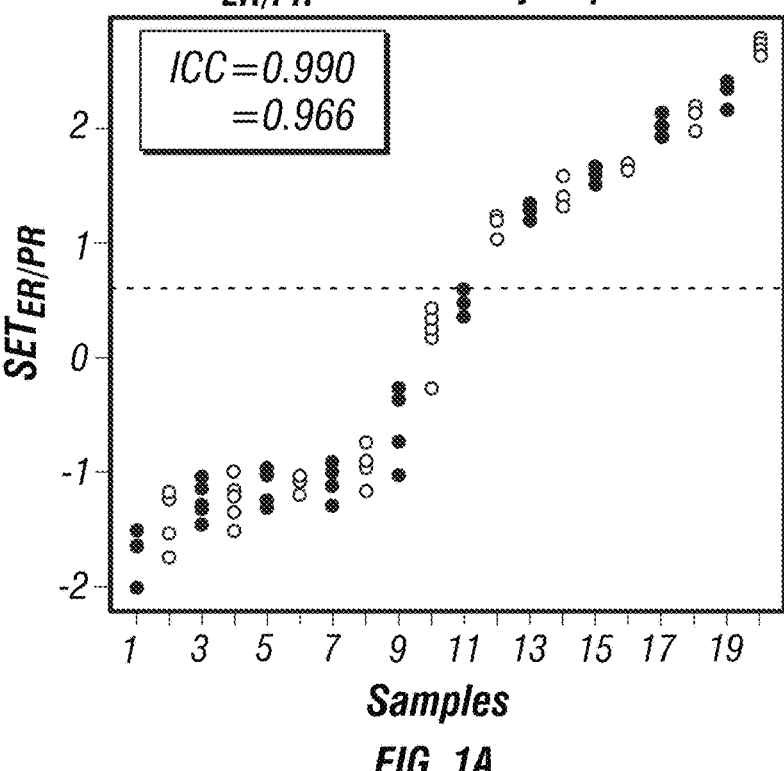
FIGS. 1A-D: Tests for reproducibility of the $SET_{ER/PR}$ index in primary breast cancers: (A) Replicates of the assay procedure. (B) Intra-tumoral heterogeneity across three biopsies from each tumor. (C) Inter-sample type comparison between matched samples of tissue and scrape cytology samples from each tumor. (D) Inter-platform comparison of Affymetrix platform U133A and U133Plus2.0.
Figure 1B:
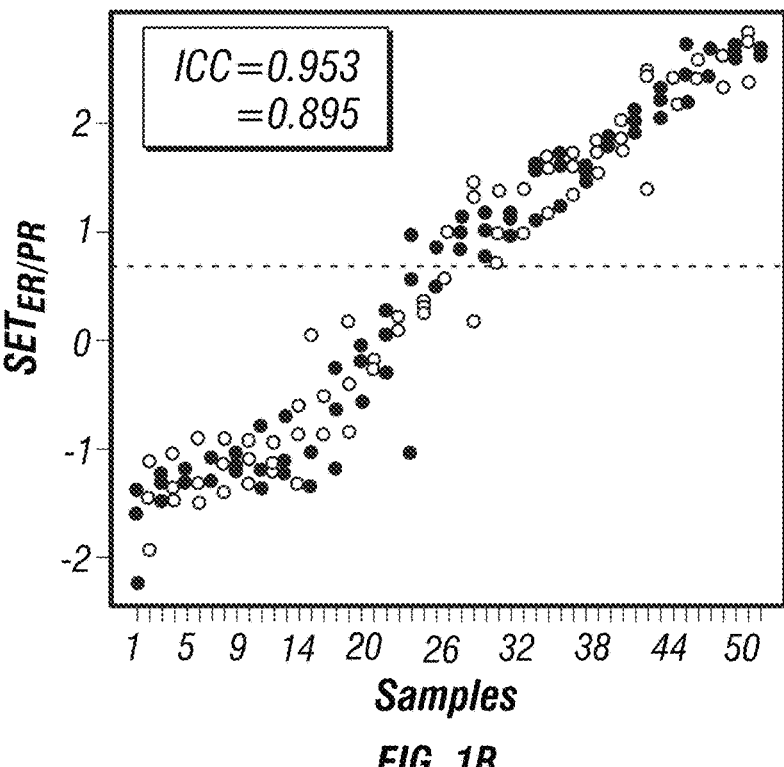
Figure 1C:
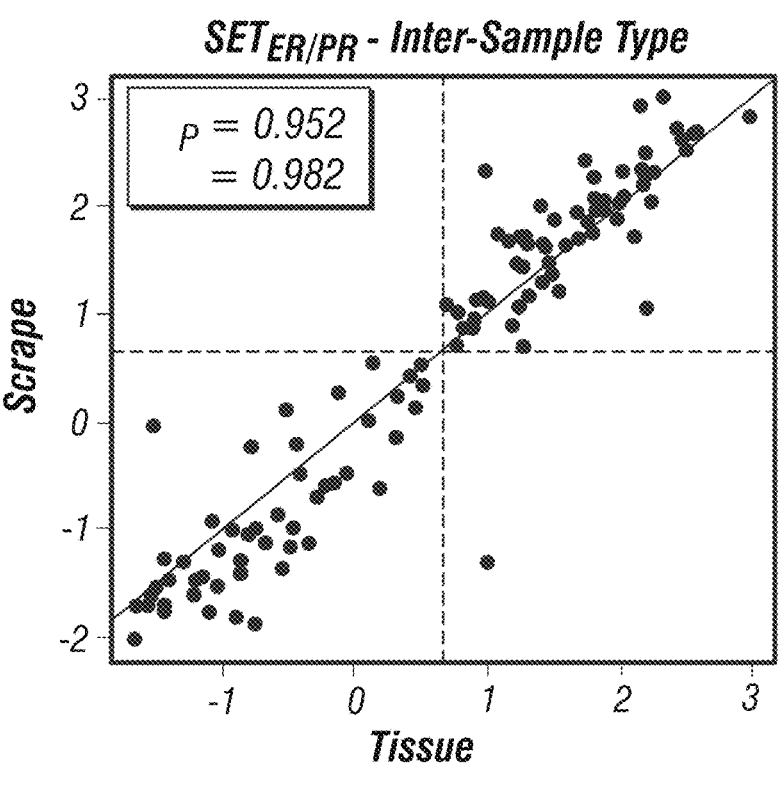
Figure 1D:
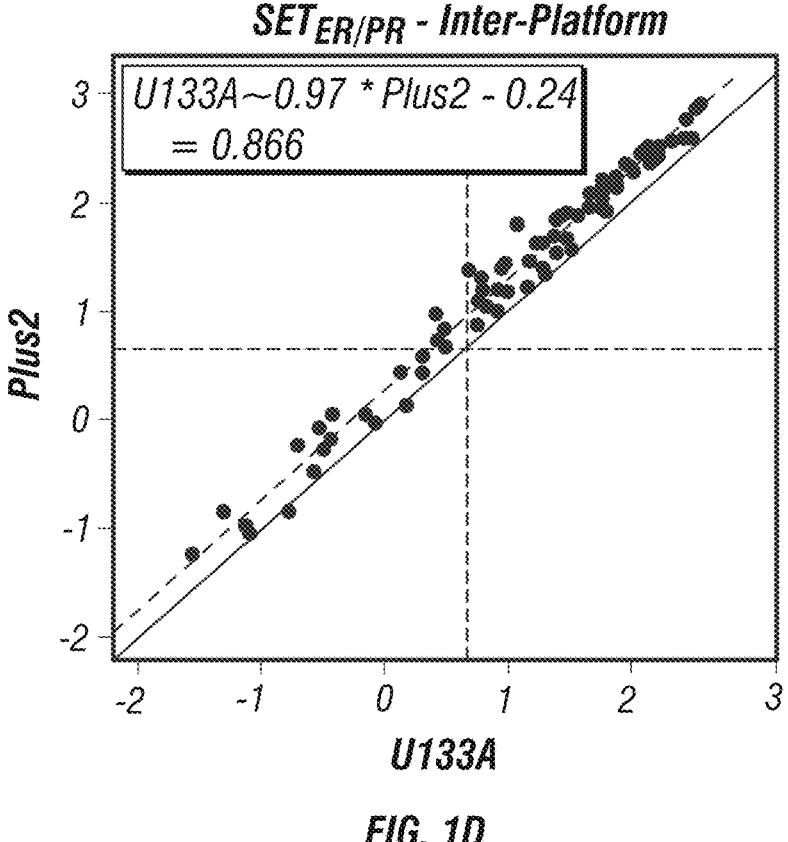
Figure 2A:
FIGS. 2A-F: Tests for reproducibility of the $SET_{ER/PR}$ index in primary breast cancers: (A) Serial spike-in of RNA from normal liver samples. (B) Contamination of breast samples. (C) Duration of extended ex vivo cold ischemic time of samples before preservation. (D) Inter-platform comparison. (E) Inter-laboratory comparison. (F) Intra-assay validation.
Figure 2A:
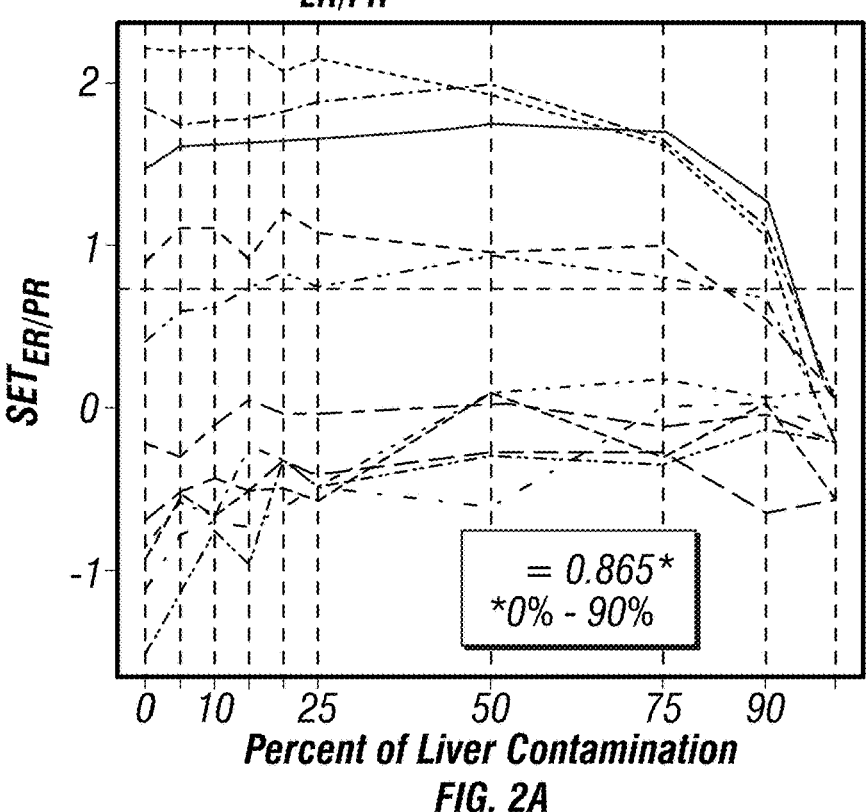
Figure 2B:
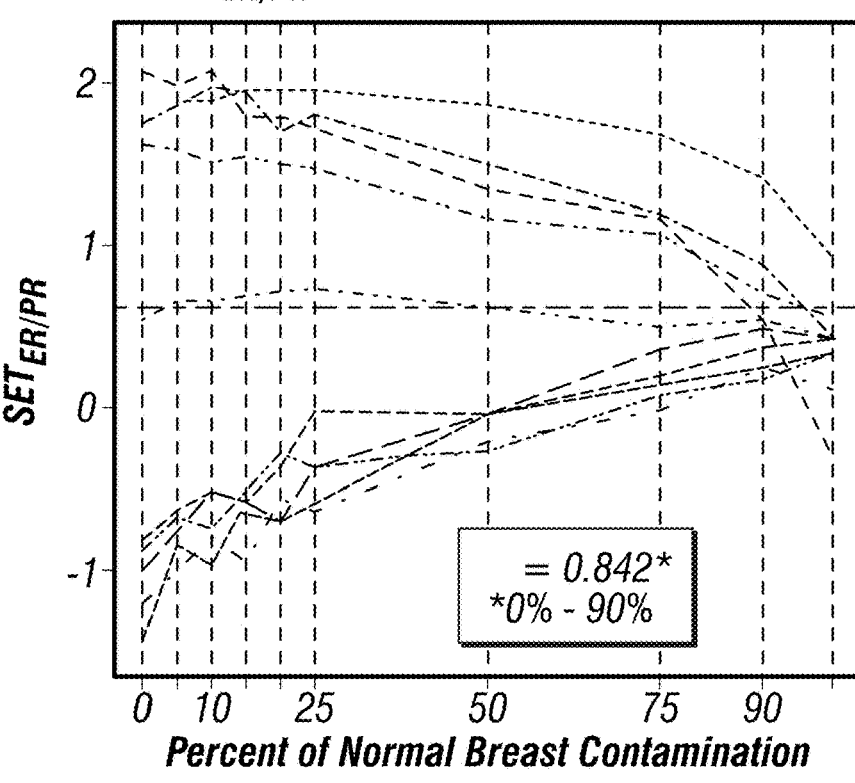
Figure 2C:
Figure 2C:
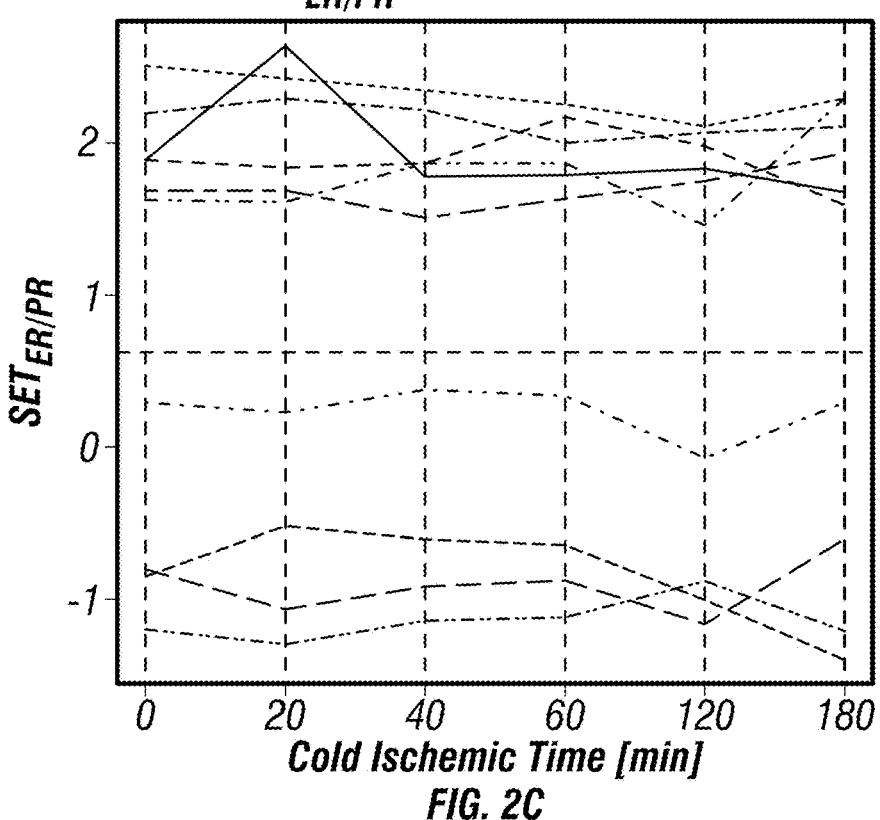
Figure 2D:
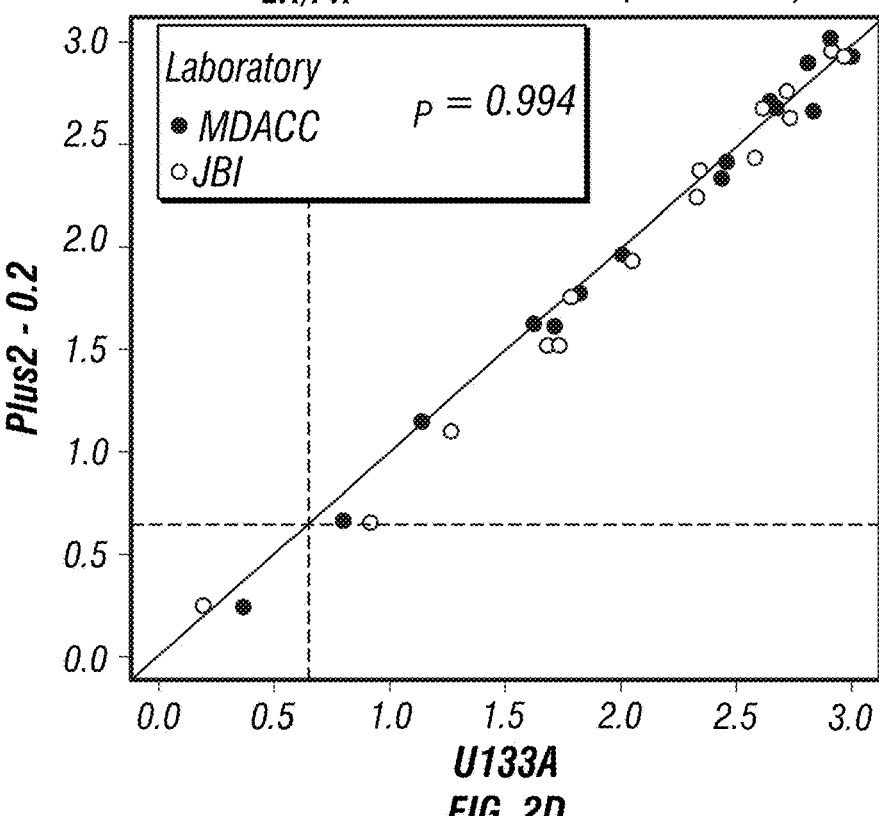
Figure 2E:
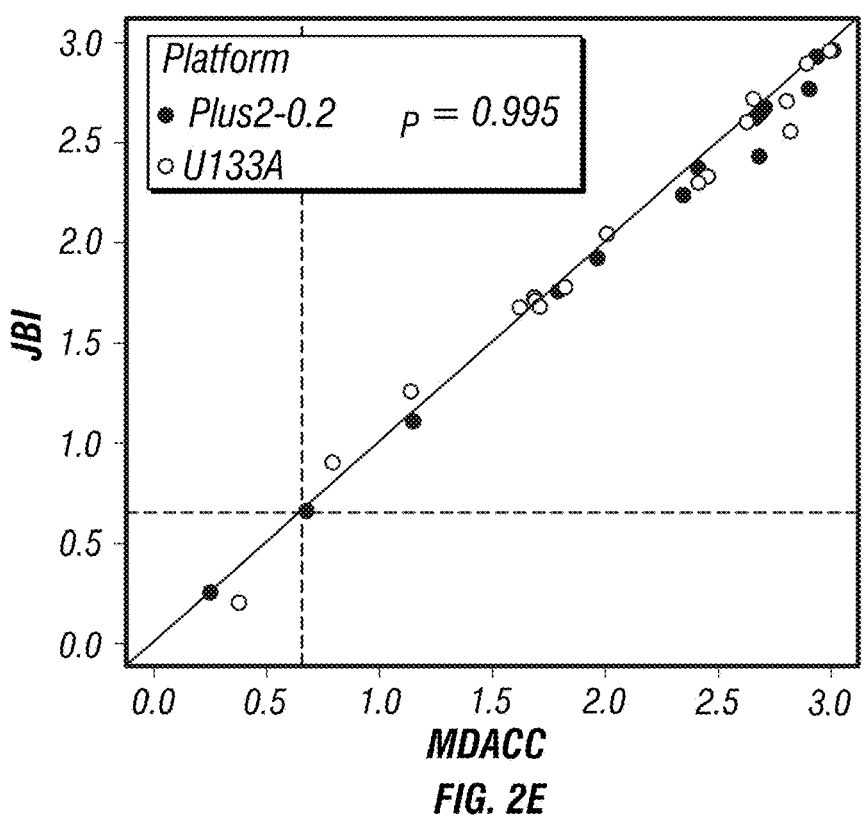
Figure 2F:
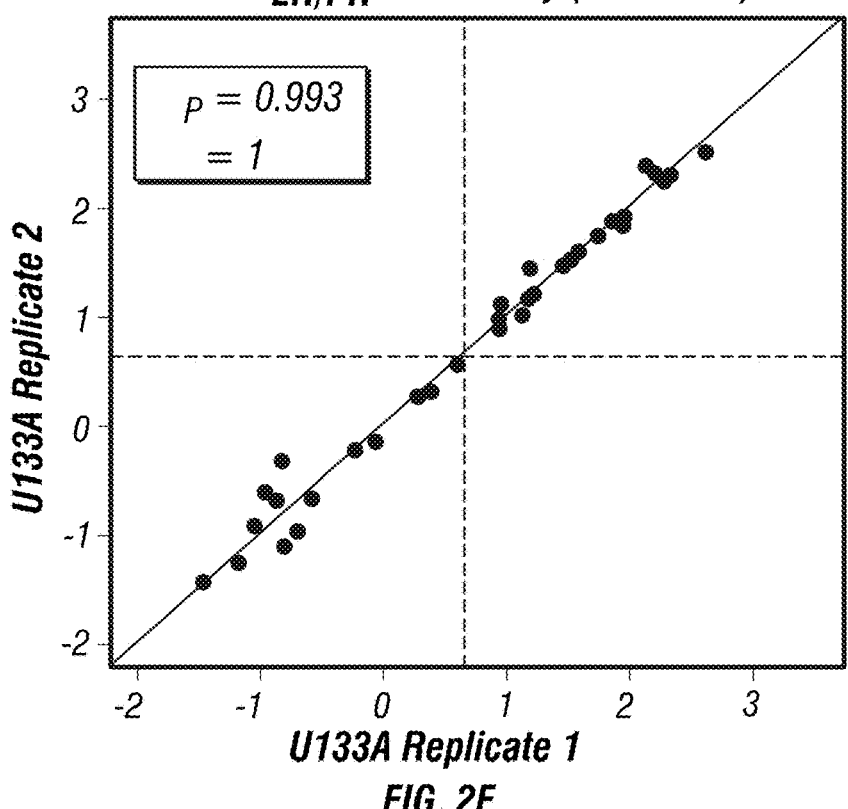
Figure 3A:
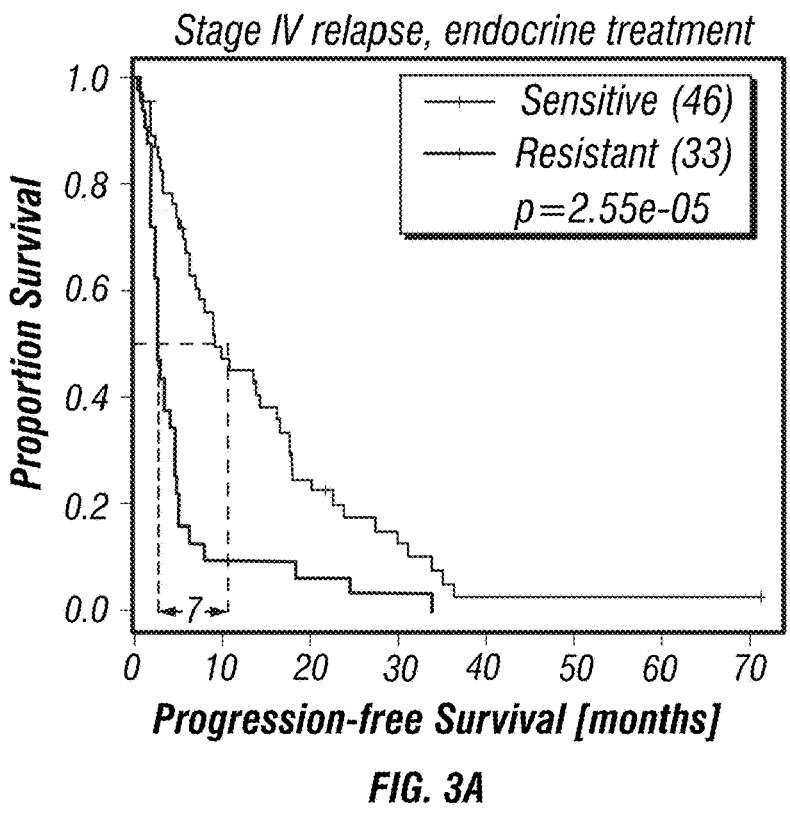
FIGS. 3A-D: Kaplan-Meier plots of survival according to the $SET_{ER/PR}$ index in relapsed metastatic (Stage IV) breast cancer after treatment with hormonal therapy: (A) Progression-free survival (PFS) in 79 patients whose next treatment after tumor biopsy was hormonal therapy, 7 months difference in median PFS. (B) Overall survival (OS) in the same 79 patients whose next treatment after tumor biopsy was hormonal therapy, 31 months difference in median OS. (C) Progression-free survival (PFS) in the subset of 46 patients with a clinical history of prior response to hormonal therapy, 11 months difference in median PFS. (D) Overall survival (OS) in the same subset of 46 patients with a clinical history of prior response to hormonal therapy, 30 months difference in median OS.
Figure 3B:
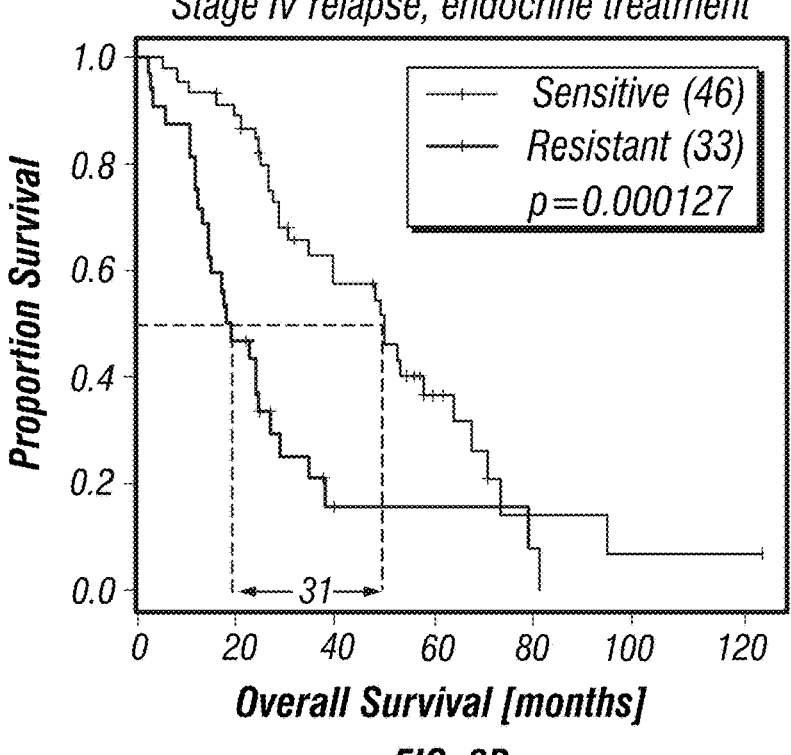
Figure 3C:
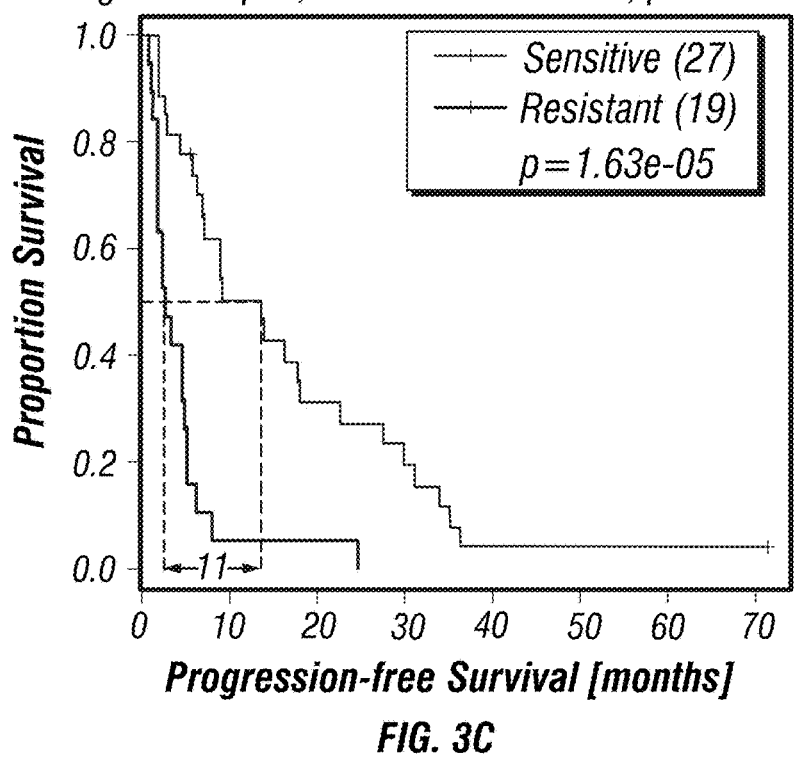
Figure 3D:
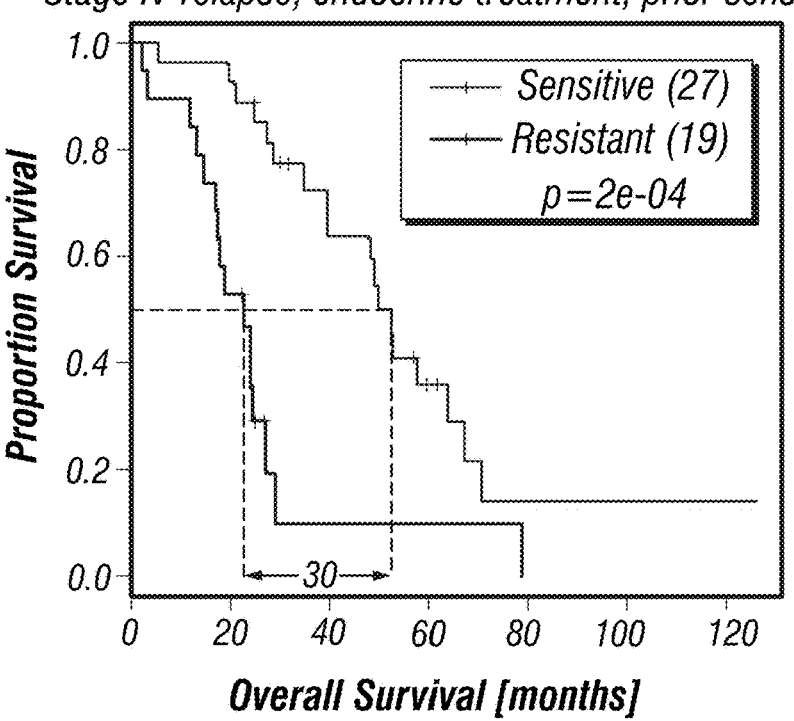
Figure 4A:
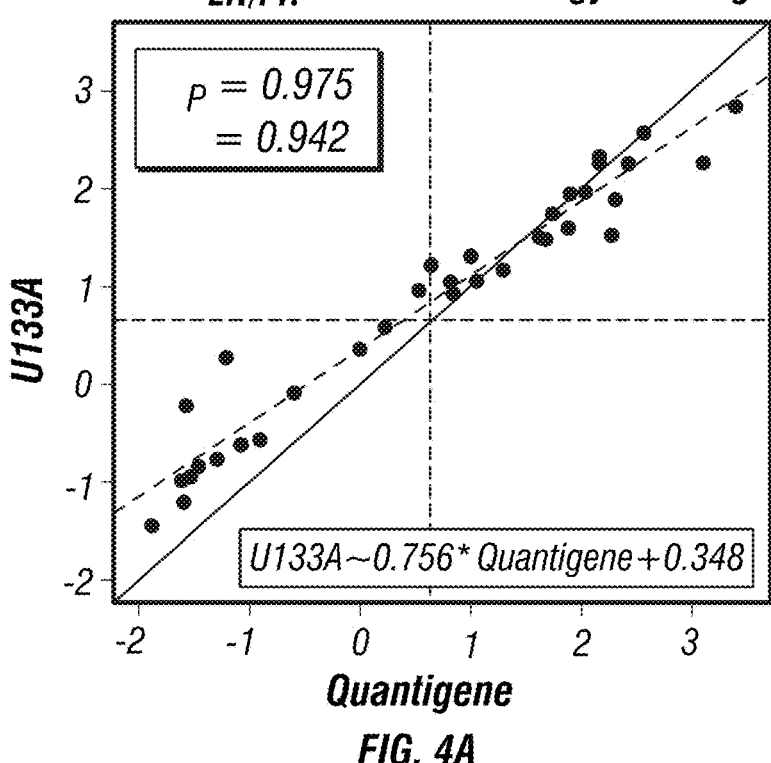
FIGS. 4A-D: Tests for reproducibility of the $SET_{ER/PR}$ index in primary breast cancers when comparing across assay type and sample type (Quantigene Hybridization Assay): (A) Measurements from Affymetrix U133A microarray from fresh frozen tumor sample compared to measurements from Quantigene customized assay (Luminex bead-based hybridization) using matched formalin-fixed and paraffin-embedded (FFPE) sample, gray dashed line shows the linear regression line. (B) Comparison of repeat testing from FFPE tissue sections on slides, including 2 different technicians, each performing each batch of testing on different days, and including 3 batches each, with each batch containing different lots of reagents. (C) Validation study of the results from the study shown in (A), using different tumors and correcting the $SET_{ER/PR}$ index measurements from the Quantigene method by applying the equation from the linear regression analysis shown in (A). (D) Validation study of the results from the study shown in (B), using different tumors and correcting the $SET_{ER/PR}$ index measurements from the Quantigene method by applying the equation from the linear regression analysis shown in (A).
Figure 4B:
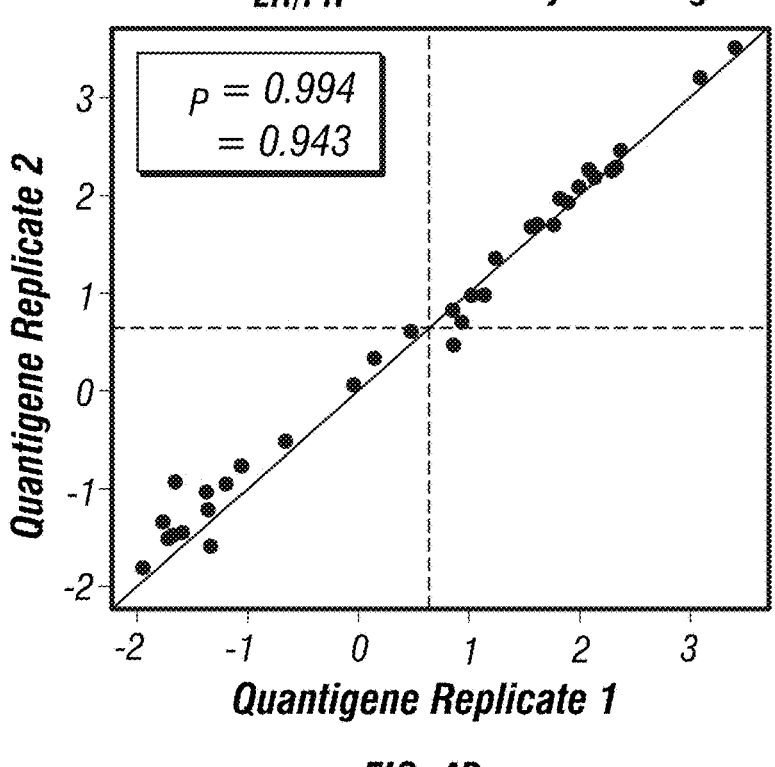
Figure 4C:
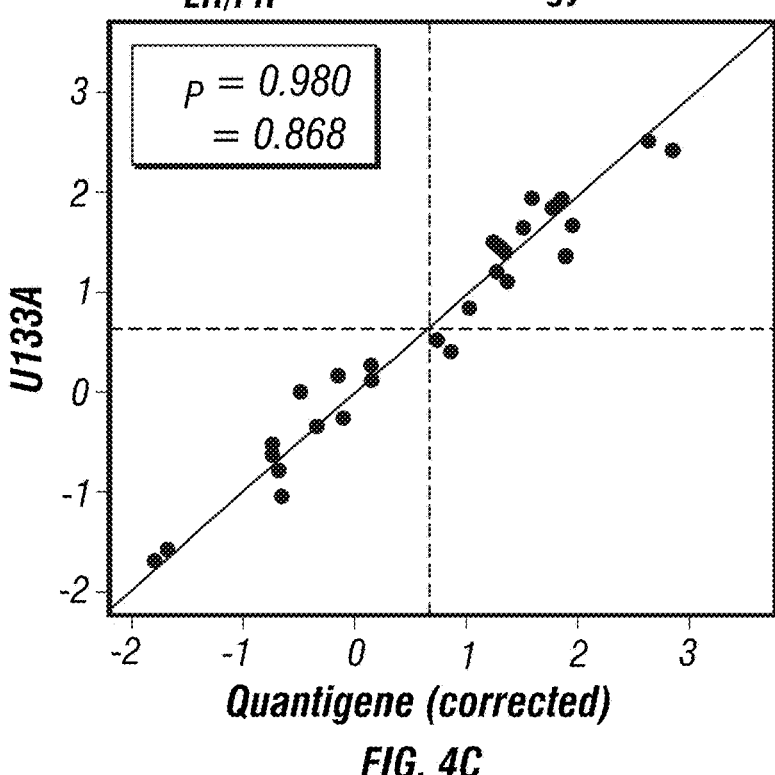
Figure 4D:
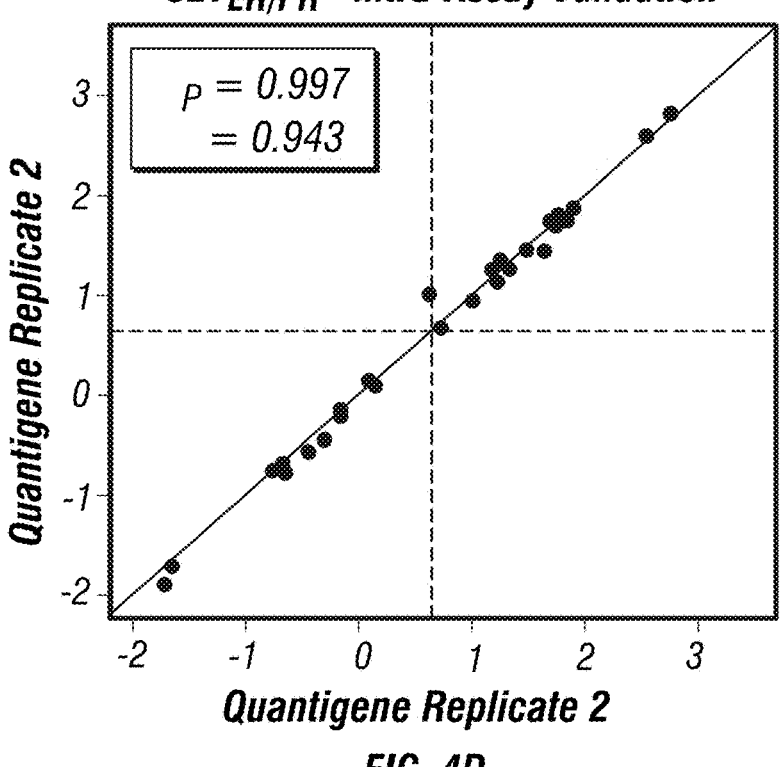
Figure 5A:
FIGS. 5A-B: Tests for reproducibility of the $SET_{ER/PR}$ index in primary breast cancers when comparing across assay type and sample type (Translation to Nanostring nCounter Hybridization Assay): Translation of $SET_{ER/PR}$ from fresh-frozen (FF) RNA profiled on Affymetrix U133A microarray to Nanostring N-counter hybridization platform. (A) Calibration cohort of primary breast cancers to calibrate $SET_{ER/PR}$ index from U133A in FF sample to Nanostring platform using FFPE sample; (B) Validation cohort of primary breast cancers to test the calibrated $SET_{ER/PR}$ index using the Nanostring platform with FFPE sample.
Figure 5A:
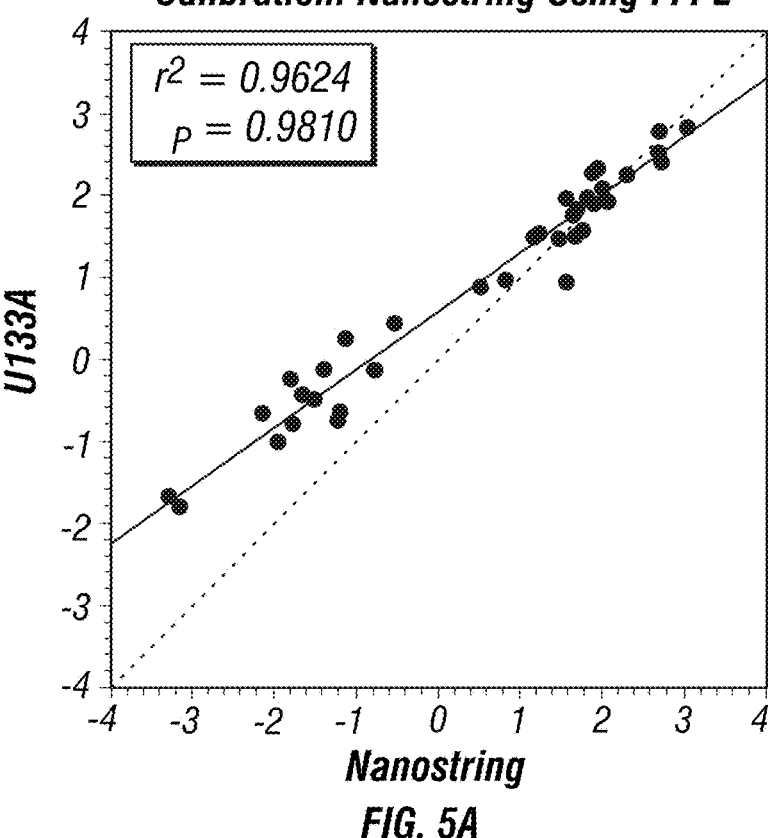
Figure 5B:
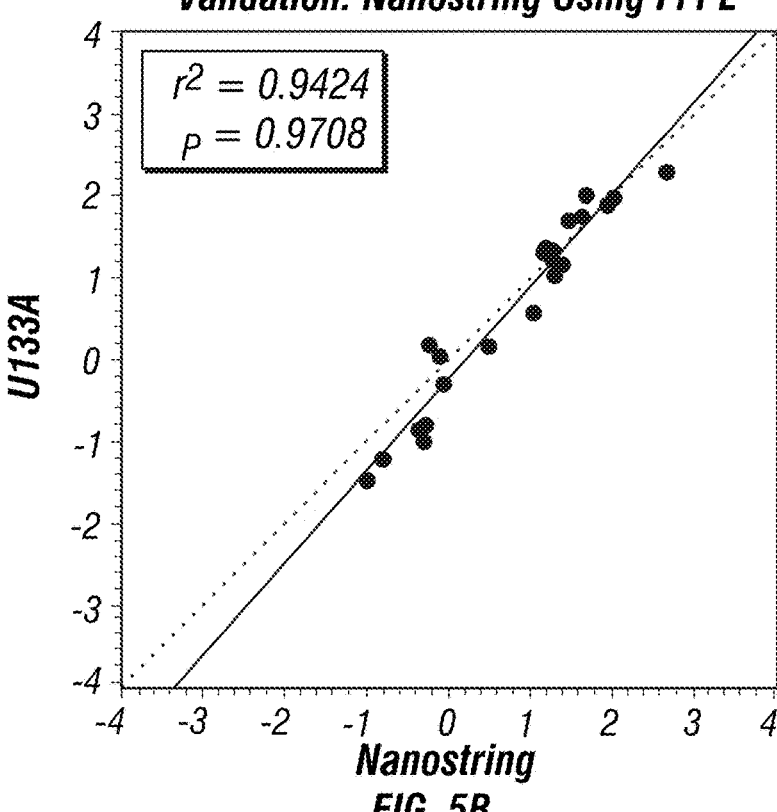
Figure 6A:
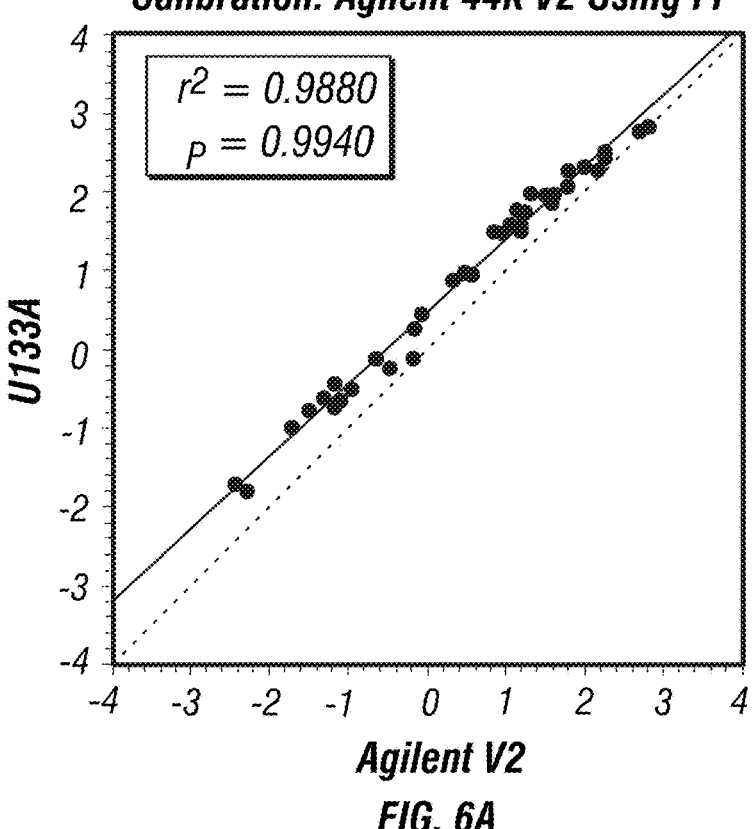
FIGS. 6A-D: Tests for reproducibility of the $SET_{ER/PR}$ index in primary breast cancers when comparing across assay type and sample type (Translation to Agilent 44K Microarray): Translation of $SET_{ER/PR}$ from fresh-frozen (FF) RNA profiled on Affymetrix U133A microarray to the 7                                                                    8
Figure 6B:
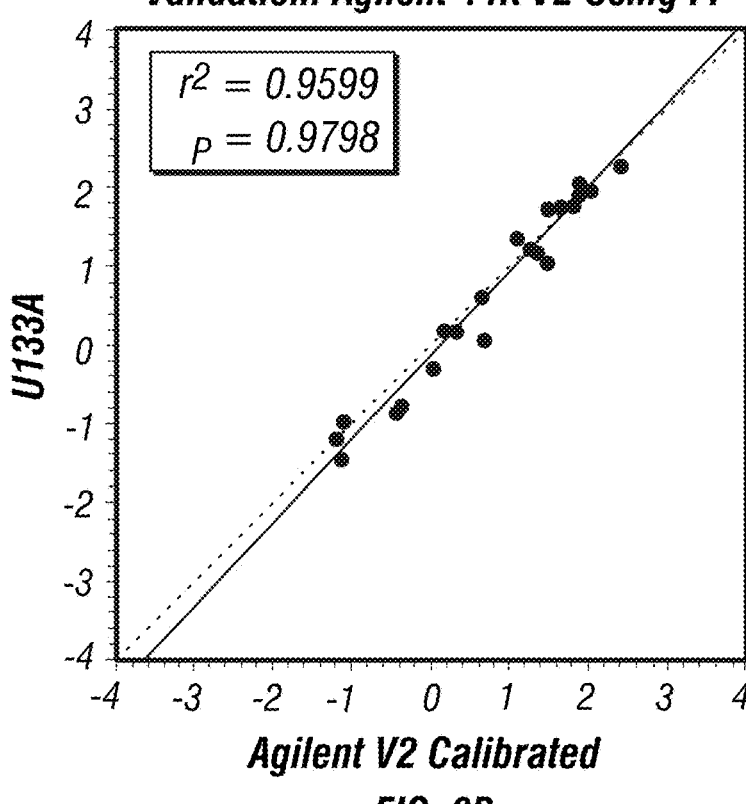
Figure 6C:
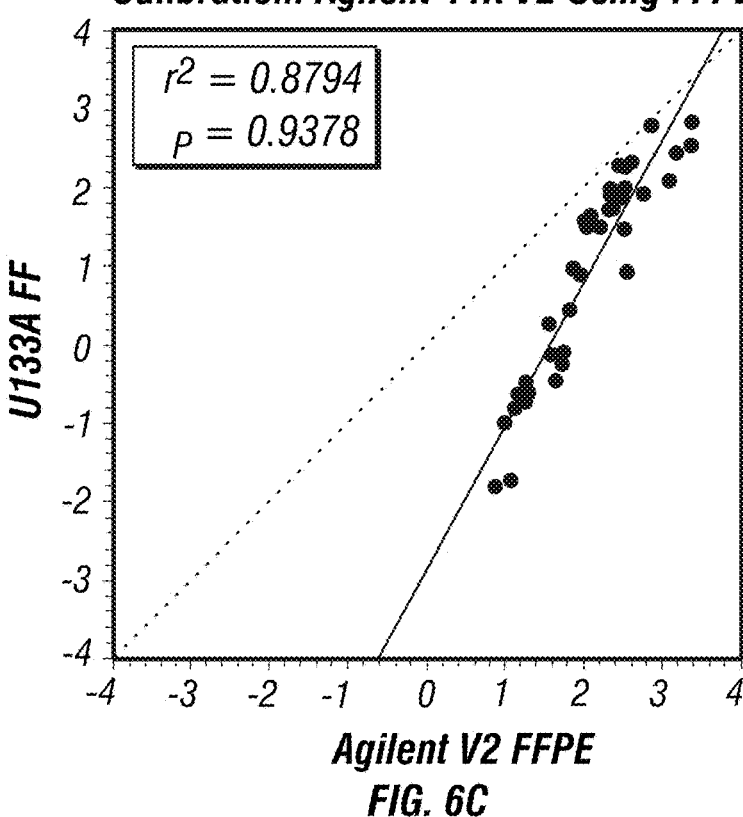
Figure 6D:
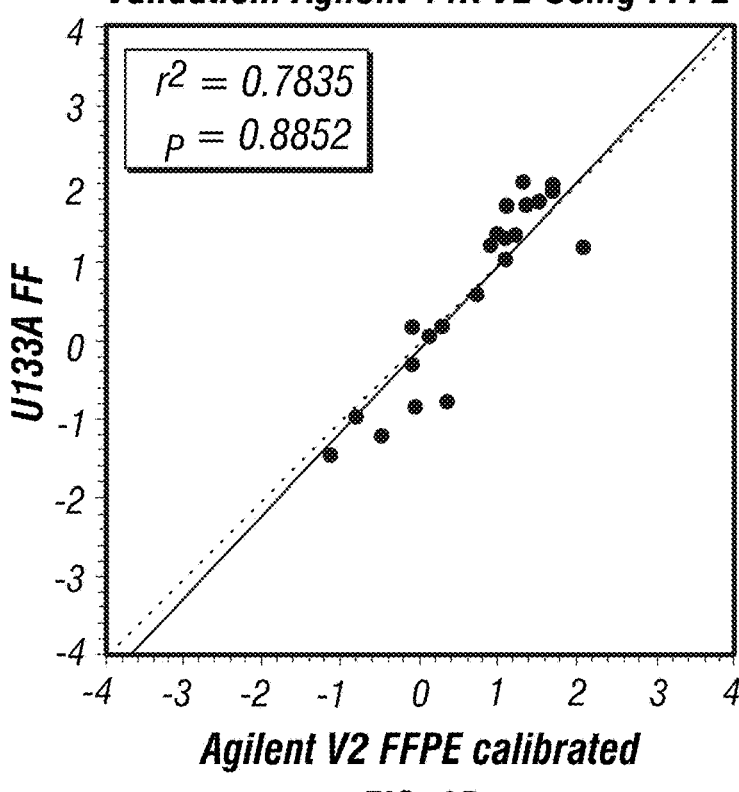
Figure 7A:
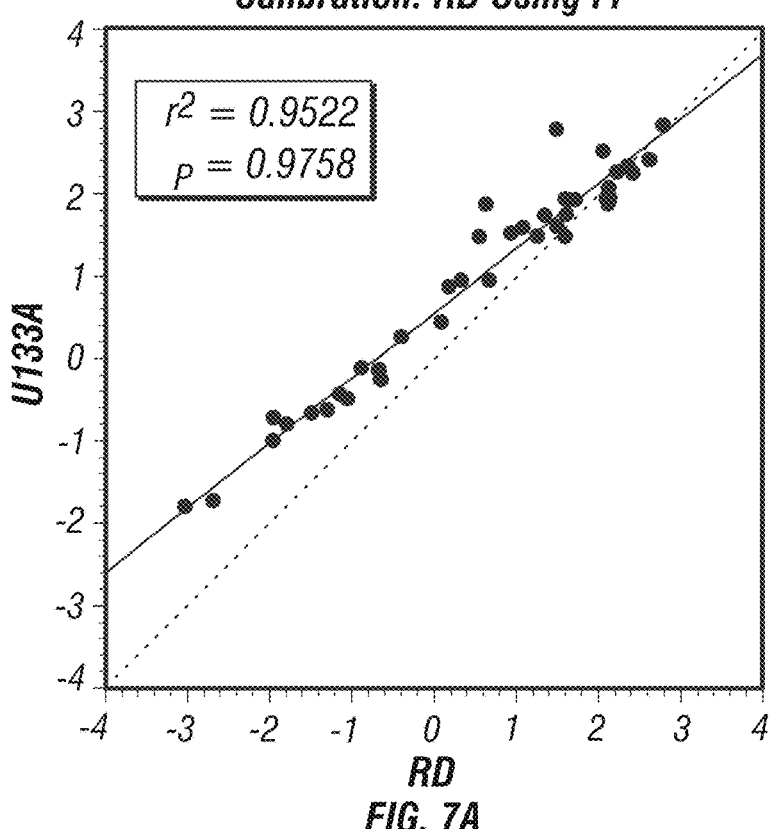
Figure 7B:
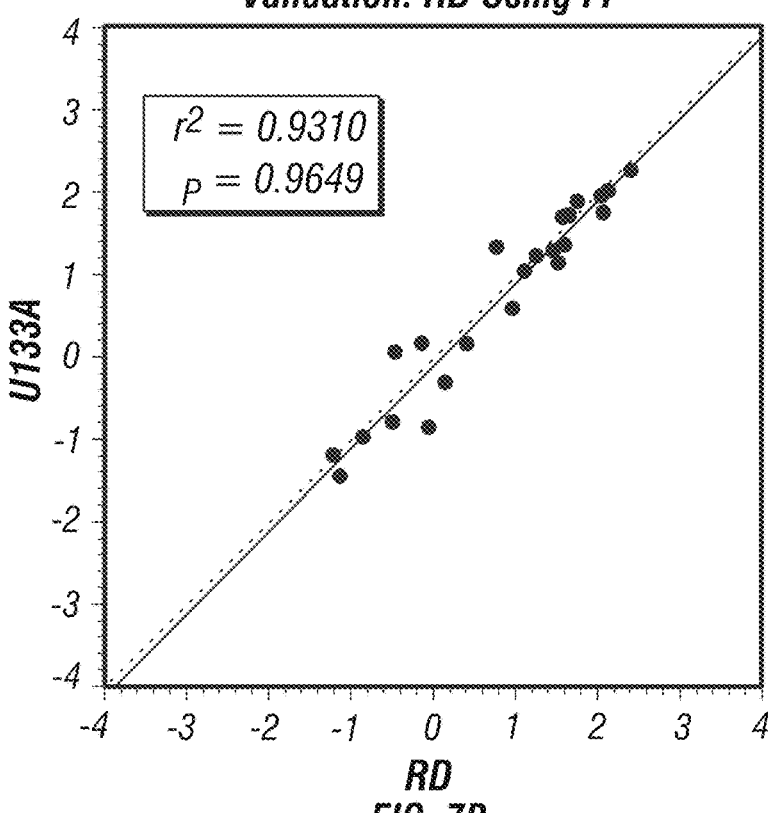
Figure 7C:
Figure 7C:
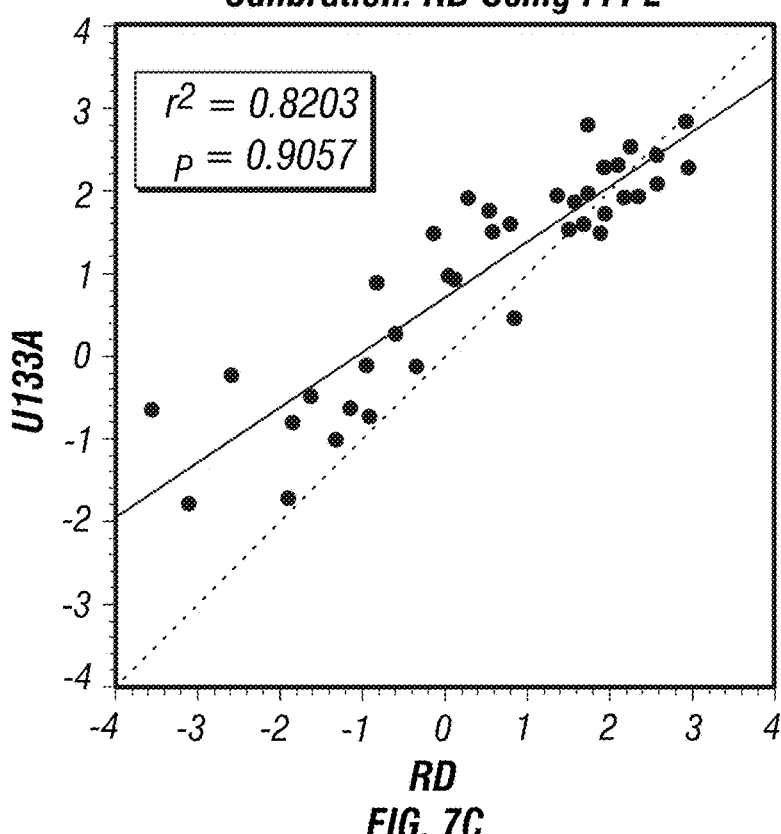
Figure 7D:
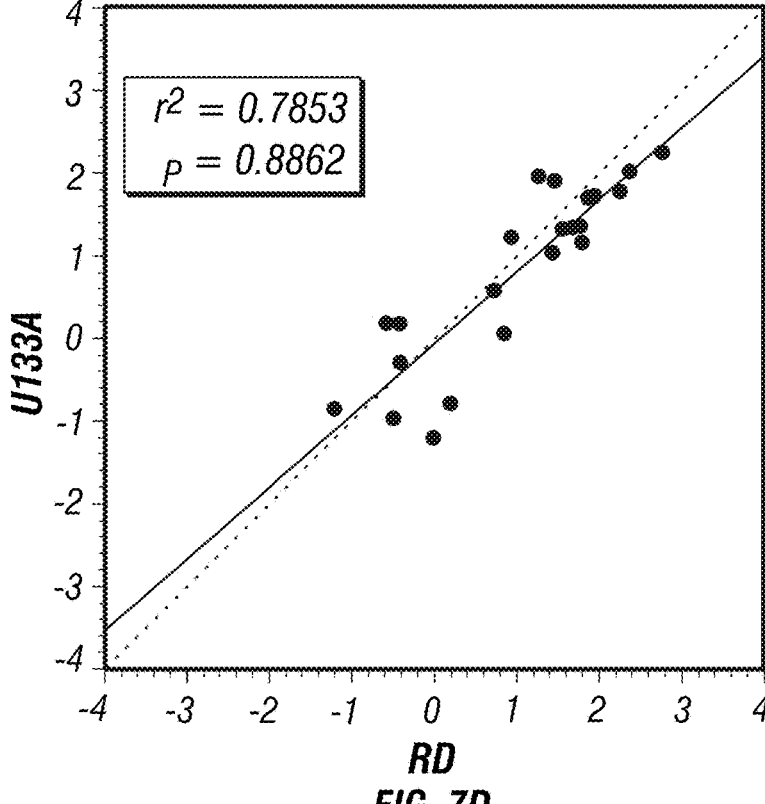

The threshold was selected to dichotomize the $SET_{ER/PR}$ that optimized the classification into treatment sensitive and insensitive cases at 6 months of PFS after the start of palliative endocrine therapy. Dichotomized in this way (with threshold of 0.65), $SET_{ER/PR}$ was independently prognostic for PFS on hormonal therapy in both univariate and multivariate analyses (Table 2). In particular, the theranostic effect was more pronounced in the subset of patients who had previously demonstrated clinical evidence of sensitivity to endocrine therapy. FIG. 3 shows Kaplan-Meier plots using this optimized threshold for $SET_{ER/PR}$ index in the same cohort of patients.

formed the experiments on different days. The technical reproducibility of the FFPE-based assay under these conditions was excellent (pp=0.994 and 0.997, respectively). A linear model was then fit using the mean of the two replicates of the array- and QuantiGene measurements of the 36 samples to evaluate the effect of the technology transfer on score values. The estimates for the technology transfer were then validated in a set of 31 independent samples profiled on both platforms. The inter-assay reproducibility was excellent with pp=0.980 and K=0.943 for risk stratification. Similar results were observed when the measurement of $SET_{ER/PR}$ index in FFPE samples were translated to other technical platforms, including Nanostring nCounter (FIG. 5), Agilent 44K version 2 gene expression microarrays (FIG. 6), and picodroplet-based targeted RNA sequencing using the combined RainDance (droplet targeting and amplification) and Illumina (sequencing) platforms (FIG. 7). This demonstrates that the $SET_{ER/PR}$ index of gene expression measurements robustly translates for use with different sample types and technical platforms. $SET_{ER/PR}$ index is based on the concept of measuring ESR1 and PGR-associated transcription, and its calculation avoids modeling on outcome data—a method prone to over-fitting. It is a reproducible gene expression assay that is based on 18 informative and 10 reference genes, and pilot results demonstrate how it can be translated for use with fixed tumor samples in routine clinical use. Furthermore, the $SET_{ER/PR}$ index was robust to critical pre-analytical conditions (tissue and cytologic samples, ex vivo ischemia, preservation or fixation of tissue samples, and intratumoral spatial heterogeneity) and analytical conditions (technical reproducibility at all levels of the assay procedure, different technical platforms for the assay).

$SET_{ER/PR}$ is the first multi-gene assay to be developed specifically for metastatic breast cancer. Higher $SET_{ER/PR}$ index was associated with longer progression-free and overall survival for patients with metastatic breast cancer treated by endocrine therapy, particularly for those who had previously demonstrated clinical sensitivity to hormonal therapy by prolonged progression-free interval in the adjuvant or palliative setting (Table 2, FIG. 3). Therefore, there is potential that $SET_{ER/PR}$ is a promising candidate for a further development as a diagnostic tool in the setting of palliative endocrine treatment.

Furthermore, it was demonstrated that the targeted next generation sequencing approach can include additional targeted probes to detect and measure the proportion of expressed sequence of estrogen receptor alpha gene (ESR1) transcript at the loci of known mutations of the gene. ESR1 is one of the transcripts in the $SET_{ER/PR}$ index and can be mutated in Stage IV metastatic breast cancer, due to ligand-independent activation of ER. This can be observed from the targeted RNA sequencing assay for the $SET_{ER/PR}$ index, wherein the fraction of mutated ESR1 transcripts can be measured, and this is associated with higher $SET_{ER/PR}$ index values (FIG. 8). It has been reported by others that mutations in the DNA for ESR1 is a possible cause of resistance to endocrine therapy for patients with metastatic breast cancer, and may be acquired due to previous endocrine treatments. Thus, some metastatic cancers with high $SET_{ER/PR}$ index have wild-type ESR1 (and might be expected to respond well to hormonal therapy) whereas others with high $SET_{ER/PR}$ index but frequently mutated ESR1 transcripts might demonstrate resistance to hormonal therapy (FIG. 8). The preliminary results demonstrate that measuring and analyzing the transcribed sequence at the known loci of relevant mutations in ESR1, when combined with the measurement of the transcription that should result from normal ESR1 activation (measured by $SET_{ER/PR}$ index) provides a highly predictive diagnostic algorithm (FIG. 9). This addition includes within the assay whether the ESR1 gene was mutated at known loci and the proportion of the transcript that contain the mutation.

Example 2—Clinical Validation of $SET_{ER/PR}$ Index in Stage II to III Disease

The $SET_{ER/PR}$ index described in Example 1 relates to its use as a prognostic diagnostic test to predict improved progression-free and overall survival of patients who receive endocrine therapy for their metastatic breast cancer, and is based on testing of a routine formalin-fixed and paraffin-embedded (FFPE) tissue section from breast cancer that is Stage IV (i.e. metastatic).

The index was next tested for feasibility using different customized genomic technologies including RNA hybridization methods, e.g. QuantiGene Plex method (FIG. 4), and Nanostring method (FIG. 5), other types of microarray platform such as Agilent 44K version 2 arrays (FIG. 6), and targeted RNA sequencing methods that involve targeted reverse transcription of the source RNA (e.g. RainDance droplet amplification method) (FIG. 7), or an exon capture method (e.g. Illumina Targeted sequencing) after the preparation of a tagged library next generation sequencing. It was also found that the $SET_{ER/PR}$ index can be measured in tissue samples or blood samples (when there is sufficient RNA in the blood sample).

Furthermore, it was demonstrated that the targeted next generation sequencing approach can include additional targeted probes to detect and measure the proportion of expressed sequence of estrogen receptor alpha gene (ESR1) transcript at the loci of known mutations of the gene. ESR1 is one of the transcripts in the $SET_{ER/PR}$ index and can be mutated in Stage IV metastatic breast cancer, but is rare in original primary breast cancer. It has been reported by others that mutations in the DNA for ESR1 might be acquired due to previous endocrine treatments. However, the present data shows that the relevant mutations in ESR1, when measured by $SET_{ER/PR}$ index using the RD assay for targeted RNA sequencing approach, with much higher depth of sequencing reads than typically obtained from DNA sequencing methods, demonstrated that a low proportion (1-3%) of ESR1 transcript were mutated at known loci in 15% of previously untreated primary ER+ breast cancers (FIG. 10). Similar to the observation in metastatic cancers, the subset of primary cancers that contained rare mutated ESR1 transcripts were a subset of the cancers with higher values for $SET_{ER/PR}$ index (FIG. 10). Thus, the inter-relationship between $SET_{ER/PR}$ index value and proportion of mutant ESR1 transcripts was observed in both relapsed metastatic cancer samples (FIG. 8) and in untreated primary cancers (FIG. 10)

The $SET_{ER/PR}$ index was also shown to independently predict relapse-free survival outcome for patients with Stage II-III breast cancer that was HR+/HER2− and who received sequential taxane-based and anthracycline-based chemotherapy regimens as preoperative treatment, i.e. neoadjuvant chemotherapy (NAC), followed by surgery for local tumor treatment and to evaluate tumor response using the residual cancer burden (RCB) prognostic score, and then received any standard adjuvant hormonal therapy as adjuvant treatment. In that population, there were three variables that were each independently prognostic: the original burden of disease at time of diagnosis, i.e. clinical Stage (c-Stage); the burden of residual cancer after completion of the chemotherapy (RCB index); and the $SET_{ER/PR}$ index to predict sensitivity to the subsequent adjuvant hormonal therapy (Table 3). This was observed in two different cohort of patients with median follow up (f-up) of 8 years and 5 years, respectively (Table 3).

TABLE 3

Prognostic evaluation of the SET$_{ER/PR}$ index in the context of
neoadjuvant chemotherapy (NAC), followed by adjuvant hormonal therapy for Stage II-III
HR+/HER2− breast cancer.

| | NAC #1 (N = 175, 8 years of follow up) | | | | NAC #2 (N = 130, 5 years of follow up) | | | |
| | HR | lower 95 | upper 95 | p = | HR | lower 95 | upper 95 | p = |
|---|---|---|---|---|---|---|---|---|
| | Univariate: All HR+/HER2− | | | | Univariate: All HR+/HER2− | | | |
| SET$_{ER/PR}$ | 0.72 | 0.57 | 0.90 | 0.004 | 0.78 | 0.59 | 1.03 | 0.08 |
| | Univariate: HR+/HER2− with RCB-II/III | | | | Univariate: HR+/HER2− with RCB-II/III | | | |
| SET$_{ER/PR}$ | 0.23 | 0.10 | 0.53 | <0.01 | 0.32 | 0.07 | 1.35 | 0.13 |
| | Multivariate: All HR+/HER2− | | | | Multivariate: All HR+/HER2− | | | |
| c-Stage III | 2.07 | 1.13 | 3.78 | <0.01 | 5.34 | 1.72 | 16.60 | <0.01 |
| RCB | 3.12 | 2.13 | 4.70 | <0.01 | 1.57 | 1.05 | 2.34 | 0.03 |
| SET$_{ER/PR}$ | 0.43 | 0.31 | 0.58 | <0.01 | 0.64 | 0.42 | 0.96 | 0.03 |

FIG. 11 shows the relationship between the SET$_{ER/PR}$ index and the residual cancer burden (RCB) after completion of NAC in patients who had clinical Stage II-III HR$^+$/HER2− breast cancer at time of initial diagnosis. The example particularly identified many patients with moderate residual cancer after NAC (RCB-II) and high SET$_{ER/PR}$ index (solid line) whose prognosis from subsequent adjuvant hormonal therapy was excellent (FIG. 11B). Yet other patients had poor prognosis from the combination of extensive residual disease after NAC (RCB-III) and low SET$_{ER/PR}$ index (dashed line), as shown in FIG. 11B.

The SET$_{ER/PR}$ index was also shown to extend to patients with Stage II-III breast cancer as a prognostic diagnostic test to predict excellent disease-free, relapse-free, and overall survival of patients who receive endocrine therapy as adjuvant treatment. Blinded clinical validation study results are shown in FIG. 12. This was a blinded validation analysis of primary tumor samples from patients who received a standard chemotherapy (FEC$_{x3}$/D$_{x3}$) followed by standard adjuvant hormonal therapy prescribed for at least 5 years. The SET$_{ER/PR}$ index was calculated from U133A gene expression microarrays using RNA from frozen tumor samples.

Although this result in FIG. 12 is from a blinded independent analysis of an external cohort who were uniformly treated with a taxane-anthracycline chemotherapy regimen, a larger sample size will be used to obtain more precise estimates of the ten-year distant relapse-free survival rate in the patients with high SET$_{ER/PR}$ index. Ten years is an appropriate endpoint for survival analyses in the HR+/HER2− patient population. A 10-year DRFS of greater than 90% would be a clinically useful and actionable result because it would identify patients with outstanding survival probability despite nodal metastases at the time of diagnosis. In future studies, this might be an appropriate population and survival benchmark for comparisons of alternative treatment options that would avoid chemotherapy, such as hormonal therapy alone or hormonal therapy with a targeted molecular therapy. Conversely, the concerning prognostic risk for patients with low SET$_{ER/PR}$ index might itself be clinically useful to encourage participation in the many adjuvant clinical trials that are becoming available to patients with stage II to III disease (such as palbociclib or everolimus).

Example 3—Materials and Methods

Patients and Samples

Discovery dataset (N=389): The first part was a subset of a published dataset (Symmans et al., 2010) of 437 Affymetrix U133A microarray profiles from patients at The University of Texas MD Anderson Cancer Center (MD Anderson) with newly diagnosed invasive breast cancer. 242 hormone receptor-positive cases with available information on estrogen receptor 1 (ESR1), progesterone receptor (PGR) and HER2− status were used. 181 additional hormone receptor-negative cases of this dataset were used for scaling of the score. The second part consisted of 147 new samples of patients with hormone receptor-positive breast cancer of patients at MD Anderson who participated in a research protocol to obtain FNA of newly diagnosed breast cancer or tissue samples after surgery for invasive breast cancer. The patients did not receive systemic treatment prior to sample collection. Samples were stored in RNAlater. Table 4 shows receptor status, stage and type of tissue samples of patients in the discovery cohort.

TABLE 4

Discovery cohort receptor status, AJCC
stage and type of sample.

| | Receptor Status | | AJCC Stage | | | | | Sample | |
| | HR+/HER2− | HR+/HER2+ | I | II | III | IV | NA | Tissue | Cytology |
|---|---|---|---|---|---|---|---|---|---|
| Discovery I | 204 | 38 | 4 | 127 | 110 | 1 | 0 | 0 | 242 |
| Discovery II | 28 | 19 | 20 | 80 | 20 | 1 | 26 | 134 | 13 |
| Total | 332 | 57 | 24 | 207 | 130 | 2 | 26 | 134 | 272 |

Clinical cohort for stage IV breast cancer (N=140): The clinically annotated dataset consisted of patients who participated in a research protocol to obtain fine-needle aspiration (FNA) of metastatic breast cancer at MD Anderson between 2004 and 2013. Patients were treated according to the choice of the patient and physician. 329 cases were available in the research database for the retrospective analysis. 234 were profiled on Affymetrix U133A microarrays. 212 microarrays passed quality control. 32 HER2-positive and 26 hormone receptor-negative tumors were excluded. 14 additional cases were excluded for other reasons (no follow-up data after biopsy, diagnosis other than breast cancer) resulting in 140 cases used in this study. Median follow-up times were 5.1 months for progression-free survival and 18.6 months for overall survival (Table 2).

ER- and PR-positivity was defined by nuclear staining of $\geq 10\%$ of tumor cells. HER2 positivity was defined as an immunohistochemistry score of 3+ and/or a HER2/CEP17 ratio of >2.2 as determined by fluorescence in-situ hybridization. The manuscript was written according to the REMARK guidelines (McShane et al., 2006).

Molecular Assays

Affymetrix U133A microarrays: RNA was extracted, processed and hybridized to Affymetrix human genome U133A microarrays (U133A GeneChip, Affymetrix, Santa Clara, CA, USA) as described previously. In brief, the raw intensity files were processed using the MAS5.0 algorithm to generate probeset-level intensities, normalized to a median array intensity of 600, log 2-transformed and scaled using the expression of 1,322 breast cancer reference genes within each sample (Symmans et al., 2010; Hatzis et al., 2011).

Affymetrix QuantiGene Plex platform: The QuantiGene Plex assay (Affymetrix, Sanata Clara, CA, USA) is hybridization-based multiplex platform based on fluorescent beads to capture specific RNA sequences using a tree-like signal-amplification. FFPE tissue homogenates were prepared using one single 10 μm FFPE slide with the QuantiGene Sample Processing Kit for FFPE Tissue Homogenates (Affymetrix, Sanata Clara, CA, USA) according to the manufacturer's instructions. A customized QuantiGene Plex reagent System was used with a customized selection of pre-designed gene-specific assays to capture the 10 reference genes and 18 target genes. The raw values were background corrected by subtracting the background value and log 2-transformed.

Inter-assay reproducibility (U133A vs. Plus2): This dataset is a subset of the MicroArray Quality Control study (MAQC, to be described elsewhere) consisting of 88 hormone receptor-positive breast cancer samples from three different centers. The tissue samples were taken from surgical specimens of patients without any prior systemic treatment. The samples were then chopped in pieces, mixed, split up in two equal parts and stored in RNAlater for processing on both Affymetrix U133A and Plus2.0 microarrays at MDACC. The probeset-wise Pearson correlation coefficients were calculated for each of the 22,277 probesets available on both platforms. Information from this dataset was used for development of $SET_{ER/PR}$.

Inter-sample type reproducibility (cytology vs. tissue): This dataset included 87 cases from the cross-platform dataset, one additional hormone receptor-positive case and 28 hormone receptor-negative cases. In addition to the tissue samples taken after surgery as described above, at the same time a scrape (=cytology) sample was taken by scraping with a scalpel over the cut-surface of the tumor. Samples were stored in RNA later for processing on U133A microarrays. Pearson correlation coefficients were calculated for each probesets to evaluate reproducibility using different tissue types. Information from this dataset was used for development of $SET_{ER/PR}$.

Intra-assay reproducibility and intratumoral heterogeneity: These samples were collected using a subset of 49 surgical specimens of the inter-sample type dataset and 2 additional cases. Three tissue samples were taken from different macroscopic tumor areas of the same tumor. One sample (A) was used for the technical reproducibility study. The sample was chopped in pieces, mixed and 80% were used to repeat the laboratory protocol at five different levels: RNA extraction, cDNA synthesis, cRNA synthesis and rescan of the same chip. The remaining 20% of the sample mix were used to repeat all steps, resulting in a total of six technical replicates. The additional tumor samples (B) and (C) were profiled to be used together with original sample (A) for the spatial reproducibility study. Using the 20×6 and 51×3 data points of the two nested datasets, the intraclass-correlation coefficient (ICC) for each probeset on the array was calculated in each dataset to obtain a measure of technical and spatial reproducibility, respectively. The ICC can be interpreted as the fraction of the total variation in the data that can be attributed to differences between different tumor samples. For example, an ICC of 0.95 means that 95% of the total variation can be explained by differences between tumors and 5% by differences within tumors. Information from this dataset was used for validation of the reproducibility of $SET_{ER/PR}$.

Dataset for the effects of tissue handling: This was a published dataset of 11 tumors of previously untreated patients with breast cancer that were collected at the time of intraoperative pathology assessment at MD Anderson. The design of the study and the details on the statistical analysis are described previously (Giordano et al., 2014). In brief, the tissue samples were minced, mixed and divided into eight equal portions. One portion was placed immediately in RNAlater. The remaining portions were placed RNAlater after being held at room temperature for 20, 40, 60, 120, or 180 minutes, or snap frozen in dry ice immediately (0 minutes or baseline) and after 40 minutes at room temperature. A linear mixed-effects model (LME) with random within-group intercept was used to estimate the effect of sample preservation method (RNAlater vs. fresh frozen) and time delay (0 vs. 40 min) using the r package lme4 (Cardoso et al., 2014). The effect of sample stabilization delay (cold ischemic time) was assessed using a similar model with fixed slope (for the cold ischemic time effect) and a random intercept (for biological variation among tumors). The statistical significance of the coefficients was evaluated by using the likelihood ratio test to compare the full model with a reduced model that did not include the term of interest. Information from this dataset was used for validation of the reproducibility of $SET_{ER/PR}$.

Contamination with liver and normal tissue: A dataset of 11 breast cancer samples that were pooled with 11 individual liver samples at different ratios: 0%, 5%, 10%, 15%, 20%, 25%, 50%, 75%, 90% and 100% liver. For the normal tissue contamination dataset, 11 breast cancer samples that were pooled with 11 individual normal breast tissue samples using the same ratios. Information from this dataset was used for validation of the reproducibility of $SET_{ER/PR}$.

Validation of Inter-assay reproducibility; inter-lab reproducibility: A published dataset of 16 cases, that were profiled on two different microarray platforms (U133A and Plus2) and in two different laboratories (MDACC and JBI) was used to validate cross-platform reproducibility and to evaluate the effect of processing in different laboratories. Information from this dataset was used for validation of the reproducibility of $SET_{ER/PR}$.

A dataset of 36 cases was used to evaluate the feasibility of the customized assay. All samples were profiled in duplicate on U133A microarrays and on the Quantigene Plex platform. A linear model was fit to evaluate the platform effect and to develop conversion factors for the new platform. This dataset was also used to validate the intra-assay reproducibility of the $SET_{ER/PR}$ in both platforms. For validation of the results, another set of 36 tumors was profiled on both platforms.

Relationship of the datasets: FIG. 13 illustrates the study designs for the different comparisons of pre-analytical and analytical conditions that were used to identify the most reliable genes to measure in the algorithm in order to calculate the $SET_{ER/PR}$ index, and the corresponding results from those studies are presented in FIGS. 1&2. FIG. 14 shows the partial overlap of the cases and/or samples of the different datasets. Of the 147 patients in part II of the discovery cohort, 88 patients were also included in the cross-platform dataset. Among those were 77 with overlapping samples, i.e. for 77 of the 147 U133A arrays used in discovery, additional matched PLUS2.0 array data was available. In the remaining 11 cases, the tumor of the same patient was used, but an individual sample was taken and profiled separately on U133A and PLUS2.0 arrays. 39 of the 51 patients in the spatial reproducibility study were also included in the discovery datasets. In 13 cases, one of the three samples from different tumor areas was also used for discovery, in 26 cases, 3 individual tumor samples and U133A microarray profiles were used. 50 of the 51 patients in the spatial reproducibility study were also included in the cross-tissue dataset, but different tumor samples and microarray profiles were used.

Selection of ESR1- and PGR-related genes: The goal of the feature selection process was to identify a small number of probesets that are both associated with ESR1- and PGR-expression but are also highly reproducible. A series of unspecific and specific filtering steps was applied using the training dataset as well as information derived from the different technical datasets (FIG. 15). The seven consecutive steps were as follows:

1. To select probesets with a high reproducibility, unspecific filtering for the selection of ESR1- and PGR-associated genes was mainly based on reproducibility: only probesets with a intraclass correlation coefficient of at least 0.6 for both technical and spatial reproducibility were retained.
2. Then, reference probesets were removed ("AFFX" in the probeset ID).
3. Probesets with low expression (expression of at least 5 in less than 40% of samples) and/or low variability in the discovery dataset (interquartile range smaller than 0.5 and/or range between 5th and 95th quantile smaller than 1) were removed.
4. Probesets associated with Aurora kinase A expression as a surrogate for proliferation were removed (discovery dataset, Spearman$\rightarrow$>0.5).
5. Of the remaining 6826 probesets, only probesets with an absolute Spearman correlation coefficient of at least 0.3 for both ESR1 and PGR were selected, resulting in 158 probesets (discovery dataset).
6. To further reduce the number of candidates, only those with good reproducibility across different microarray platforms (cross-platform correlation >0.9) and high variability (discovery dataset; inter-quartile range >1.5) were kept. This step left 24 probesets representing 18 genes.

7. One representative gene was selected for each probeset using a voting scheme including all expression and quality metrics described above.

Selection of Reference genes: For selection of the reference genes, only the 331 HER2-negative cases of the discovery cohort were used. For the selection of reference genes, the following filtering steps were applied to the 22,283 available probesets:

1. ICC for technical reproducibility >0.9, ICC for spatial reproducibility >0.8.
2. No strong correlation with ER, PR or HER2 (abs.$\rightarrow$<0.4).
3. Good cross-tissue ($\rightarrow$>0.8) and cross-platform reproducibility ($\rightarrow$>0.8).
4. Variance of <0.2 and 95% of values within a range of 1.75. As probeset variance is typically a function of probeset intensity, the variance criterion was loosened to cover lower expression ranges, too (variance of <0.75 for a median gene expression range from 8-9 and to variance <1.5 to cover a range of 7-8). From the probesets passing all filtering criteria, 10 representative genes were selected.

Definition of $SET_{ER/PR}$: FIG. 16 shows the distribution of the selected target and reference genes and Table 5 lists the annotations. In FIG. 17A, the mean of the target genes is plotted against the mean of the reference genes to illustrate the much tighter distribution of the reference genes. Using the 389 cases of the discovery dataset and 175 additional hormone receptor-negative cases, the score was scaled linearly to optimize the discrimination of hormone receptor-positive vs. hormone receptor-negative cases at a $SET_{ER/PR}$ value of 0 (FIG. 17B).

TABLE 5

ESR1-and PGR-associated genes and reference genes.

| Symbol | Name | Entrez ID | Band |
|---|---|---|---|
| SLC39A6 | Solute carrier family 39 (zinc transporter), member 6 | 25800 | 18q12.2 |
| STC2 | Stanniocalcin 2 | 8614 | 5q35.1 |
| CA12 | Carbonic anhydrase XII | 771 | 15q22 |
| ESR1 | Estrogen receptor 1 | 2099 | 6q25.1 |
| PDZK1 | PDZ domain containing 1 | 5174 | 1q21 |
| NPY1R | Neuropeptide Y receptor Y1 | 4886 | 4q32.2 |
| CD2 | CD2 molecule | 914 | 1p13.1 |
| MAPT | Microtubule-associated protein tau | 4137 | 17q21.1 |
| QDPR | Quinoid dihydropteridine reductase | 5860 | 4p15.31 |
| AZGP1 | Alpha-2-glycoprotein-l, zinc-binding | 563 | 7q22.1 |
| ABAT | 4-aminobutyrate aminotransferase | 18 | 16p13.2 |
| ADCY1 | Adenylate cyclase 1 | 107 | 7p12.3 |
| CD3D | CD3D molecule, delta (CD3-TCR complex) | 915 | 11q23 |
| NAT1 | N-acetyltransferase 1 (arylamine N-aminotransferase) | 9 | 8p22 |
| MRPS30 | Mitochondrial ribosomal protein S30 | 10884 | 5q11 |
| DNAJC12 | DNAJ (Hsp40) homolog, subfamily C, member 12 | 56521 | 10q22.1 |
| SCUBE2 | Signal peptide, CUB domain, EGF-like 2 | 57758 | 11p15.3 |
| KCNE4 | Potassium channel, voltage-gated subfamily E regulatory subunit 4 | 23704 | 2q36.1 |
| LDHA | Lactate dehydrogenase A | 3939 | 11p15.4 |
| ATP5J2 | ATP synthase, mitochondrial Fo complex, subunit F2 | 9551 | 7q22.1 |
| VDAC2 | Voltage dependent anion channel 2 | 7417 | 10q22 |
| DARS | Aspartylt tRNA synthetase | 1615 | 2q21.3 |
| UGP2 | UDP-glucose phosphorylase 2 | 7360 | 2p14-p13 |

TABLE 5-continued

| ESRI-and PGR-associated genes and reference genes. | | | |
|---|---|---|---|
| Symbol | Name | Entrez ID | Band |
| UBE2Z | Ubiquitin-conjugating enzyme E2Z | 65264 | 17q21.32 |
| AK2 | Adenylate kinase 2 | 204 | 1p34 |
| WIPF2 | WAS/WASL interacting protein family, member 2 | 147179 | 17q21.2 |
| APPBP2 | Amyloid beta precursor protein (cytoplasmic tail) binding protein 2 | 10513 | 17q23.2 |
| TRIM2 | Tripartite motif containing 2 | 23321 | 4q31.3 |

Reproducibility of $SET_{ER/PR}$: Cross-platform reproducibility shown in Table 6 lists the results of the linear model for cross-platform reproducibility using the first dataset. The estimates were then validated with the second dataset after conversion of the signature using U133A≈1*Plus2-0.2.

TABLE 6

| Linear model to evaluate the influence of platform bias | | | | |
|---|---|---|---|---|
| | Estimate | Standard Error | t-value | p-value |
| Intercept | −0.240 | 0.0258 | −9.298 | <0.001 |
| Platform | 0.966 | 0.0145 | 66.803 | <0.001 |

Consistent measurements of $SET_{ER/PR}$ index across technicians, batches of reagents, and over time: FIG. 18 shows the result from 20 consecutive weekly tests of $SET_{ER/PR}$ index in 5 different breast cancer samples. In each case, the laboratory standard operating protocol (SOP) was followed, beginning with direct lysis of unstained FFPE tissue sections (without prior RNA purification) and measurement of genes expression using the Quantigene method. Two laboratory technicians (shown as different colors) alternated to perform the weekly measurements and each technician utilized 3 different batches of Quantigene reagents during the course of the study. The $SET_{ER/PR}$ index was consistently reproducible over 20 consecutive measurements, each starting from the level of an unstained FFPE tissue section.

Figure 19:
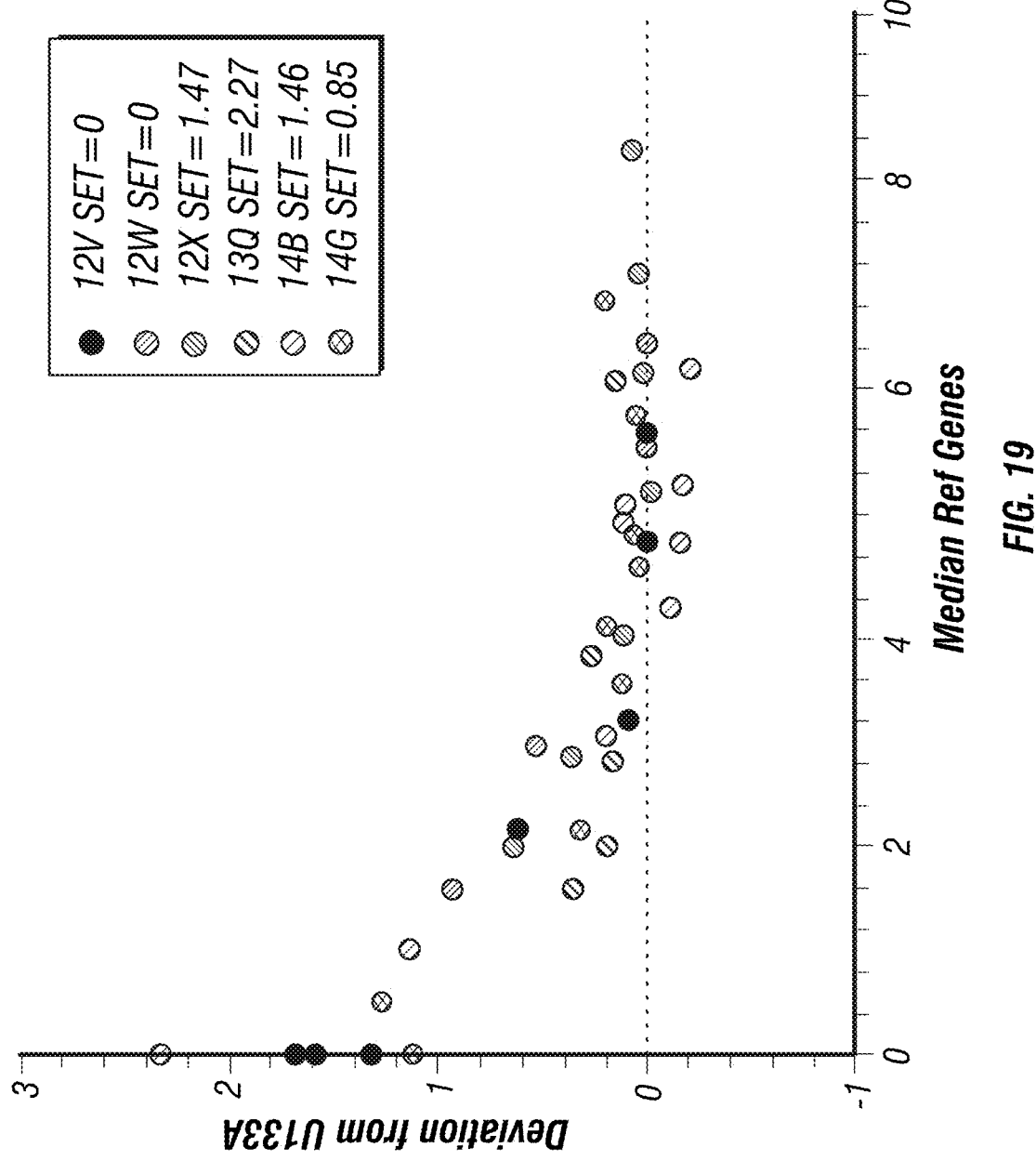

Quality control for measurements of $SET_{ER/PR}$ index: FIG. 19 shows that a median reference gene value of greater than 4.0 (log 2 scale) provides an appropriate cutpoint for quality assessment of an acceptable $SET_{ER/PR}$ index result. This was determined from a limiting dilution study to determine a minimum threshold for reporting $SET_{ER/PR}$ index measurements with FFPE samples and Quantigene platform. Limiting dilutions of RNA derived from FFPE tissue (125 ng-1.95 ng) were assayed from five primary breast cancers. The measurements were compared with the $SET_{ER/PR}$ index value measured using fresh/frozen RNA profiled on U133A microarray. The absolute deviation of the $SET_{ER/PR}$ index measurement from the U133A was apparent when the median expression of reference genes was <4.0 (log 2 scale). There was no deviation for $SET_{ER/PR}$ index values when the median of reference genes expression was >4.0.

Effect of cold ischemia on $SET_{ER/PR}$: Table 7 lists the results of the linear-mixed effects model with random within group intercept to estimate the effect of sample preservation method (RNAlater vs. fresh frozen) and time delay (0 vs. 40 min) on $SET_{ER/PR}$. Table 8 lists the results of the model for the effect of sample stabilization delay (cold ischemic time) with fixed slope (for the cold ischemic time effect) and a random intercept (for biological variation among tumors). The statistical significance of the coefficients was evaluated by using the likelihood ratio test to compare the full model with a reduced model that did not include the term of interest.

TABLE 7

| Linear mixed-effects analysis of the 2 × 2 study for the effect of sample preservation method and time delay on $SET_{ER/PR}$ *(0 vs. 40 min), **(RNAlater vs. fresh frozen). | | | |
|---|---|---|---|
| Fixed Effects | Estimate | 95% CI | p-value |
| Intercept | 0.99 | 0.13-1.84 | NA |
| Time Delay | 0.02 | −0.12-0.14 | 0.85 |
| Stabilization | −0.08 | −0.21-0.05 | 0.22 |
| Random Effects | Estimate | 95% CI | p-value |
| Between-tumor SD | 1.31 | NA | NA |
| Within-tumor SD | 0.20 | NA | NA |
| Intra-class correlation (ICC) | 0.97 | NA | NA |

TABLE 8

| Mixed-effects analysis of the effect of cold ischemic time on $SET_{ER/PR}$. | | | |
|---|---|---|---|
| Fixed Effects | Estimate | 95% CI | p-value |
| Intercept | 0.94 | 0.11-2.08 | NA |
| Cold Ischemic Time | −0.0003 | −0.0001-0.0005 | 0.47 |
| Random Effects | Estimate | 95% CI | p-value |
| Between-tumor SD | 1.28 | NA | NA |
| Within-tumor SD | 0.21 | NA | NA |
| Intra-class correlation (ICC) | 0.98 | NA | NA |

Stage-related changes of $SET_{ER/PR}$ index: FIG. 20 shows the decrease in $SET_{ER/PR}$ according to stage at diagnosis and the number of the biopsied relapse event in patients with metastatic breast cancer. $SET_{ER/PR}$ in metastatic breast cancer Table 9 gives a summary of the clinical and pathological characteristics of the subset of 79 metastatic breast cancer patients treated with endocrine-based therapy, Table 10 lists the protocol treatments. In FIG. 21, $SET_{ER/PR}$ is plotted according to clinical and pathological characteristics.

Measurement of $SET_{ER/PR}$ index in blood samples: FIG. 22 shows the comparison of expression measurements of $SET_{ER/PR}$ index genes, using the RD targeted RNA sequencing method, in matched samples of RNA from the metastatic breast cancer (derived from FFPE biopsy of a liver metastasis) and the RNA from the patient's peripheral blood (derived from plasma exosomes), and demonstrates the feasibility of measuring $SET_{ER/PR}$ index form blood samples.

TABLE 9

| Clinical and pathological characteristics of the subset of 79 patients with relapsed metastatic breast cancer and endocrine-based protocol treatment. | | |
|---|---|---|
| PR Status | N | % |
| Positive | 49 | 62 |
| Negative | 30 | 38 |
| Prior Endocrine Sensitivity | | |
| Sensitive | 46 | 58 |
| Resistant | 23 | 29 |
| No prior endocrine therapy | 10 | 13 |

TABLE 9-continued

Clinical and pathological characteristics of the subset
of 79 patients with relapsed metastatic breast cancer
and endocrine-based protocol treatment.

| PR Status | N | % |
|---|---|---|
| Number of Relapse Event (biopsied) | | |
| $1^{st}$-$2^{nd}$ | 53 | 67 |
| ≥$3^{rd}$ | 26 | 33 |
| Visceral Metastases Present | | |
| Visceral | 39 | 49 |
| Only Soft Tissue/Bone | 40 | 51 |
| Progression-Free Survival | | |
| Progression Event | 75 | 95 |
| Censored | 4 | 5 |
| Overall Survival | | |
| Death | 57 | 72 |
| Censored | 22 | 28 |

TABLE 10

Protocol treatment of the subset
of 79 patients with relapsed metastatic
breast cancer and endocrine-based therapy.

| Protocol Treatment | N |
|---|---|
| Tamoxifen | 9 |
| Tamoxifen & Goserelin | 1 |
| Anastrozole | 13 |
| Anastrozole & Goserelin | 4 |
| Anastrozole & Erlotinib | 1 |
| Anastrozole & Bevacizumab | 1 |
| Anastrozole & Gefitinib | 1 |
| Exemestane | 10 |
| Exemestane & Everolimus | 8 |
| Fulvestrant | 7 |
| Fulvestrant & Goserelin | 1 |
| Fulvestrant & Dasatinib | 1 |
| Letrozole | 8 |
| Letrozole & Goserilin | 2 |
| Letrozole & Imatinib | 2 |
| Letrozole & Leuprorelin | 1 |
| Megestrol acetate | 5 |
| Estradiol | 2 |
| Fluoxymesterone | 1 |
| TAS-108 | 1 |

Statistical Methods

Identification and selection of target and reference probesets from U133A microarrays: The purpose was to identify a small number of highly reproducible probesets that are associated with ESR1- and PGR-expression (probesets 205225_at and 208305_at) based on Spearman's rank correlation coefficient in the 389 cases of the discovery cohort. A series of unspecific and specific filtering steps was applied using the discovery dataset and analytical datasets to select probesets with good intra-tumoral and technical reproducibility, good reproducibility across different microarray platforms and across different types of tissue samples, and favorable expression metrics (by means of minimal expression levels and variability).

Pearson's correlation was used for the evaluation of cross-platform and cross-tissue reproducibility of each candidate probeset on the array. The intraclass-correlation coefficient (ICC) was used to evaluate intra-assay and intratumoral reproducibility. Probesets strongly associated with proliferation were removed. The final list included 18 probesets representing 18 ESR- and PGR-associated genes. For selection of the reference genes, 331 hormone receptor-positive, HER2-negative cases of the training dataset were used to select probesets with little variability and high reproducibility across samples. The final list included 10 probesets.

$SET_{ER/PR}$ was defined as:

$$SET_{ER/PR} = \frac{\sum_{i=1}^{18} T_i}{18} - \frac{\sum_{j=1}^{10} R_j}{10} + 2,$$

where $T_i$ is the expression of the ith of the 18 target genes and R, the expression of the jth of the 10 reference genes. A constant was added to optimize the separation into hormone receptor-positive and negative cases by immunohistochemistry at a score value of 0.

Analytical and pre-analytical performance of SET ER/PR: To examine the performance of the summarized $SET_{ER/PR}$ in the technical datasets used in the discovery process, we used the same methods as for the evaluation of the individual candidates. In addition, a linear model was fit to evaluate the effect of different microarray platforms. Pearson correlation was used to evaluate intra-assay, inter-assay and inter-laboratory reproducibility. A linear mixed-effects model (LME) with random within-group intercept was used to estimate the effect of sample preservation method (RNAlater vs. fresh frozen) and time delay (0 vs. 40 min) using the r package lme4. The effect of sample stabilization delay (cold ischemic time) was assessed using a similar model with fixed slope (for the cold ischemic time effect) and random intercept (for biological variation among tumors). The statistical significance of the coefficients was evaluated by using the likelihood ratio test to compare the full model with a reduced model that did not include the term of interest. To examine the impact of contamination with normal breast tissue and liver tissue, $SET_{ER/PR}$ values were plotted against the percentage of contaminant. Fleiss' K statistic for multiple raters was used to evaluate the reproducibility of risk class assignment.

$SET_{ER/PR}$ in metastatic breast cancer: For survival analyses, the R package survival was used. Progression-free survival was the time from the start of protocol treatment to disease progression or death from any cause. The endpoint for overall survival was death from any cause. Prior endocrine sensitivity was defined as a history of at least 6 months of progression-free survival while on endocrine therapy for metastatic disease or 5 years of progression-free survival while on adjuvant endocrine therapy for primary breast cancer. Logistic regression was used to model relationship between the continuous $SET_{ER/PR}$ and endocrine sensitivity and Cox regression for the relationship with survival outcomes. The Kaplan-Meier method and log-rank test were used to evaluate survival outcomes using the dichotomized score. All statistical analyses and computations were performed in R v. 3.1.2 (R Core Team, 2015) and Bioconductor (Huber et al., 2015).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Amir, E. et al. *J. Clin. Oncol.* 30, 587-592, 2012.
Austin-Ward and Villaseca, *Revista Medica de Chile*, 126 (7): 838-845, 1998.
Ausubel et al., Current Protocols in Molecular Biology, John Wiley & Sons, New York, NY, 2003.
Barrios, C. et al. *Ann. Oncol.* 23, 1378-1386, 2012.
Beslija, S. et al. *Ann. Oncol.* 18, 215-225, 2007.
Bukowski et al., *Clinical Cancer Res.,* 4(10):2337-2347, 1998.
Camacho et al. *J Clin Oncology,* 22(145), 2004.
Cardoso, F. et al. *Ann. Oncol.* 25, 1871-1888, 2014.
Carter, P. J., and Senter, P. D. *Cancer J* 14, 154-169, 2008.
Christodoulides et al., *Microbiology,* 144 (Pt 11):3027-3037, 1998.
Davidson et al., *J. Immunother.,* 21(5):389-398, 1998.
Dodwell, D. et al., *Breast* 15, 584-594, 2006.
Filipits, M. et al. *Clin. Cancer Res.* 17, 6012-6020, 2011.
Geiss et al. *Nature Biotechnology,* 26, 317-325, 2008.
Giordano, S. H. et al. *J. Clin. Oncol.* 32, 1-23, 2014.
Godfrey et al., *J. Mol. Diag.* 2:84-91, 2000.
Hanibuchi et al., *Int. J. Cancer,* 78(4):480-485, 1998.
Heid et al, *Genome Research* 6:986-994, 1996.
Hellstrand et al., *Acta Oncologica,* 37(4):347-353, 1998.
Hoefnagel, L. D. et al. *Breast Cancer Res.* 12, R75, 2010.
Hollander, Front. *Immun.,* 3:3, 2012.
Huber, W. et al. *Nat. Publ. Gr.* 12, 115-121, 2015.
Hui and Hashimoto, *Infection Immun.,* 66(11):5329-5336, 1998.
Hurwitz et al. *Proc Natl Acad Sci.* 95(17): 10067-10071, 1998.
International Patent Application No. WO1995001994
International Patent Application No. WO1998042752
International Patent Application No. WO2001014424
International Patent Application No. WO2013131962
International Patent Publication No. WO2000037504
International Patent Publication No. WO2006121168
International Patent Publication No. WO2009101611
International Patent Publication No. WO2009114335
International Patent Publication No. WO2010027827
International Patent Publication No. WO2011066342
International Patent Publication No. WO2015016718
Leal, M., *Ann N Y Acad Sci* 1321, 41-54, 2014.
Lower, E. E. et al. *Breast Cancer Res. Treat.* 90, 65-70, 2005.
McShane, L. M. et al. *Breast Cancer Res. Treat.* 100, 229-235, 2006.
Mellman et al., *Nature,* 480:480-489, 2011.
Mokyr et al., *Cancer Res.,* 58:5301-5304, 1998.
Paik, S. et al. *N. Engl. J. Med.* 351, 2817-2826, 2004.
Pardoll, Nature Rev *Cancer,* 12:252-264, 2012.
Qin et al., *Proc. Natl. Acad. Sci. USA,* 95(24):14411-14416, 1998.

R Core Team. R: A language and environment for statistical computing. R Foundation for Statistical Computing, Vienna, Austria, 2015.
Remington's Pharmaceutical Sciences 22nd edition, 2012.
Robinson et al., *Nature Genetics,* 45:1446-151, 2013.
Robinson, D. R. et al. *Nat. Genet.* 45, 1446-51, 2013.
Sambrook et al. *Molecular Cloning: A Laboratory Manual,* Cold Spring Harbor Press, Cold Spring Harbor, N Y, 1989.
Specht et al., *Am. J. Pathol.* 158:419-29, 2001.
Symmans, W. F. et al. *J. Clin. Oncol.* 28, 4111-4119, 2010.
Teicher, B. A. *Current cancer drug targets* 9, 982-1004, 2009.
Teicher, B. A. *Current opinion in oncology* 26, 476-483, 2014.
Thompson, A. M. et al. *Breast Cancer Res.* 12, R92, 2010.
Toy, W. et al. *Nat. Genet.* 45, 1439-45, 2013.
U.S. Patent Application No. 20110008369
U.S. Patent Application No. 2014022021
U.S. Patent Application No. 20140294898
U.S. Patent Application No. 20130259858
U.S. Patent Application No. 20140357660
U.S. Pat. No. 4,870,287
U.S. Pat. No. 5,538,848
U.S. Pat. No. 5,716,784
U.S. Pat. No. 5,723,591
U.S. Pat. No. 5,739,169
U.S. Pat. No. 5,760,395
U.S. Pat. No. 5,801,005
U.S. Pat. No. 5,824,311
U.S. Pat. No. 5,830,880
U.S. Pat. No. 5,844,905
U.S. Pat. No. 5,846,945
U.S. Pat. No. 5,885,796
U.S. Pat. No. 6,207,156
U.S. Pat. No. 7,473,767
U.S. Pat. No. 8,008,449
U.S. Pat. No. 8,017,114
U.S. Pat. No. 8,329,867
U.S. Pat. No. 8,354,509
U.S. Pat. No. 8,535,889
U.S. Pat. No. 8,735,553
US Patent Publication No. 2005/0260186
US Patent Publication No. 2006/0104968
Veer, L. J. Van et al. 415, 2002.

What is claimed is:

1. A kit for the measurement of expression levels of a plurality of endocrine genes from a sample from a subject, the kit comprising:

(a) a set of 18 biotin-labeled probes for detecting mRNA expression levels of each one of SLC39A6, STC2, CA12, ESR1, PDZK1, NPY1R, CD2, MAPT, QDPR, AZGP1, ABAT, ADCY1, CD3D, NAT1, MRPS30, DNAJC12, SCUBE2, and KCNE4, wherein each of the probes of the set specifically hybridizes to one of SLC39A6, STC2, CA12, ESR1, PDZK1, NPY1R, CD2, MAPT, QDPR, AZGP1, ABAT, ADCY1, CD3D, NAT1, MRPS30, DNAJC12, SCUBE2, and KCNE4; and (b) a set of 10 biotin-labeled probes for detecting mRNA expression levels of each one of LDHA, ATP5J2, VDAC2, DARS, UCP2, UBE2Z, AK2, WIPF2, APPBP2, and TRIM2, wherein each of the probes of the set specifically hybridizes to each one of LDHA, ATP5J2, VDAC2, DARS, UCP2, UBE2Z, AK2, WIPF2, APPBP2, and TRIM2.

2. The kit of claim 1, wherein the kit further comprises a package insert comprising instructions for using the kit, wherein the package insert comprises instructions for calculating an index $$\text{Index} = \frac{\sum_{i=1}^{18} T_i}{18} - \frac{\sum_{j=1}^{10} R_j}{10} + 2$$

where $T_i$ is the expression of an $i^{th}$ of a set of genes detected by the set of 18 biotin-labeled probes and $R_j$ the expression of an $j^{th}$ of a set of reference genes detected by the set of 10 biotin-labeled probes.

3. The kit of claim 2, wherein the package insert provides instructions for making a quality control determination for measuring the index.

4. The kit of claim 3, wherein the quality control determination comprises inputting a median reference gene value of greater than 4.0 (log 2 scale) as a threshold cutpoint for quality assessment.

5. The kit of claim 4, wherein an index greater than 0 identifies the subject as sensitive to endocrine therapy.

6. The kit of claim 5, wherein an index greater than 0.5 identifies the subject as sensitive to endocrine therapy.

7. The kit of claim 6, wherein an index greater than 1 identifies the subject as sensitive to endocrine therapy.

8. The kit of claim 2, wherein the package insert provides instructions for using the index as a prognostic index for cancer-free, relapse-free, or overall survival of the subject from a cancer.

9. The kit of claim 8, wherein the cancer is metastatic breast cancer.

10. The kit of claim 9, wherein the metastatic breast cancer is hormone receptor positive.

11. The kit of claim 10, wherein the hormone receptor is an estrogen receptor (ER).

12. The kit of claim 1, wherein the kit further comprises a set of quantitative RT-PCR (RT-qPCR) buffers and enzymes.

13. The kit of claim 1, wherein the sample is a biopsy sample from the subject.

14. The kit of claim 13, wherein the biopsy sample is formalin-fixed and paraffin-embedded (FFPE).

15. The kit of claim 14, wherein the kit further comprises reagents for isolating a plurality of RNAs from the FFPE sample.

16. The kit of claim 1, wherein an ESR1 probe in the set of 18 biotin-labeled probes for detecting mRNA expression levels of ESR1 detects a mutated ESR1 transcript.

* * * * *